United States Patent
Kumaran et al.

(10) Patent No.: US 12,012,626 B2
(45) Date of Patent: *Jun. 18, 2024

(54) PRODUCTION OF STEVIOL GLYCOSIDES THROUGH WHOLE CELL BIOTRANSFORMATION OF STEVIOL GLYCOSIDE INTERMEDIATES

(71) Applicant: Manus Bio Inc., Cambridge, MA (US)

(72) Inventors: Ajikumar Parayil Kumaran, Watertown, MA (US); Christine Nicole S. Santos, Newton, MA (US); Jason Eric Donald, Lexington, MA (US); Mary Elizabeth Fowler, Somerville, MA (US); Ryan N. Philippe, Somerville, MA (US); Christopher Scott Frei, Weymouth, MA (US); Aaron Love, Boston, MA (US)

(73) Assignee: Manus Bio Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/546,758

(22) Filed: Dec. 9, 2021

(65) Prior Publication Data

US 2022/0162658 A1 May 26, 2022

Related U.S. Application Data

(63) Continuation of application No. 16/512,874, filed on Jul. 16, 2019, now Pat. No. 11,230,724.

(60) Provisional application No. 62/698,617, filed on Jul. 16, 2018.

(51) Int. Cl.
*C12P 19/18* (2006.01)
(52) U.S. Cl.
CPC .................................. *C12P 19/18* (2013.01)
(58) Field of Classification Search
None
See application file for complete search history.

(56) References Cited

U.S. PATENT DOCUMENTS

| | | | | |
|---|---|---|---|---|
| 10,463,062 B2* | 11/2019 | Philippe | ......... | C12Y 114/13079 |
| 10,743,567 B2* | 8/2020 | Philippe | ......... | C12Y 204/01017 |
| 11,168,309 B2* | 11/2021 | Donald | ......... | C12P 19/56 |
| 11,230,724 B2* | 1/2022 | Kumaran | ......... | C12N 9/92 |
| 2014/0329281 A1* | 11/2014 | Houghton-Larsen | ......... | C12N 9/0073 |
| | | | | 435/252.33 |
| 2017/0332673 A1* | 11/2017 | Philippe | ......... | A23L 27/36 |
| 2018/0223264 A1* | 8/2018 | Vroom | ......... | C12N 9/1048 |
| 2019/0269157 A1 | 9/2019 | Philippe et al. | | |

FOREIGN PATENT DOCUMENTS

| | | |
|---|---|---|
| EP | 3 034 614 A1 | 6/2016 |
| KR | 2016-0116775 A | 10/2016 |
| WO | WO 2011/153378 A1 | 12/2011 |
| WO | WO 2016/151046 A1 | 9/2016 |
| WO | 2017193010 A1 | 11/2017 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
International Search Report and Written Opinion for International Application No. PCT/US2019/041957, dated Jan. 28, 2020, 16 pages.
Singh et al. Curr Protein Pept Sci. 2007, 18, 1-11 (Year: 2017).
Alignment of SEQ ID No. 102 of US20180223264 to SEQ ID No. 17 (Year: 2018).
Office Action issued in corresponding European Application No. 19837740.0, dated Mar. 21, 2024, 7 pages.

* cited by examiner

*Primary Examiner* — Christian L Fronda
(74) *Attorney, Agent, or Firm* — Morgan, Lewis & Bockius LLP

(57) ABSTRACT

In various aspects and embodiments, the invention provides microbial cells and methods for producing advanced glycosylation products from lower glycosylated intermediates. The microbial cell expresses one or more UDP-dependent glycosyl transferase enzymes in the cytoplasm, for glycosylation of the intermediates. When incubating the microbial strain with a plant extract or fraction thereof comprising the intermediates, these glycosylated intermediates are available for further glycosylation by the cell, and the advanced glycosylation products can be recovered from the media and/or microbial cells.

17 Claims, 8 Drawing Sheets

Specification includes a Sequence Listing.

SEQUENCE LISTING

<160> NUMBER OF SEQ ID NOS: 48

<210> SEQ ID NO 1
<211> LENGTH: 481
<212> TYPE: PRT
<213> ORGANISM: Stevia rebaudiana

<400> SEQUENCE: 1

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365
```

```
Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
            405                 410                 415

Leu Glu Met Gly Thr Lys Val Lys Arg Asp Glu Val Lys Arg Leu Val
            420                 425                 430

Gln Glu Leu Met Gly Glu Gly His Lys Met Arg Asn Lys Ala Lys
            435                 440                 445

Asp Trp Lys Glu Lys Ala Arg Ile Ala Ile Ala Pro Asn Gly Ser Ser
450                 455                 460

Ser Leu Asn Ile Asp Lys Met Val Lys Glu Ile Thr Val Leu Ala Arg
465                 470                 475                 480

Asn

<210> SEQ ID NO 2
<211> LENGTH: 460
<212> TYPE: PRT
<213> ORGANISM: Stevia rebaudiana

<400> SEQUENCE: 2

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
            35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
            115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
            195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255
```

```
Tyr Lys Ala Asn His His Glu Cys Met Asn Trp Leu Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
        290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
                340                 345                 350

Thr His Cys Gly Phe Asn Ser Thr Leu Glu Ala Ile Ser Leu Gly Val
            355                 360                 365

Pro Val Val Ala Met Pro Gln Phe Ser Asp Gln Thr Thr Asn Ala Lys
        370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
                420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
        450                 455                 460

<210> SEQ ID NO 3
<211> LENGTH: 458
<212> TYPE: PRT
<213> ORGANISM: Stevia rebaudiana

<400> SEQUENCE: 3

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175
```

Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
        210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
        290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
        450                 455

<210> SEQ ID NO 4
<211> LENGTH: 485
<212> TYPE: PRT
<213> ORGANISM: Stevia rebaudiana

<400> SEQUENCE: 4

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Phe Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr

```
                    85                  90                  95
Thr Asp Val His Pro Glu Asp Ile Gln Tyr Leu Lys Lys Ala Val Asp
                100                 105                 110

Gly Leu Gln Pro Glu Val Thr Arg Phe Leu Glu Gln His Ser Pro Asp
            115                 120                 125

Trp Ile Ile Tyr Asp Phe Thr His Tyr Trp Leu Pro Ser Ile Ala Ala
        130                 135                 140

Ser Leu Gly Ile Ser Arg Ala Tyr Phe Cys Val Ile Thr Pro Trp Thr
145                 150                 155                 160

Ile Ala Tyr Leu Ala Pro Ser Ser Asp Ala Met Ile Asn Asp Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Met Glu
            195                 200                 205

Pro Tyr Glu Ala Pro Gly Ile Ser Asp Gly Tyr Arg Met Gly Met Val
        210                 215                 220

Phe Lys Gly Ser Asp Cys Leu Leu Phe Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
            260                 265                 270

Thr Trp Val Ser Ile Lys Lys Trp Leu Asp Gly Lys Gln Lys Gly Ser
            275                 280                 285

Val Val Tyr Val Ala Leu Gly Ser Glu Ala Leu Val Ser Gln Thr Glu
        290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
            340                 345                 350

Thr Ser Trp Ala Pro Gln Leu Arg Ile Leu Ser His Glu Ser Val Cys
        355                 360                 365

Gly Phe Leu Thr His Cys Gly Ser Gly Ser Ile Val Glu Gly Leu Met
        370                 375                 380

Phe Gly His Pro Leu Ile Met Leu Pro Ile Phe Cys Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Glu Asn Glu Gly Glu Ile Tyr Lys Ala Asn Ala
        435                 440                 445

Arg Ala Leu Ser Lys Ile Tyr Asn Asp Thr Lys Val Glu Lys Glu Tyr
    450                 455                 460

Val Ser Gln Phe Val Asp Tyr Leu Glu Lys Asn Ala Arg Ala Val Ala
465                 470                 475                 480

Ile Asp His Glu Ser
                485

<210> SEQ ID NO 5
```

```
<211> LENGTH: 473
<212> TYPE: PRT
<213> ORGANISM: Stevia rebaudiana

<400> SEQUENCE: 5
```

| | | | | | | | | | | | | | | |
|---|---|---|---|---|---|---|---|---|---|---|---|---|---|---|
| Met | Ala | Thr | Ser | Asp | Ser | Ile | Val | Asp | Asp | Arg | Lys | Gln | Leu | His | Val |
| 1 | | | | 5 | | | | | 10 | | | | | 15 | |
| Ala | Thr | Phe | Pro | Trp | Leu | Ala | Phe | Gly | His | Ile | Leu | Pro | Tyr | Leu | Gln |
| | | | 20 | | | | | 25 | | | | | 30 | | |
| Leu | Ser | Lys | Leu | Ile | Ala | Glu | Lys | Gly | His | Lys | Val | Ser | Phe | Leu | Ser |
| | | 35 | | | | | 40 | | | | | 45 | | | |
| Thr | Thr | Arg | Asn | Ile | Gln | Arg | Leu | Ser | Ser | His | Ile | Ser | Pro | Leu | Ile |
| | 50 | | | | | 55 | | | | | 60 | | | | |
| Asn | Val | Val | Gln | Leu | Thr | Leu | Pro | Arg | Val | Gln | Glu | Leu | Pro | Glu | Asp |
| 65 | | | | | 70 | | | | | 75 | | | | | 80 |
| Ala | Glu | Ala | Thr | Thr | Asp | Val | His | Pro | Glu | Asp | Ile | Pro | Tyr | Leu | Lys |
| | | | | 85 | | | | | 90 | | | | | 95 | |
| Lys | Ala | Ser | Asp | Gly | Leu | Gln | Pro | Glu | Val | Thr | Arg | Phe | Leu | Glu | Gln |
| | | | 100 | | | | | 105 | | | | | 110 | | |
| His | Ser | Pro | Asp | Trp | Ile | Ile | Tyr | Asp | Tyr | Thr | His | Tyr | Trp | Leu | Pro |
| | | 115 | | | | | 120 | | | | | 125 | | | |
| Ser | Ile | Ala | Ala | Ser | Leu | Gly | Ile | Ser | Arg | Ala | His | Phe | Ser | Val | Thr |
| | 130 | | | | | 135 | | | | | 140 | | | | |
| Thr | Pro | Trp | Ala | Ile | Ala | Tyr | Met | Gly | Pro | Ser | Ala | Asp | Ala | Met | Ile |
| 145 | | | | | 150 | | | | | 155 | | | | | 160 |
| Asn | Gly | Ser | Asp | Gly | Arg | Thr | Thr | Val | Glu | Asp | Leu | Thr | Thr | Pro | Pro |
| | | | | 165 | | | | | 170 | | | | | 175 | |
| Lys | Trp | Phe | Pro | Phe | Pro | Thr | Lys | Val | Cys | Trp | Arg | Lys | His | Asp | Leu |
| | | | 180 | | | | | 185 | | | | | 190 | | |
| Ala | Arg | Leu | Val | Pro | Tyr | Lys | Ala | Pro | Gly | Ile | Ser | Asp | Gly | Tyr | Arg |
| | | 195 | | | | | 200 | | | | | 205 | | | |
| Met | Gly | Leu | Val | Leu | Lys | Gly | Ser | Asp | Cys | Leu | Leu | Ser | Lys | Cys | Tyr |
| | 210 | | | | | 215 | | | | | 220 | | | | |
| His | Glu | Phe | Gly | Thr | Gln | Trp | Leu | Pro | Leu | Leu | Glu | Thr | Leu | His | Gln |
| 225 | | | | | 230 | | | | | 235 | | | | | 240 |
| Val | Pro | Val | Val | Pro | Val | Gly | Leu | Leu | Pro | Pro | Glu | Val | Pro | Gly | Asp |
| | | | | 245 | | | | | 250 | | | | | 255 | |
| Glu | Lys | Asp | Glu | Thr | Trp | Val | Ser | Ile | Lys | Lys | Trp | Leu | Asp | Gly | Lys |
| | | | 260 | | | | | 265 | | | | | 270 | | |
| Gln | Lys | Gly | Ser | Val | Val | Tyr | Val | Ala | Leu | Gly | Ser | Glu | Val | Leu | Val |
| | | 275 | | | | | 280 | | | | | 285 | | | |
| Ser | Gln | Thr | Glu | Val | Val | Glu | Leu | Ala | Leu | Gly | Leu | Glu | Leu | Ser | Gly |
| | 290 | | | | | 295 | | | | | 300 | | | | |
| Leu | Pro | Phe | Val | Trp | Ala | Tyr | Arg | Lys | Pro | Lys | Gly | Pro | Ala | Lys | Ser |
| 305 | | | | | 310 | | | | | 315 | | | | | 320 |
| Asp | Ser | Val | Glu | Leu | Pro | Asp | Gly | Phe | Val | Glu | Arg | Thr | Arg | Asp | Arg |
| | | | | 325 | | | | | 330 | | | | | 335 | |
| Gly | Leu | Val | Trp | Thr | Ser | Trp | Ala | Pro | Gln | Leu | Arg | Ile | Leu | Ser | His |
| | | | 340 | | | | | 345 | | | | | 350 | | |
| Glu | Ser | Val | Cys | Gly | Phe | Leu | Thr | His | Cys | Gly | Ser | Gly | Ser | Ile | Val |
| | | 355 | | | | | 360 | | | | | 365 | | | |
| Glu | Gly | Leu | Met | Phe | Gly | His | Pro | Leu | Ile | Met | Leu | Pro | Ile | Phe | Gly |
| | 370 | | | | | 375 | | | | | 380 | | | | |
| Asp | Gln | Pro | Leu | Asn | Ala | Arg | Leu | Leu | Glu | Asp | Lys | Gln | Val | Gly | Ile |

```
        385                 390                 395                 400
Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
                435                 440                 445

Glu Lys Glu Tyr Val Ser Gln Phe Val Asp Tyr Leu Glu Lys Asn Thr
            450                 455                 460

Arg Ala Val Ala Ile Asp His Glu Ser
465                 470

<210> SEQ ID NO 6
<211> LENGTH: 473
<212> TYPE: PRT
<213> ORGANISM: Stevia rebaudiana

<400> SEQUENCE: 6

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285
```

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
                340                 345                 350

Glu Ser Val Cys Gly Phe Leu Thr His Cys Gly Ser Gly Ser Ile Val
                355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
                420                 425                 430

Lys Ala Asn Ala Arg Glu Leu Ser Lys Ile Tyr Asn Asp Thr Lys Val
                435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470

<210> SEQ ID NO 7
<211> LENGTH: 462
<212> TYPE: PRT
<213> ORGANISM: Oryza sativa

<400> SEQUENCE: 7

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
                35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
                100                 105                 110

Phe Ser Glu Phe Leu Gly Thr Ala Cys Ala Asp Trp Val Ile Val Asp
                115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
                180                 185                 190

Leu Ile Arg Thr Lys Gly Ser Ser Gly Met Ser Leu Ala Glu Arg Phe
            195                 200                 205

Ser Leu Thr Leu Ser Arg Ser Ser Leu Val Val Gly Arg Ser Cys Val
        210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
            245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
            290                 295                 300

Phe Leu Trp Ala Leu Arg Lys Pro Thr Gly Val Ser Asp Ala Asp Leu
305                 310                 315                 320

Leu Pro Ala Gly Phe Glu Arg Thr Arg Gly Arg Gly Val Val Ala
            325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
            355                 360                 365

Phe Gly His Pro Leu Ile Met Leu Pro Ile Phe Gly Asp Gln Gly Pro
370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
            405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
            435                 440                 445

Tyr Ile Asp Gly Phe Ile Gln Gln Leu Arg Ser Tyr Lys Asp
            450                 455                 460

<210> SEQ ID NO 8
<211> LENGTH: 463
<212> TYPE: PRT
<213> ORGANISM: Artificial Sequence
<220> FEATURE:
<223> OTHER INFORMATION: Synthetic Sequences

<400> SEQUENCE: 8

Met Ala Glu Cys Met Asn Trp Leu Asp Asp Lys Pro Lys Glu Ser Val
1               5                   10                  15

Val Tyr Val Ala Phe Gly Ser Leu Val Lys His Gly Pro Glu Gln Val
            20                  25                  30

Glu Glu Ile Thr Arg Ala Leu Ile Asp Ser Asp Val Asn Phe Leu Trp
        35                  40                  45

Val Ile Lys His Lys Glu Gly Lys Leu Pro Glu Asn Leu Ser Glu
    50                  55                  60

Val Ile Lys Thr Gly Lys Gly Leu Ile Val Ala Trp Cys Lys Gln Leu
65                  70                  75                  80

Asp Val Leu Ala His Glu Ser Val Gly Cys Phe Val Thr His Cys Gly
            85                  90                  95

```
Phe Asn Ser Thr Leu Glu Ala Ile Ser Leu Gly Val Pro Val Val Ala
                100                 105                 110

Met Pro Gln Phe Ser Asp Gln Thr Thr Asn Ala Lys Leu Leu Asp Glu
            115                 120                 125

Ile Leu Gly Val Gly Val Arg Val Lys Ala Asp Glu Asn Gly Ile Val
130                 135                 140

Arg Arg Gly Asn Leu Ala Ser Cys Ile Lys Met Ile Met Glu Glu Glu
145                 150                 155                 160

Arg Gly Val Ile Ile Arg Lys Asn Ala Val Lys Trp Lys Asp Leu Ala
                165                 170                 175

Lys Val Ala Val His Glu Gly Gly Ser Ser Asp Asn Asp Ile Val Glu
            180                 185                 190

Phe Val Ser Glu Leu Ile Lys Ala Gly Ser Gly Glu Gln Gln Lys Ile
        195                 200                 205

Lys Lys Ser Pro His Val Leu Leu Ile Pro Phe Pro Leu Gln Gly His
210                 215                 220

Ile Asn Pro Phe Ile Gln Phe Gly Lys Arg Leu Ile Ser Lys Gly Val
225                 230                 235                 240

Lys Thr Thr Leu Val Thr Thr Ile His Thr Leu Asn Ser Thr Leu Asn
                245                 250                 255

His Ser Asn Thr Thr Thr Thr Ser Ile Glu Ile Gln Ala Ile Ser Asp
            260                 265                 270

Gly Cys Asp Glu Gly Gly Phe Met Ser Ala Gly Glu Ser Tyr Leu Glu
        275                 280                 285

Thr Phe Lys Gln Val Gly Ser Lys Ser Leu Ala Asp Leu Ile Lys Lys
        290                 295                 300

Leu Gln Ser Glu Gly Thr Thr Ile Asp Ala Ile Ile Tyr Asp Ser Met
305                 310                 315                 320

Thr Glu Trp Val Leu Asp Val Ala Ile Glu Phe Gly Ile Asp Gly Gly
                325                 330                 335

Ser Phe Phe Thr Gln Ala Cys Val Val Asn Ser Leu Tyr Tyr His Val
            340                 345                 350

His Lys Gly Leu Ile Ser Leu Pro Leu Gly Glu Thr Val Ser Val Pro
        355                 360                 365

Gly Phe Pro Val Leu Gln Arg Trp Glu Thr Pro Leu Ile Leu Gln Asn
370                 375                 380

His Glu Gln Ile Gln Ser Pro Trp Ser Gln Met Leu Phe Gly Gln Phe
385                 390                 395                 400

Ala Asn Ile Asp Gln Ala Arg Trp Val Phe Thr Asn Ser Phe Tyr Lys
                405                 410                 415

Leu Glu Glu Glu Val Ile Glu Trp Thr Arg Lys Ile Trp Asn Leu Lys
            420                 425                 430

Val Ile Gly Pro Thr Leu Pro Ser Met Tyr Leu Asp Lys Arg Leu Asp
        435                 440                 445

Asp Asp Lys Asp Asn Gly Phe Asn Leu Tyr Lys Ala Asn His His
450                 455                 460

<210> SEQ ID NO 9
<211> LENGTH: 463
<212> TYPE: PRT
<213> ORGANISM: Artificial Sequence
<220> FEATURE:
<223> OTHER INFORMATION: Synthetic sequence

<400> SEQUENCE: 9
```

```
Met Ala Gly Ser Ser Gly Met Ser Leu Ala Glu Arg Phe Ser Leu Thr
1               5                   10                  15

Leu Ser Arg Ser Ser Leu Val Val Gly Arg Ser Cys Val Glu Phe Glu
            20                  25                  30

Pro Glu Thr Val Pro Leu Leu Ser Thr Leu Arg Gly Lys Pro Ile Thr
        35                  40                  45

Phe Leu Gly Leu Met Pro Pro Leu His Glu Gly Arg Arg Glu Asp Gly
50                  55                  60

Glu Asp Ala Thr Val Arg Trp Leu Asp Ala Gln Pro Ala Lys Ser Val
65              70                  75                  80

Val Tyr Val Ala Leu Gly Ser Glu Val Pro Leu Gly Val Glu Lys Val
                85                  90                  95

His Glu Leu Ala Leu Gly Leu Glu Leu Ala Gly Thr Arg Phe Leu Trp
                100                 105                 110

Ala Leu Arg Lys Pro Thr Gly Val Ser Asp Ala Asp Leu Leu Pro Ala
            115                 120                 125

Gly Phe Glu Glu Arg Thr Arg Gly Arg Gly Val Val Ala Thr Arg Trp
        130                 135                 140

Val Pro Gln Met Ser Ile Leu Ala His Ala Ala Val Gly Ala Phe Leu
145                 150                 155                 160

Thr His Cys Gly Trp Asn Ser Thr Ile Glu Gly Leu Met Phe Gly His
                165                 170                 175

Pro Leu Ile Met Leu Pro Ile Phe Gly Asp Gln Gly Pro Asn Ala Arg
                180                 185                 190

Leu Ile Glu Ala Lys Asn Ala Gly Leu Gln Val Ala Arg Asn Asp Gly
            195                 200                 205

Asp Gly Ser Phe Asp Arg Glu Gly Val Ala Ala Ile Arg Ala Val
        210                 215                 220

Ala Val Glu Glu Glu Ser Ser Lys Val Phe Gln Ala Lys Ala Lys Lys
225                 230                 235                 240

Leu Gln Glu Ile Val Ala Asp Met Ala Cys His Glu Arg Tyr Ile Asp
                245                 250                 255

Gly Phe Ile Gln Gln Leu Arg Ser Tyr Lys Asp Ser Gly Tyr Ser
            260                 265                 270

Ser Ser Tyr Ala Ala Ala Ala Gly Met His Val Val Ile Cys Pro Trp
        275                 280                 285

Leu Ala Phe Gly His Leu Leu Pro Cys Leu Asp Leu Ala Gln Arg Leu
        290                 295                 300

Ala Ser Arg Gly His Arg Val Ser Phe Val Ser Thr Pro Arg Asn Ile
305                 310                 315                 320

Ser Arg Leu Pro Pro Val Arg Pro Ala Leu Ala Pro Leu Val Ala Phe
                325                 330                 335

Val Ala Leu Pro Leu Pro Arg Val Glu Gly Leu Pro Asp Gly Ala Glu
            340                 345                 350

Ser Thr Asn Asp Val Pro His Asp Arg Pro Asp Met Val Glu Leu His
        355                 360                 365

Arg Arg Ala Phe Asp Gly Leu Ala Ala Pro Phe Ser Glu Phe Leu Gly
    370                 375                 380

Thr Ala Cys Ala Asp Trp Val Ile Val Asp Val Phe His His Trp Ala
385                 390                 395                 400

Ala Ala Ala Ala Leu Glu His Lys Val Pro Cys Ala Met Met Leu Leu
                405                 410                 415
```

```
Gly Ser Ala His Met Ile Ala Ser Ile Ala Asp Arg Arg Leu Glu Arg
                420                 425                 430

Ala Glu Thr Glu Ser Pro Ala Ala Ala Gly Gln Gly Arg Pro Ala Ala
            435                 440                 445

Ala Pro Thr Phe Glu Val Ala Arg Met Lys Leu Ile Arg Thr Lys
        450                 455                 460

<210> SEQ ID NO 10
<211> LENGTH: 459
<212> TYPE: PRT
<213> ORGANISM: Artificial Sequence
<220> FEATURE:
<223> OTHER INFORMATION: Synthetic sequence

<400> SEQUENCE: 10

Met Ala Asn Trp Gln Ile Leu Lys Glu Ile Leu Gly Lys Met Ile Lys
1               5                   10                  15

Gln Thr Lys Ala Ser Ser Gly Val Ile Trp Asn Ser Phe Lys Glu Leu
            20                  25                  30

Glu Glu Ser Glu Leu Glu Thr Val Ile Arg Glu Ile Pro Ala Pro Ser
        35                  40                  45

Phe Leu Ile Pro Leu Pro Lys His Leu Thr Ala Ser Ser Ser Ser Leu
    50                  55                  60

Leu Asp His Asp Arg Thr Val Phe Gln Trp Leu Asp Gln Gln Pro Pro
65                  70                  75                  80

Ser Ser Val Leu Tyr Val Ser Phe Gly Ser Thr Ser Glu Val Asp Glu
                85                  90                  95

Lys Asp Phe Leu Glu Ile Ala Arg Gly Leu Val Asp Ser Lys Gln Ser
            100                 105                 110

Phe Leu Trp Val Val Arg Pro Gly Phe Val Lys Gly Ser Thr Trp Val
        115                 120                 125

Glu Pro Leu Pro Asp Gly Phe Leu Gly Glu Arg Gly Arg Ile Val Lys
    130                 135                 140

Trp Val Pro Gln Gln Glu Val Leu Ala His Gly Ala Ile Gly Ala Phe
145                 150                 155                 160

Trp Thr His Ser Gly Trp Asn Ser Thr Leu Glu Ser Val Cys Glu Gly
                165                 170                 175

Val Pro Met Ile Phe Ser Asp Phe Gly Leu Asp Gln Pro Leu Asn Ala
            180                 185                 190

Arg Tyr Met Ser Asp Val Leu Lys Val Gly Val Tyr Leu Glu Asn Gly
        195                 200                 205

Trp Glu Arg Gly Glu Ile Ala Asn Ala Ile Arg Arg Val Met Val Asp
    210                 215                 220

Glu Glu Gly Glu Tyr Ile Arg Gln Asn Ala Arg Val Leu Lys Gln Lys
225                 230                 235                 240

Ala Asp Val Ser Leu Met Lys Gly Gly Ser Ser Tyr Glu Ser Leu Glu
                245                 250                 255

Ser Leu Val Ser Tyr Ile Ser Ser Leu Glu Asn Lys Thr Glu Thr Thr
            260                 265                 270

Val Arg Arg Arg Arg Arg Ile Ile Leu Phe Pro Val Pro Phe Gln Gly
        275                 280                 285

His Ile Asn Pro Ile Leu Gln Leu Ala Asn Val Leu Tyr Ser Lys Gly
    290                 295                 300

Phe Ser Ile Thr Ile Phe His Thr Asn Phe Asn Lys Pro Lys Thr Ser
305                 310                 315                 320
```

Asn Tyr Pro His Phe Thr Phe Arg Phe Ile Leu Asp Asn Asp Pro Gln
            325                 330                 335

Asp Glu Arg Ile Ser Asn Leu Pro Thr His Gly Pro Leu Ala Gly Met
        340                 345                 350

Arg Ile Pro Ile Ile Asn Glu His Gly Ala Asp Glu Leu Arg Arg Glu
    355                 360                 365

Leu Glu Leu Leu Met Leu Ala Ser Glu Glu Asp Glu Glu Val Ser Cys
370                 375                 380

Leu Ile Thr Asp Ala Leu Trp Tyr Phe Ala Gln Ser Val Ala Asp Ser
385                 390                 395                 400

Leu Asn Leu Arg Arg Leu Val Leu Met Thr Ser Ser Leu Phe Asn Phe
                405                 410                 415

His Ala His Val Ser Leu Pro Gln Phe Asp Glu Leu Gly Tyr Leu Asp
            420                 425                 430

Pro Asp Asp Lys Thr Arg Leu Glu Glu Gln Ala Ser Gly Phe Pro Met
        435                 440                 445

Leu Lys Val Lys Asp Ile Lys Ser Ala Tyr Ser
    450                 455

<210> SEQ ID NO 11
<211> LENGTH: 463
<212> TYPE: PRT
<213> ORGANISM: Artificial Sequence
<220> FEATURE:
<223> OTHER INFORMATION: Synthetic sequence

<400> SEQUENCE: 11

Met Ala Thr Lys Gly Ser Ser Gly Met Ser Leu Ala Glu Arg Phe Trp
1               5                   10                  15

Leu Thr Leu Ser Arg Ser Ser Leu Val Val Gly Arg Ser Cys Val Glu
                20                  25                  30

Phe Glu Pro Glu Thr Val Pro Leu Leu Ser Thr Leu Arg Gly Lys Pro
            35                  40                  45

Ile Thr Phe Leu Gly Leu Met Pro Pro Leu His Glu Gly Arg Arg Glu
        50                  55                  60

Asp Gly Glu Asp Ala Thr Val Arg Trp Leu Asp Ala Gln Pro Ala Lys
65                  70                  75                  80

Ser Val Val Tyr Val Ala Leu Gly Ser Glu Val Pro Leu Gly Val Glu
                85                  90                  95

Lys Val His Glu Leu Ala Leu Gly Leu Glu Leu Ala Gly Thr Arg Phe
            100                 105                 110

Leu Trp Ala Leu Arg Lys Pro Thr Gly Val Ser Asp Ala Asp Leu Leu
        115                 120                 125

Pro Ala Gly Phe Glu Glu Arg Thr Arg Gly Arg Gly Val Val Ala Thr
    130                 135                 140

Arg Trp Val Pro Gln Met Ser Ile Leu Ala His Ala Ala Val Gly Ala
145                 150                 155                 160

Phe Leu Thr His Cys Gly Trp Asn Ser Thr Ile Glu Gly Leu Met Phe
                165                 170                 175

Gly His Pro Leu Ile Met Leu Pro Ile Phe Gly Asp Gln Gly Pro Asn
            180                 185                 190

Ala Arg Leu Ile Glu Ala Lys Asn Ala Gly Leu Gln Val Ala Arg Asn
        195                 200                 205

Asp Gly Asp Gly Ser Phe Asp Arg Glu Gly Val Ala Ala Ala Ile Arg
    210                 215                 220

Ala Val Ala Val Glu Glu Ser Ser Lys Val Phe Gln Ala Lys Ala
225                 230                 235                 240

Lys Lys Leu Gln Glu Ile Val Ala Asp Met Ala Cys His Glu Arg Tyr
            245                 250                 255

Ile Asp Gly Phe Ile Gln Gln Leu Arg Ser Tyr Lys Asp Asp Ser Gly
                260                 265                 270

Tyr Ser Ser Ser Tyr Ala Ala Ala Gly Met His Val Val Ile Cys
            275                 280                 285

Pro Trp Leu Ala Phe Gly His Leu Leu Pro Cys Leu Asp Leu Ala Gln
290                 295                 300

Arg Leu Ala Ser Arg Gly His Arg Val Ser Phe Val Ser Thr Pro Arg
305                 310                 315                 320

Asn Ile Ser Arg Leu Pro Pro Val Arg Pro Ala Leu Ala Pro Leu Val
                325                 330                 335

Ala Phe Val Ala Leu Pro Leu Pro Arg Val Glu Gly Leu Pro Asp Gly
                340                 345                 350

Ala Glu Ser Thr Asn Asp Val Pro His Asp Arg Pro Asp Met Val Glu
            355                 360                 365

Leu His Arg Arg Ala Phe Asp Gly Leu Ala Ala Pro Phe Ser Glu Phe
370                 375                 380

Leu Gly Thr Ala Cys Ala Asp Trp Val Ile Val Asp Val Phe His His
385                 390                 395                 400

Trp Ala Ala Ala Ala Leu Glu His Lys Val Pro Cys Ala Met Met
                405                 410                 415

Leu Leu Gly Ser Ala Glu Met Ile Ala Ser Ile Ala Asp Glu Arg Leu
            420                 425                 430

Glu His Ala Glu Thr Glu Ser Pro Ala Ala Gly Gln Gly Arg Pro
            435                 440                 445

Ala Ala Ala Pro Thr Phe Glu Val Ala Arg Met Lys Leu Ile Arg
450                 455                 460

<210> SEQ ID NO 12
<211> LENGTH: 463
<212> TYPE: PRT
<213> ORGANISM: Artificial Sequence
<220> FEATURE:
<223> OTHER INFORMATION: Synthetic sequence

<400> SEQUENCE: 12

Met Ala Asn His His Glu Cys Met Asn Trp Leu Asp Asp Lys Pro Lys
1               5                   10                  15

Glu Ser Val Val Tyr Val Ala Phe Gly Ser Leu Val Lys His Gly Pro
                20                  25                  30

Glu Gln Val Glu Glu Ile Thr Arg Ala Leu Ile Asp Ser Asp Val Asn
            35                  40                  45

Phe Leu Trp Val Ile Lys His Lys Glu Glu Gly Lys Leu Pro Glu Asn
50                  55                  60

Leu Ser Glu Val Ile Lys Thr Gly Lys Gly Leu Ile Val Ala Trp Cys
65                  70                  75                  80

Lys Gln Leu Asp Val Leu Ala His Glu Ser Val Gly Cys Phe Val Thr
                85                  90                  95

His Cys Gly Phe Asn Ser Thr Leu Glu Ala Ile Ser Leu Gly Val Pro
            100                 105                 110

Val Val Ala Met Pro Gln Phe Ser Asp Gln Thr Thr Asn Ala Lys Leu
        115                 120                 125

```
Leu Asp Glu Ile Leu Gly Val Gly Val Arg Val Lys Ala Asp Glu Asn
    130                 135                 140

Gly Ile Val Arg Arg Gly Asn Leu Ala Ser Cys Ile Lys Met Ile Met
145                 150                 155                 160

Glu Glu Glu Arg Gly Val Ile Ile Arg Lys Asn Ala Val Lys Trp Lys
                165                 170                 175

Asp Leu Ala Lys Val Ala Val His Glu Gly Ser Ser Asp Asn Asp
            180                 185                 190

Ile Val Glu Phe Val Ser Glu Leu Ile Lys Ala Gly Ser Gly Glu Gln
                195                 200                 205

Gln Lys Ile Lys Ser Pro His Val Leu Leu Ile Pro Phe Pro Leu
    210                 215                 220

Gln Gly His Ile Asn Pro Phe Ile Gln Phe Gly Lys Arg Leu Ile Ser
225                 230                 235                 240

Lys Gly Val Lys Thr Thr Leu Val Thr Thr Ile His Thr Leu Asn Ser
                245                 250                 255

Thr Leu Asn His Ser Asn Thr Thr Thr Thr Ser Ile Glu Ile Gln Ala
                260                 265                 270

Ile Ser Asp Gly Cys Asp Glu Gly Gly Phe Met Ser Ala Gly Glu Ser
    275                 280                 285

Tyr Leu Glu Thr Phe Lys Gln Val Gly Ser Lys Ser Leu Ala Asp Leu
    290                 295                 300

Ile Lys Lys Leu Gln Ser Glu Gly Thr Thr Ile Asp Ala Ile Ile Tyr
305                 310                 315                 320

Asp Ser Met Thr Glu Trp Val Leu Asp Val Ala Ile Glu Phe Gly Ile
                325                 330                 335

Asp Gly Gly Ser Phe Phe Thr Gln Ala Cys Val Val Asn Ser Leu Tyr
            340                 345                 350

Tyr His Val His Lys Gly Leu Ile Ser Leu Pro Leu Gly Glu Thr Val
        355                 360                 365

Ser Val Pro Gly Phe Pro Val Leu Gln Arg Trp Glu Thr Pro Leu Ile
    370                 375                 380

Leu Gln Asn His Glu Gln Ile Gln Ser Pro Trp Ser Gln Met Leu Phe
385                 390                 395                 400

Gly Gln Phe Ala Asn Ile Asp Gln Ala Arg Trp Val Phe Thr Asn Ser
                405                 410                 415

Phe Tyr Lys Leu Glu Glu Glu Val Ile Glu Trp Thr Arg Lys Ile Trp
            420                 425                 430

Asn Leu Lys Val Ile Gly Pro Thr Leu Pro Ser Met Tyr Leu Asp Lys
        435                 440                 445

Arg Leu Asp Asp Asp Lys Asp Asn Gly Phe Asn Leu Tyr Lys Ala
    450                 455                 460

<210> SEQ ID NO 13
<211> LENGTH: 482
<212> TYPE: PRT
<213> ORGANISM: Stevia rebaudiana

<400> SEQUENCE: 13

Met Ala Asp Ala Met Ala Thr Thr Glu Lys Lys Pro His Val Ile Phe
1               5                   10                  15

Ile Pro Phe Pro Ala Gln Ser His Ile Lys Ala Met Leu Lys Leu Ala
                20                  25                  30

Gln Leu Leu His His Lys Gly Leu Gln Ile Thr Phe Val Asn Thr Asp
            35                  40                  45
```

```
Phe Ile His Asn Gln Phe Leu Glu Ser Ser Gly Pro His Cys Leu Asp
 50                  55                  60
Gly Ala Pro Gly Phe Arg Phe Glu Thr Ile Pro Asp Gly Val Ser His
 65                  70                  75                   80
Ser Pro Glu Ala Ser Ile Pro Ile Arg Glu Ser Leu Leu Arg Ser Ile
                     85                  90                  95
Glu Thr Asn Phe Leu Asp Arg Phe Ile Asp Leu Val Thr Lys Leu Pro
                100                 105                 110
Asp Pro Pro Thr Cys Ile Ile Ser Asp Gly Phe Leu Ser Val Phe Thr
                115                 120                 125
Ile Asp Ala Ala Lys Lys Leu Gly Ile Pro Val Met Met Tyr Trp Thr
130                 135                 140
Leu Ala Ala Cys Gly Phe Met Gly Phe Tyr His Ile His Ser Leu Ile
145                 150                 155                 160
Glu Lys Gly Phe Ala Pro Leu Lys Asp Ala Ser Tyr Leu Thr Asn Gly
                165                 170                 175
Tyr Leu Asp Thr Val Ile Asp Trp Val Pro Gly Met Glu Gly Ile Arg
                180                 185                 190
Leu Lys Asp Phe Pro Leu Asp Trp Ser Thr Asp Leu Asn Asp Lys Val
                195                 200                 205
Leu Met Phe Thr Thr Glu Ala Thr Gln Arg Ser His Lys Val Ser His
210                 215                 220
His Ile Phe His Thr Phe Asp Glu Leu Glu Pro Ser Ile Ile Lys Thr
225                 230                 235                 240
Leu Ser Leu Arg Tyr Asn His Ile Tyr Thr Ile Gly Pro Leu Gln Leu
                245                 250                 255
Leu Leu Asp Gln Ile Pro Glu Glu Lys Lys Gln Thr Gly Ile Thr Ser
                260                 265                 270
Leu His Gly Tyr Ser Leu Val Lys Glu Glu Pro Glu Cys Phe Gln Trp
                275                 280                 285
Leu Gln Ser Lys Glu Pro Asn Ser Val Val Tyr Val Asn Phe Gly Ser
                290                 295                 300
Thr Thr Val Met Ser Leu Glu Asp Met Thr Glu Phe Gly Trp Gly Leu
305                 310                 315                 320
Ala Asn Ser Asn His Tyr Phe Leu Trp Ile Ile Arg Ser Asn Leu Val
                325                 330                 335
Ile Gly Glu Asn Ala Val Leu Pro Pro Glu Leu Glu Glu His Ile Lys
                340                 345                 350
Lys Arg Gly Phe Ile Ala Ser Trp Cys Ser Gln Glu Lys Val Leu Lys
                355                 360                 365
His Pro Ser Val Gly Gly Phe Leu Thr His Cys Gly Trp Gly Ser Thr
370                 375                 380
Ile Glu Ser Leu Ser Ala Gly Val Pro Met Ile Cys Trp Pro Tyr Ser
385                 390                 395                 400
Trp Asp Gln Leu Thr Asn Cys Arg Tyr Ile Cys Lys Glu Trp Glu Val
                405                 410                 415
Gly Leu Glu Met Gly Thr Lys Val Lys Arg Asp Glu Val Lys Arg Leu
                420                 425                 430
Val Gln Glu Leu Met Gly Glu Gly His Lys Met Arg Asn Lys Ala
                435                 440                 445
Lys Asp Trp Lys Glu Lys Ala Arg Ile Ala Ile Ala Pro Asn Gly Ser
450                 455                 460
```

Ser Ser Leu Asn Ile Asp Lys Met Val Lys Glu Ile Thr Val Leu Ala
465                 470                 475                 480

Arg Asn

<210> SEQ ID NO 14
<211> LENGTH: 459
<212> TYPE: PRT
<213> ORGANISM: Stevia rebaudiana

<400> SEQUENCE: 14

Met Ala Glu Asn Lys Thr Glu Thr Thr Val Arg Arg Arg Arg Arg Ile
1               5                   10                  15

Ile Leu Phe Pro Val Pro Phe Gln Gly His Ile Asn Pro Ile Leu Gln
            20                  25                  30

Leu Ala Asn Val Leu Tyr Ser Lys Gly Phe Ser Ile Thr Ile Phe His
        35                  40                  45

Thr Asn Phe Asn Lys Pro Lys Thr Ser Asn Tyr Pro His Phe Thr Phe
    50                  55                  60

Arg Phe Ile Leu Asp Asn Asp Pro Gln Asp Glu Arg Ile Ser Asn Leu
65                  70                  75                  80

Pro Thr His Gly Pro Leu Ala Gly Met Arg Ile Pro Ile Ile Asn Glu
                85                  90                  95

His Gly Ala Asp Glu Leu Arg Arg Glu Leu Glu Leu Leu Met Leu Ala
            100                 105                 110

Ser Glu Glu Asp Glu Glu Val Ser Cys Leu Ile Thr Asp Ala Leu Trp
        115                 120                 125

Tyr Phe Ala Gln Ser Val Ala Asp Ser Leu Asn Leu Arg Arg Leu Val
    130                 135                 140

Leu Met Thr Ser Ser Leu Phe Asn Phe His Ala His Val Ser Leu Pro
145                 150                 155                 160

Gln Phe Asp Glu Leu Gly Tyr Leu Asp Pro Asp Asp Lys Thr Arg Leu
                165                 170                 175

Glu Glu Gln Ala Ser Gly Phe Pro Met Leu Lys Val Lys Asp Ile Lys
            180                 185                 190

Ser Ala Tyr Ser Asn Trp Gln Ile Ala Lys Glu Ile Leu Gly Lys Met
        195                 200                 205

Ile Lys Gln Thr Lys Ala Ser Ser Gly Val Ile Trp Asn Ser Phe Lys
    210                 215                 220

Glu Leu Glu Glu Ser Glu Leu Glu Thr Val Ile Arg Glu Ile Pro Ala
225                 230                 235                 240

Pro Ser Phe Leu Ile Pro Leu Pro Lys His Leu Thr Ala Ser Ser Ser
                245                 250                 255

Ser Leu Leu Asp His Asp Arg Thr Val Phe Gln Trp Leu Asp Gln Gln
            260                 265                 270

Pro Pro Ser Ser Val Leu Tyr Val Ser Phe Gly Ser Thr Ser Glu Val
        275                 280                 285

Asp Glu Lys Asp Phe Leu Glu Ile Ala Arg Gly Leu Val Asp Ser Lys
    290                 295                 300

Gln Ser Phe Leu Trp Val Val Arg Pro Gly Phe Val Lys Gly Ser Thr
305                 310                 315                 320

Trp Val Glu Pro Leu Pro Asp Gly Phe Leu Glu Arg Gly Arg Ile
                325                 330                 335

Val Lys Trp Val Pro Gln Gln Val Leu Ala His Gly Ala Ile Gly
            340                 345                 350

Ala Phe Trp Thr His Ser Gly Trp Asn Ser Thr Leu Glu Ser Val Cys
            355                 360                 365

Glu Gly Val Pro Met Ile Phe Ser Asp Phe Gly Leu Asp Gln Pro Leu
            370                 375                 380

Asn Ala Arg Tyr Met Ser Asp Val Leu Lys Val Gly Val Tyr Leu Glu
385                 390                 395                 400

Asn Gly Trp Glu Arg Gly Glu Ile Ala Asn Ala Ile Arg Arg Val Met
            405                 410                 415

Val Asp Glu Glu Gly Glu Tyr Ile Arg Gln Asn Ala Arg Val Leu Lys
            420                 425                 430

Gln Lys Ala Asp Val Ser Leu Met Lys Gly Gly Ser Ser Tyr Glu Ser
            435                 440                 445

Leu Glu Ser Leu Val Ser Tyr Ile Ser Ser Leu
            450                 455

<210> SEQ ID NO 15
<211> LENGTH: 458
<212> TYPE: PRT
<213> ORGANISM: Artificial Sequence
<220> FEATURE:
<223> OTHER INFORMATION: Synthetic sequence

<400> SEQUENCE: 15

Met Ala Phe Leu Trp Val Val Arg Pro Gly Phe Val Lys Gly Ser Thr
1               5                   10                  15

Trp Val Glu Pro Leu Pro Asp Gly Phe Leu Gly Glu Arg Gly Arg Ile
            20                  25                  30

Val Lys Trp Val Pro Gln Gln Glu Val Leu Ala His Gly Ala Ile Gly
            35                  40                  45

Ala Phe Trp Thr His Gly Gly Trp Asn Ser Thr Leu Glu Ser Val Cys
50                  55                  60

Glu Gly Val Pro Met Ile Phe Ser Asp Phe Gly Leu Asp Gln Pro Leu
65                  70                  75                  80

Asn Ala Arg Tyr Met Ser Asp Val Leu Lys Val Gly Val Tyr Leu Glu
            85                  90                  95

Asn Gly Trp Glu Arg Gly Glu Ile Ala Asn Ala Ile Arg Arg Leu Met
            100                 105                 110

Val Asp Glu Glu Gly Glu Tyr Ile Arg Gln Asn Ala Arg Val Leu Lys
            115                 120                 125

Gln Lys Ala Asp Val Ser Leu Met Lys Gly Gly Ser Ser Tyr Glu Ser
            130                 135                 140

Leu Glu Ser Leu Val Ser Tyr Ile Ser Ser Leu Gly Ser Gly Gly Ser
145                 150                 155                 160

Gly Gly Ser Gly Arg Arg Arg Ile Ile Leu Phe Pro Val Pro Phe
            165                 170                 175

Gln Gly His Ile Asn Pro Met Leu Gln Leu Ala Asn Val Leu Tyr Ser
            180                 185                 190

Lys Gly Phe Ser Ile Thr Ile Phe His Thr Asn Phe Asn Lys Pro Lys
            195                 200                 205

Thr Ser Asn Tyr Pro His Phe Thr Phe Arg Phe Ile Leu Asp Asn Asp
            210                 215                 220

Pro Gln Asp Glu Arg Ile Ser Asn Leu Pro Thr His Gly Pro Leu Ala
225                 230                 235                 240

Gly Met Arg Ile Pro Ile Ile Asn Glu His Gly Ala Asp Glu Leu Arg
            245                 250                 255

```
Arg Glu Leu Glu Leu Met Leu Ala Ser Gly Asp Glu Val
            260                 265                 270

Ser Cys Leu Ile Thr Asp Ala Leu Trp Tyr Phe Ala Gln Ser Val Ala
        275                 280                 285

Asp Ser Leu Asn Leu Arg Arg Leu Val Leu Met Thr Ser Ser Leu Phe
        290                 295                 300

Asn Phe His Ala His Val Ser Leu Pro Gln Phe Asp Glu Leu Gly Tyr
305                 310                 315                 320

Leu Asp Pro Asp Lys Thr Arg Leu Glu Glu Gln Ala Ser Gly Phe
                325                 330                 335

Pro Met Leu Lys Val Lys Asp Ile Lys Ser Ala Tyr Ser Asn Trp Gln
        340                 345                 350

Ile Ala Lys Glu Ile Leu Gly Lys Met Ile Lys Gln Thr Lys Ala Ser
        355                 360                 365

Ser Gly Val Ile Trp Asn Ser Phe Lys Glu Leu Glu Glu Ser Glu Leu
        370                 375                 380

Glu Thr Val Ile Arg Glu Ile Pro Ala Pro Ser Phe Leu Ile Pro Leu
385                 390                 395                 400

Pro Lys His Leu Thr Ala Ser Ser Ser Ser Leu Leu Asp His Asp Arg
        405                 410                 415

Thr Val Phe Gln Trp Leu Asp Gln Gln Pro Ser Ser Val Leu Tyr
                420                 425                 430

Val Ser Phe Gly Ser Thr Ser Glu Val Asp Glu Lys Asp Phe Leu Glu
        435                 440                 445

Ile Ala Arg Gly Leu Val Asp Ser Gln Ser
450                 455

<210> SEQ ID NO 16
<211> LENGTH: 451
<212> TYPE: PRT
<213> ORGANISM: Artificial Sequence
<220> FEATURE:
<223> OTHER INFORMATION: Synthetic sequence

<400> SEQUENCE: 16

Met Ala Phe Leu Trp Val Val Arg Pro Gly Phe Val Lys Gly Ser Thr
1               5                   10                  15

Trp Val Glu Pro Leu Pro Asp Gly Phe Leu Gly Glu Arg Gly Arg Ile
            20                  25                  30

Val Lys Trp Val Pro Gln Gln Glu Val Leu Ala His Gly Ala Ile Gly
        35                  40                  45

Ala Phe Trp Thr His Gly Gly Trp Asn Ser Thr Leu Glu Ser Val Cys
    50                  55                  60

Glu Gly Val Pro Met Ile Phe Ser Asp Phe Gly Leu Asp Gln Pro Leu
65                  70                  75                  80

Asn Ala Arg Tyr Met Ser Asp Val Leu Lys Val Gly Val Tyr Leu Glu
                85                  90                  95

Asn Gly Trp Glu Arg Gly Glu Ile Ala Asn Ala Ile Arg Arg Leu Met
            100                 105                 110

Val Asp Glu Glu Gly Glu Tyr Ile Arg Gln Asn Ala Arg Val Leu Lys
        115                 120                 125

Gln Lys Ala Asp Val Ser Leu Met Lys Gly Gly Ser Ser Tyr Glu Ser
    130                 135                 140

Leu Glu Ser Leu Val Ser Tyr Ile Ser Ser Leu Gly Ser Gly Gly Ser
145                 150                 155                 160
```

```
Gly Gly Ser Gly Arg Arg Arg Ile Ile Leu Phe Pro Val Pro Phe
            165                 170                 175

Gln Gly His Ile Asn Pro Met Leu Gln Leu Ala Asn Val Leu Tyr Ser
            180                 185                 190

Lys Gly Phe Ser Ile Thr Ile Phe His Thr Asn Phe Asn Lys Pro Lys
            195                 200                 205

Thr Ser Asn Tyr Pro His Phe Thr Phe Arg Phe Ile Leu Asp Asn Asp
    210                 215                 220

Pro Gln Thr Thr His Gly Pro Leu Ala Gly Met Arg Ile Pro Ile Ile
225                 230                 235                 240

Asn Glu His Gly Ala Asp Glu Leu Arg Arg Glu Leu Glu Leu Gln Met
            245                 250                 255

Leu Ala Ser Glu Glu Asp Glu Val Ser Cys Leu Ile Thr Asp Ala
            260                 265                 270

Leu Trp Tyr Phe Ala Gln Ser Val Ala Asp Ser Leu Asn Leu Pro Arg
            275                 280                 285

Leu Val Leu Met Thr Ser Ser Leu Phe Asn Phe His Ala His Val Ser
            290                 295                 300

Leu Pro Gln Phe Asp Glu Leu Gly Tyr Leu Asp Pro Asp Lys Thr
305                 310                 315                 320

Arg Leu Glu Glu Gln Ala Ser Gly Phe Pro Met Leu Lys Val Lys Asp
            325                 330                 335

Ile Lys Ser Ala Tyr Ser Asn Trp Gln Ile Ala Lys Glu Ile Leu Gly
            340                 345                 350

Lys Met Ile Lys Gln Thr Lys Ala Ser Ser Gly Val Ile Trp Asn Ser
            355                 360                 365

Phe Lys Glu Leu Glu Glu Ser Glu Leu Glu Thr Val Ile Arg Glu Ile
            370                 375                 380

Pro Ala Pro Ser Phe Leu Ile Pro Leu Pro Lys His Leu Thr Ala Ser
385                 390                 395                 400

Ser Ser Ser Leu Leu Asp His Asp Arg Thr Val Phe Gln Trp Leu Asp
            405                 410                 415

Gln Gln Pro Pro Ser Ser Val Leu Tyr Val Ser Phe Gly Ser Thr Ser
            420                 425                 430

Glu Val Asp Glu Lys Asp Phe Leu Glu Ile Ala Arg Gly Leu Val Asp
            435                 440                 445

Ser Gln Ser
    450

<210> SEQ ID NO 17
<211> LENGTH: 455
<212> TYPE: PRT
<213> ORGANISM: Artificial Sequence
<220> FEATURE:
<223> OTHER INFORMATION: Synthetic sequence

<400> SEQUENCE: 17

Met Ala Phe Leu Trp Val Val Arg Pro Gly Phe Val Lys Gly Ser Thr
1               5                   10                  15

Trp Val Glu Pro Leu Pro Asp Gly Phe Leu Gly Glu Arg Gly Arg Ile
            20                  25                  30

Val Lys Trp Val Pro Gln Gln Glu Val Leu Ala His Gly Ala Ile Gly
            35                  40                  45

Ala Phe Trp Thr His Gly Gly Trp Asn Ser Thr Leu Glu Ser Val Cys
    50                  55                  60
```

Glu Gly Val Pro Met Ile Phe Ser Asp Phe Gly Leu Asp Gln Pro Leu
 65                  70                  75                  80

Asn Ala Arg Tyr Met Ser Asp Val Leu Lys Val Gly Tyr Leu Glu
             85                  90                  95

Asn Gly Trp Glu Arg Gly Glu Ile Ala Asn Ala Ile Arg Arg Leu Met
            100                 105                 110

Val Asp Glu Glu Gly Glu Tyr Ile Arg Gln Asn Ala Arg Val Leu Lys
            115                 120                 125

Gln Lys Ala Asp Val Ser Leu Met Lys Gly Gly Ser Tyr Glu Ser
            130                 135                 140

Leu Glu Ser Leu Val Ser Tyr Ile Ser Ser Leu Gly Ser Gly Gly Ser
145                 150                 155                 160

Gly Arg Arg Arg Arg Ile Ile Leu Phe Pro Val Pro Phe Gln Gly His
                165                 170                 175

Ile Asn Pro Met Leu Gln Leu Ala Asn Val Leu Tyr Ser Lys Gly Phe
            180                 185                 190

Ser Ile Thr Ile Phe His Thr Asn Phe Asn Lys Pro Lys Thr Ser Asn
            195                 200                 205

Tyr Pro His Phe Thr Phe Arg Phe Ile Leu Asp Asn Asp Pro Gln Asp
210                 215                 220

Glu Arg Ile Ser Asn Leu Pro Thr His Gly Pro Leu Ala Gly Met Arg
225                 230                 235                 240

Ile Pro Ile Ile Asn Glu His Gly Ala Asp Glu Leu Arg Arg Glu Leu
                245                 250                 255

Glu Leu Gln Met Leu Ala Ser Glu Glu Asp Glu Glu Val Ser Cys Leu
            260                 265                 270

Ile Thr Asp Ala Leu Trp Tyr Phe Ala Gln Ser Val Ala Asp Ser Leu
            275                 280                 285

Asn Leu Pro Arg Leu Val Leu Met Thr Ser Ser Leu Phe Asn Phe His
            290                 295                 300

Ala His Val Ser Leu Pro Gln Phe Asp Glu Leu Gly Tyr Leu Asp Pro
305                 310                 315                 320

Asp Asp Lys Thr Arg Leu Glu Glu Gln Ala Ser Gly Phe Pro Met Leu
            325                 330                 335

Lys Val Lys Asp Ile Lys Ser Ala Tyr Ser Asn Trp Gln Ile Ala Lys
            340                 345                 350

Glu Ile Leu Gly Lys Met Ile Lys Gln Thr Lys Ala Ser Ser Gly Val
            355                 360                 365

Ile Trp Asn Ser Phe Lys Glu Leu Glu Glu Ser Glu Leu Glu Thr Val
            370                 375                 380

Ile Arg Glu Ile Pro Ala Pro Ser Phe Leu Ile Pro Leu Pro Lys His
385                 390                 395                 400

Leu Thr Ala Ser Ser Ser Leu Leu Glu His Asp Arg Thr Val Phe
            405                 410                 415

Gln Trp Leu Asp Gln Pro Pro Ser Ser Val Leu Tyr Val Ser Phe
            420                 425                 430

Gly Ser Thr Ser Glu Val Asp Glu Lys Asp Phe Leu Glu Ile Ala Arg
            435                 440                 445

Gly Leu Val Asp Ser Gln Ser
            450                 455

<210> SEQ ID NO 18
<211> LENGTH: 523
<212> TYPE: PRT

<213> ORGANISM: Siraitia grosvenorii

<400> SEQUENCE: 18

```
Met Glu Asp Arg Asn Ala Met Asp Met Ser Arg Ile Lys Tyr Arg Pro
1               5                   10                  15

Gln Pro Leu Arg Pro Ala Ser Met Val Gln Pro Arg Val Leu Leu Phe
            20                  25                  30

Pro Phe Pro Ala Leu Gly His Val Lys Pro Phe Leu Ser Leu Ala Glu
        35                  40                  45

Leu Leu Ser Asp Ala Gly Ile Asp Val Val Phe Leu Ser Thr Glu Tyr
    50                  55                  60

Asn His Arg Arg Ile Ser Asn Thr Glu Ala Leu Ala Ser Arg Phe Pro
65                  70                  75                  80

Thr Leu His Phe Glu Thr Ile Pro Asp Gly Leu Pro Pro Asn Glu Ser
                85                  90                  95

Arg Ala Leu Ala Asp Gly Pro Leu Tyr Phe Ser Met Arg Glu Gly Thr
            100                 105                 110

Lys Pro Arg Phe Arg Gln Leu Ile Gln Ser Leu Asn Asp Gly Arg Trp
        115                 120                 125

Pro Ile Thr Cys Ile Ile Thr Asp Ile Met Leu Ser Ser Pro Ile Glu
    130                 135                 140

Val Ala Glu Glu Phe Gly Ile Pro Val Ile Ala Phe Cys Pro Cys Ser
145                 150                 155                 160

Ala Arg Tyr Leu Ser Ile His Phe Phe Ile Pro Lys Leu Val Glu Glu
                165                 170                 175

Gly Gln Ile Pro Tyr Ala Asp Asp Pro Ile Gly Glu Ile Gln Gly
            180                 185                 190

Val Pro Leu Phe Glu Gly Leu Leu Arg Arg Asn His Leu Pro Gly Ser
        195                 200                 205

Trp Ser Asp Lys Ser Ala Asp Ile Ser Phe Ser His Gly Leu Ile Asn
    210                 215                 220

Gln Thr Leu Ala Ala Gly Arg Ala Ser Ala Leu Ile Leu Asn Thr Phe
225                 230                 235                 240

Asp Glu Leu Glu Ala Pro Phe Leu Thr His Leu Ser Ser Ile Phe Asn
                245                 250                 255

Lys Ile Tyr Thr Ile Gly Pro Leu His Ala Leu Ser Lys Ser Arg Leu
            260                 265                 270

Gly Asp Ser Ser Ser Ala Ser Ala Leu Ser Gly Phe Trp Lys Glu
        275                 280                 285

Asp Arg Ala Cys Met Ser Trp Leu Asp Cys Gln Pro Pro Arg Ser Val
    290                 295                 300

Val Phe Val Ser Phe Gly Ser Thr Met Lys Met Lys Ala Asp Glu Leu
305                 310                 315                 320

Arg Glu Phe Trp Tyr Gly Leu Val Ser Ser Gly Lys Pro Phe Leu Cys
                325                 330                 335

Val Leu Arg Ser Asp Val Val Ser Gly Gly Glu Ala Ala Glu Leu Ile
            340                 345                 350

Glu Gln Met Ala Glu Glu Glu Gly Ala Gly Lys Leu Gly Met Val
        355                 360                 365

Val Glu Trp Ala Ala Gln Glu Lys Val Leu Ser His Pro Ala Val Gly
    370                 375                 380

Gly Phe Leu Thr His Cys Gly Trp Asn Ser Thr Val Glu Ser Ile Ala
385                 390                 395                 400
```

Ala Gly Val Pro Met Met Cys Trp Pro Ile Leu Gly Asp Gln Pro Ser
            405                 410                 415

Asn Ala Thr Trp Ile Asp Arg Val Trp Lys Ile Gly Val Glu Arg Asn
            420                 425                 430

Asn Arg Glu Trp Asp Arg Leu Thr Val Glu Lys Met Val Arg Ala Leu
            435                 440                 445

Met Glu Gly Gln Lys Arg Val Glu Ile Gln Arg Ser Met Glu Lys Leu
450                 455                 460

Ser Lys Leu Ala Asn Glu Lys Val Val Arg Gly Ile Asn Leu His Pro
465                 470                 475                 480

Thr Ile Ser Leu Lys Lys Asp Thr Pro Thr Thr Ser Glu His Pro Arg
            485                 490                 495

His Glu Phe Glu Asn Met Arg Gly Met Asn Tyr Glu Met Leu Val Gly
            500                 505                 510

Asn Ala Ile Lys Ser Pro Thr Leu Thr Lys Lys
            515                 520

<210> SEQ ID NO 19
<211> LENGTH: 473
<212> TYPE: PRT
<213> ORGANISM: Siraitia grosvenorii

<400> SEQUENCE: 19

Met Thr Ile Phe Phe Ser Val Glu Ile Leu Val Leu Gly Ile Ala Glu
1               5                   10                  15

Phe Ala Ala Ile Ala Met Asp Ala Ala Gln Gln Gly Asp Thr Thr Thr
            20                  25                  30

Ile Leu Met Leu Pro Trp Leu Gly Tyr Gly His Leu Ser Ala Phe Leu
            35                  40                  45

Glu Leu Ala Lys Ser Leu Ser Arg Arg Asn Phe His Ile Tyr Phe Cys
        50                  55                  60

Ser Thr Ser Val Asn Leu Asp Ala Ile Lys Pro Lys Leu Pro Ser Ser
65                  70                  75                  80

Phe Ser Asp Ser Ile Gln Phe Val Glu Leu His Leu Pro Ser Ser Pro
                85                  90                  95

Glu Phe Pro Pro His Leu His Thr Thr Asn Gly Leu Pro Pro Thr Leu
            100                 105                 110

Met Pro Ala Leu His Gln Ala Phe Ser Met Ala Ala Gln His Phe Glu
        115                 120                 125

Ser Ile Leu Gln Thr Leu Ala Pro His Leu Leu Ile Tyr Asp Ser Leu
130                 135                 140

Gln Pro Trp Ala Pro Arg Val Ala Ser Ser Leu Lys Ile Pro Ala Ile
145                 150                 155                 160

Asn Phe Asn Thr Thr Gly Val Phe Val Ile Ser Gln Gly Leu His Pro
                165                 170                 175

Ile His Tyr Pro His Ser Lys Phe Pro Phe Ser Glu Phe Val Leu His
            180                 185                 190

Asn His Trp Lys Ala Met Tyr Ser Thr Ala Asp Gly Ala Ser Thr Glu
        195                 200                 205

Arg Thr Arg Lys Arg Gly Glu Ala Phe Leu Tyr Cys Leu His Ala Ser
210                 215                 220

Cys Ser Val Ile Leu Ile Asn Ser Phe Arg Glu Leu Glu Gly Lys Tyr
225                 230                 235                 240

Met Asp Tyr Leu Ser Val Leu Leu Asn Lys Lys Val Val Pro Val Gly
                245                 250                 255

```
Pro Leu Val Tyr Glu Pro Asn Gln Asp Gly Glu Asp Glu Gly Tyr Ser
            260                 265                 270

Ser Ile Lys Asn Trp Leu Asp Lys Glu Pro Ser Ser Thr Val Phe
    275                 280                 285

Val Ser Phe Gly Ser Glu Tyr Phe Pro Ser Lys Glu Glu Met Glu Glu
290                 295                 300

Ile Ala His Gly Leu Glu Ala Ser Glu Val Asn Phe Ile Trp Val Val
305                 310                 315                 320

Arg Phe Pro Gln Gly Asp Asn Thr Ser Gly Ile Glu Asp Ala Leu Pro
                325                 330                 335

Lys Gly Phe Leu Glu Arg Ala Gly Glu Arg Gly Met Val Val Lys Gly
                340                 345                 350

Trp Ala Pro Gln Ala Lys Ile Leu Lys His Trp Ser Thr Gly Gly Phe
                355                 360                 365

Val Ser His Cys Gly Trp Asn Ser Val Met Glu Ser Met Met Phe Gly
                370                 375                 380

Val Pro Ile Ile Gly Val Pro Met His Val Asp Gln Pro Phe Asn Ala
385                 390                 395                 400

Gly Leu Val Glu Glu Ala Gly Val Gly Val Glu Ala Lys Arg Asp Pro
                405                 410                 415

Asp Gly Lys Ile Gln Arg Asp Glu Val Ala Lys Leu Ile Lys Glu Val
                420                 425                 430

Val Val Glu Lys Thr Arg Glu Asp Val Arg Lys Lys Ala Arg Glu Met
                435                 440                 445

Ser Glu Ile Leu Arg Ser Lys Gly Glu Glu Lys Phe Asp Glu Met Val
                450                 455                 460

Ala Glu Ile Ser Leu Leu Leu Lys Ile
465                 470

<210> SEQ ID NO 20
<211> LENGTH: 460
<212> TYPE: PRT
<213> ORGANISM: Siraitia grosvenorii

<400> SEQUENCE: 20

Met Asp Glu Thr Thr Val Asn Gly Gly Arg Arg Ala Ser Asp Val Val
1               5                   10                  15

Val Phe Ala Phe Pro Arg His Gly His Met Ser Pro Met Leu Gln Phe
                20                  25                  30

Ser Lys Arg Leu Val Ser Lys Gly Leu Arg Val Thr Phe Leu Ile Thr
            35                  40                  45

Thr Ser Ala Thr Glu Ser Leu Arg Leu Asn Leu Pro Pro Ser Ser Ser
    50                  55                  60

Leu Asp Leu Gln Val Ile Ser Asp Val Pro Glu Ser Asn Asp Ile Ala
65                  70                  75                  80

Thr Leu Glu Gly Tyr Leu Arg Ser Phe Lys Ala Thr Val Ser Lys Thr
                85                  90                  95

Leu Ala Asp Phe Ile Asp Gly Ile Gly Asn Pro Pro Lys Phe Ile Val
                100                 105                 110

Tyr Asp Ser Val Met Pro Trp Val Gln Glu Val Ala Arg Gly Arg Gly
            115                 120                 125

Leu Asp Ala Ala Pro Phe Phe Thr Gln Ser Ser Ala Val Asn His Ile
130                 135                 140

Leu Asn His Val Tyr Gly Gly Ser Leu Ser Ile Pro Ala Pro Glu Asn
```

```
                145                 150                 155                 160
Thr Ala Val Ser Leu Pro Ser Met Pro Val Leu Gln Ala Glu Asp Leu
                165                 170                 175
Pro Ala Phe Pro Asp Asp Pro Glu Val Val Met Asn Phe Met Thr Ser
                180                 185                 190
Gln Phe Ser Asn Phe Gln Asp Ala Lys Trp Ile Phe Phe Asn Thr Phe
                195                 200                 205
Asp Gln Leu Glu Cys Lys Lys Gln Ser Gln Val Val Asn Trp Met Ala
            210                 215                 220
Asp Arg Trp Pro Ile Lys Thr Val Gly Pro Thr Ile Pro Ser Ala Tyr
225                 230                 235                 240
Leu Asp Asp Gly Arg Leu Glu Asp Arg Ala Phe Gly Leu Asn Leu
                245                 250                 255
Leu Lys Pro Glu Asp Gly Lys Asn Thr Arg Gln Trp Gln Trp Leu Asp
                260                 265                 270
Ser Lys Asp Thr Ala Ser Val Leu Tyr Ile Ser Phe Gly Ser Leu Ala
            275                 280                 285
Ile Leu Gln Glu Glu Gln Val Lys Glu Leu Ala Tyr Phe Leu Lys Asp
        290                 295                 300
Thr Asn Leu Ser Phe Leu Trp Val Leu Arg Asp Ser Glu Leu Gln Lys
305                 310                 315                 320
Leu Pro His Asn Phe Val Gln Glu Thr Ser His Arg Gly Leu Val Val
                325                 330                 335
Asn Trp Cys Ser Gln Leu Gln Val Leu Ser His Arg Ala Val Ser Cys
                340                 345                 350
Phe Val Thr His Cys Gly Trp Asn Ser Thr Leu Glu Ala Leu Ser Leu
                355                 360                 365
Gly Val Pro Met Val Ala Ile Pro Gln Trp Val Asp Gln Thr Thr Asn
            370                 375                 380
Ala Lys Phe Val Ala Asp Val Trp Arg Val Gly Val Arg Val Lys Lys
385                 390                 395                 400
Lys Asp Glu Arg Ile Val Thr Lys Glu Glu Leu Glu Ala Ser Ile Arg
                405                 410                 415
Gln Val Val Gln Gly Glu Gly Arg Asn Glu Phe Lys His Asn Ala Ile
            420                 425                 430
Lys Trp Lys Lys Leu Ala Lys Glu Ala Val Asp Glu Gly Gly Ser Ser
            435                 440                 445
Asp Lys Asn Ile Glu Glu Phe Val Lys Thr Ile Ala
    450                 455                 460

<210> SEQ ID NO 21
<211> LENGTH: 486
<212> TYPE: PRT
<213> ORGANISM: Siraitia grosvenorii

<400> SEQUENCE: 21

Met Gly Asp Asn Gly Asp Gly Gly Glu Lys Lys Glu Leu Lys Glu Asn
1               5                   10                  15
Val Lys Lys Gly Lys Glu Leu Gly Arg Gln Ala Ile Gly Glu Gly Tyr
                20                  25                  30
Ile Asn Pro Ser Leu Gln Leu Ala Arg Arg Leu Ile Ser Leu Gly Val
            35                  40                  45
Asn Val Thr Phe Ala Thr Thr Val Leu Ala Gly Arg Arg Met Lys Asn
        50                  55                  60
```

```
Lys Thr His Gln Thr Ala Thr Thr Pro Gly Leu Ser Phe Ala Thr Phe
 65                  70                  75                  80

Ser Asp Gly Phe Asp Asp Glu Thr Leu Lys Pro Asn Gly Asp Leu Thr
                 85                  90                  95

His Tyr Phe Ser Glu Leu Arg Arg Cys Gly Ser Glu Ser Leu Thr His
            100                 105                 110

Leu Ile Thr Ser Ala Ala Asn Glu Gly Arg Pro Ile Thr Phe Val Ile
        115                 120                 125

Tyr Ser Leu Leu Leu Ser Trp Ala Ala Asp Ile Ala Ser Thr Tyr Asp
    130                 135                 140

Ile Pro Ser Ala Leu Phe Phe Ala Gln Pro Ala Thr Val Leu Ala Leu
145                 150                 155                 160

Tyr Phe Tyr Tyr Phe His Gly Tyr Gly Asp Thr Ile Cys Ser Lys Leu
                165                 170                 175

Gln Asp Pro Ser Ser Tyr Ile Glu Leu Pro Gly Leu Pro Leu Leu Thr
            180                 185                 190

Ser Gln Asp Met Pro Ser Phe Phe Ser Pro Ser Gly Pro His Ala Phe
        195                 200                 205

Ile Leu Pro Pro Met Arg Glu Gln Ala Glu Phe Leu Gly Arg Gln Ser
    210                 215                 220

Gln Pro Lys Val Leu Val Asn Thr Phe Asp Ala Leu Glu Ala Asp Ala
225                 230                 235                 240

Leu Arg Ala Ile Asp Lys Leu Lys Met Leu Ala Ile Gly Pro Leu Ile
                245                 250                 255

Pro Ser Ala Leu Leu Gly Gly Asn Asp Ser Ser Asp Ala Ser Phe Cys
            260                 265                 270

Gly Asp Leu Phe Gln Val Ser Ser Glu Asp Tyr Ile Glu Trp Leu Asn
        275                 280                 285

Ser Lys Pro Asp Ser Ser Val Val Tyr Ile Ser Val Gly Ser Ile Cys
    290                 295                 300

Val Leu Ser Asp Glu Gln Glu Asp Glu Leu Val His Ala Leu Leu Asn
305                 310                 315                 320

Ser Gly His Thr Phe Leu Trp Val Lys Arg Ser Lys Glu Asn Asn Glu
                325                 330                 335

Gly Val Lys Gln Glu Thr Asp Glu Glu Lys Leu Lys Lys Leu Glu Glu
            340                 345                 350

Gln Gly Lys Met Val Ser Trp Cys Arg Gln Val Glu Val Leu Lys His
        355                 360                 365

Pro Ala Leu Gly Cys Phe Leu Thr His Cys Gly Trp Asn Ser Thr Ile
370                 375                 380

Glu Ser Leu Val Ser Gly Leu Pro Val Val Ala Phe Pro Gln Gln Ile
385                 390                 395                 400

Asp Gln Ala Thr Asn Ala Lys Leu Ile Glu Asp Val Trp Lys Thr Gly
                405                 410                 415

Val Arg Val Lys Ala Asn Thr Glu Gly Ile Val Glu Arg Glu Glu Ile
            420                 425                 430

Arg Arg Cys Leu Asp Leu Val Met Gly Ser Arg Asp Gly Gln Lys Glu
        435                 440                 445

Glu Ile Glu Arg Asn Ala Lys Lys Trp Lys Glu Leu Ala Arg Gln Ala
    450                 455                 460

Ile Gly Glu Gly Gly Ser Ser Asp Ser Asn Leu Lys Thr Phe Leu Trp
465                 470                 475                 480

Glu Ile Asp Leu Glu Ile
```

<210> SEQ ID NO 22
<211> LENGTH: 485
<212> TYPE: PRT
<213> ORGANISM: Siraitia grosvenorii

<400> SEQUENCE: 22

```
Met Ala Glu Gln Ala His Asp Leu Leu His Val Leu Phe Pro Phe
1               5                   10                  15

Pro Ala Glu Gly His Ile Lys Pro Phe Leu Cys Leu Ala Glu Leu Leu
            20                  25                  30

Cys Asn Ala Gly Phe His Val Thr Phe Leu Asn Thr Asp Tyr Asn His
            35                  40                  45

Arg Arg Leu His Asn Leu His Leu Leu Ala Ala Arg Phe Pro Ser Leu
        50                  55                  60

His Phe Glu Ser Ile Ser Asp Gly Leu Pro Pro Asp Gln Pro Arg Asp
65              70                  75                  80

Ile Leu Asp Pro Lys Phe Phe Ile Ser Ile Cys Gln Val Thr Lys Pro
                85                  90                  95

Leu Phe Arg Glu Leu Leu Leu Ser Tyr Lys Arg Ile Ser Ser Val Gln
            100                 105                 110

Thr Gly Arg Pro Pro Ile Thr Cys Val Ile Thr Asp Val Ile Phe Arg
        115                 120                 125

Phe Pro Ile Asp Val Ala Glu Glu Leu Asp Ile Pro Val Phe Ser Phe
130             135                 140

Cys Thr Phe Ser Ala Arg Phe Met Phe Leu Tyr Phe Trp Ile Pro Lys
145                 150                 155                 160

Leu Ile Glu Asp Gly Gln Leu Pro Tyr Pro Asn Gly Asn Ile Asn Gln
                165                 170                 175

Lys Leu Tyr Gly Val Ala Pro Glu Ala Glu Gly Leu Leu Arg Cys Lys
            180                 185                 190

Asp Leu Pro Gly His Trp Ala Phe Ala Asp Glu Leu Lys Asp Asp Gln
        195                 200                 205

Leu Asn Phe Val Asp Gln Thr Thr Ala Ser Ser Arg Ser Ser Gly Leu
    210                 215                 220

Ile Leu Asn Thr Phe Asp Asp Leu Glu Ala Pro Phe Leu Gly Arg Leu
225                 230                 235                 240

Ser Thr Ile Phe Lys Lys Ile Tyr Ala Val Gly Pro Ile His Ser Leu
                245                 250                 255

Leu Asn Ser His His Cys Gly Leu Trp Lys Glu Asp His Ser Cys Leu
            260                 265                 270

Ala Trp Leu Asp Ser Arg Ala Ala Lys Ser Val Val Phe Val Ser Phe
        275                 280                 285

Gly Ser Leu Val Lys Ile Thr Ser Arg Gln Leu Met Glu Phe Trp His
    290                 295                 300

Gly Leu Leu Asn Ser Gly Lys Ser Phe Leu Phe Val Leu Arg Ser Asp
305                 310                 315                 320

Val Val Glu Gly Asp Asp Glu Lys Gln Val Lys Glu Ile Tyr Glu
                325                 330                 335

Thr Lys Ala Glu Gly Lys Trp Leu Val Val Gly Trp Ala Pro Gln Glu
            340                 345                 350

Lys Val Leu Ala His Glu Ala Val Gly Gly Phe Leu Thr His Ser Gly
        355                 360                 365
```

```
Trp Asn Ser Ile Leu Glu Ser Ile Ala Ala Gly Val Pro Met Ile Ser
    370                 375                 380

Cys Pro Lys Ile Gly Asp Gln Ser Ser Asn Cys Thr Trp Ile Ser Lys
385                 390                 395                 400

Val Trp Lys Ile Gly Leu Glu Met Glu Asp Arg Tyr Asp Arg Val Ser
                405                 410                 415

Val Glu Thr Met Val Arg Ser Ile Met Glu Gln Glu Gly Glu Lys Met
            420                 425                 430

Gln Lys Thr Ile Ala Glu Leu Ala Lys Gln Ala Lys Tyr Lys Val Ser
        435                 440                 445

Lys Asp Gly Thr Ser Tyr Gln Asn Leu Glu Cys Leu Ile Gln Asp Ile
450                 455                 460

Lys Lys Leu Asn Gln Ile Glu Gly Phe Ile Asn Asn Pro Asn Phe Ser
465                 470                 475                 480

Asp Leu Leu Arg Val
                485

<210> SEQ ID NO 23
<211> LENGTH: 473
<212> TYPE: PRT
<213> ORGANISM: Siraitia grosvenorii

<400> SEQUENCE: 23

Met Asp Ala Gln Gln Gly His Thr Thr Thr Ile Leu Met Leu Pro Trp
1               5                   10                  15

Val Gly Tyr Gly His Leu Leu Pro Phe Leu Glu Leu Ala Lys Ser Leu
            20                  25                  30

Ser Arg Arg Lys Leu Phe His Ile Tyr Phe Cys Ser Thr Ser Val Ser
        35                  40                  45

Leu Asp Ala Ile Lys Pro Lys Leu Pro Ser Ile Ser Ser Asp Asp
    50                  55                  60

Ser Ile Gln Leu Val Glu Leu Arg Leu Pro Ser Ser Pro Glu Leu Pro
65                  70                  75                  80

Pro His Leu His Thr Thr Asn Gly Leu Pro Ser His Leu Met Pro Ala
                85                  90                  95

Leu His Gln Ala Phe Val Met Ala Ala Gln His Phe Gln Val Ile Leu
            100                 105                 110

Gln Thr Leu Ala Pro His Leu Leu Ile Tyr Asp Ile Leu Gln Pro Trp
        115                 120                 125

Ala Pro Gln Val Ala Ser Ser Leu Asn Ile Pro Ala Ile Asn Phe Ser
    130                 135                 140

Thr Thr Gly Ala Ser Met Leu Ser Arg Thr Leu His Pro Thr His Tyr
145                 150                 155                 160

Pro Ser Ser Lys Phe Pro Ile Ser Glu Phe Val Leu His Asn His Trp
                165                 170                 175

Arg Ala Met Tyr Thr Thr Ala Asp Gly Ala Leu Thr Glu Glu Gly His
            180                 185                 190

Lys Ile Glu Glu Thr Leu Ala Asn Cys Leu His Thr Ser Cys Gly Val
        195                 200                 205

Val Leu Val Asn Ser Phe Arg Glu Leu Glu Thr Lys Tyr Ile Asp Tyr
    210                 215                 220

Leu Ser Val Leu Leu Asn Lys Lys Val Val Pro Val Gly Pro Leu Val
225                 230                 235                 240

Tyr Glu Pro Asn Gln Glu Gly Glu Asp Glu Gly Tyr Ser Ser Ile Lys
                245                 250                 255
```

Asn Trp Leu Asp Lys Lys Glu Pro Ser Ser Thr Val Phe Val Ser Phe
            260                 265                 270

Gly Thr Glu Tyr Phe Pro Ser Lys Glu Glu Met Glu Ile Ala Tyr
        275                 280                 285

Gly Leu Glu Leu Ser Glu Val Asn Phe Ile Trp Val Leu Arg Phe Pro
    290                 295                 300

Gln Gly Asp Ser Thr Ser Thr Ile Glu Asp Ala Leu Pro Lys Gly Phe
305                 310                 315                 320

Leu Glu Arg Ala Gly Glu Arg Ala Met Val Val Lys Gly Trp Ala Pro
            325                 330                 335

Gln Ala Lys Ile Leu Lys His Trp Ser Thr Gly Gly Leu Val Ser His
            340                 345                 350

Cys Gly Trp Asn Ser Met Met Glu Gly Met Met Phe Gly Val Pro Ile
        355                 360                 365

Ile Ala Val Pro Met His Leu Asp Gln Pro Phe Asn Ala Gly Leu Val
    370                 375                 380

Glu Glu Ala Gly Val Gly Val Glu Ala Lys Arg Asp Ser Asp Gly Lys
385                 390                 395                 400

Ile Gln Arg Glu Glu Val Ala Lys Ser Ile Lys Glu Val Val Ile Glu
            405                 410                 415

Lys Thr Arg Glu Asp Val Arg Lys Lys Ala Arg Glu Met Asp Thr Lys
        420                 425                 430

His Gly Pro Thr Tyr Phe Ser Arg Ser Lys Val Ser Ser Phe Gly Arg
    435                 440                 445

Leu Tyr Lys Ile Asn Arg Pro Thr Thr Leu Thr Val Gly Arg Phe Trp
    450                 455                 460

Ser Lys Gln Ile Lys Met Lys Arg Glu
465                 470

<210> SEQ ID NO 24
<211> LENGTH: 453
<212> TYPE: PRT
<213> ORGANISM: Siraitia grosvenorii

<400> SEQUENCE: 24

Met Asp Ala Gln Arg Gly His Thr Thr Thr Ile Leu Met Phe Pro Trp
1               5                   10                  15

Leu Gly Tyr Gly His Leu Ser Ala Phe Leu Glu Leu Ala Lys Ser Leu
            20                  25                  30

Ser Arg Arg Asn Phe His Ile Tyr Phe Cys Ser Thr Ser Val Asn Leu
        35                  40                  45

Asp Ala Ile Lys Pro Lys Leu Pro Ser Ser Ser Ser Asp Ser Ile
    50                  55                  60

Gln Leu Val Glu Leu Cys Leu Pro Ser Pro Asp Gln Leu Pro Pro
65              70                  75                  80

His Leu His Thr Thr Asn Ala Leu Pro Pro His Leu Met Pro Thr Leu
            85                  90                  95

His Gln Ala Phe Ser Met Ala Ala Gln His Phe Ala Ala Ile Leu His
            100                 105                 110

Thr Leu Ala Pro His Leu Leu Ile Tyr Asp Ser Phe Gln Pro Trp Ala
        115                 120                 125

Pro Gln Leu Ala Ser Ser Leu Asn Ile Pro Ala Ile Asn Phe Asn Thr
    130                 135                 140

Thr Gly Ala Ser Val Leu Thr Arg Met Leu His Ala Thr His Tyr Pro

```
                145                 150                 155                 160
        Ser Ser Lys Phe Pro Ile Ser Glu Phe Val Leu His Asp Tyr Trp Lys
                            165                 170                 175

Ala Met Tyr Ser Ala Ala Gly Gly Ala Val Thr Lys Lys Asp His Lys
                            180                 185                 190

Ile Gly Glu Thr Leu Ala Asn Cys Leu His Ala Ser Cys Ser Val Ile
                            195                 200                 205

Leu Ile Asn Ser Phe Arg Glu Leu Glu Lys Tyr Met Asp Tyr Leu
            210                 215                 220

Ser Val Leu Leu Asn Lys Lys Val Pro Val Gly Pro Leu Val Tyr
        225                 230                 235                 240

Glu Pro Asn Gln Asp Gly Glu Asp Gly Tyr Ser Ser Ile Lys Asn
                            245                 250                 255

Trp Leu Asp Lys Lys Glu Pro Ser Ser Thr Val Phe Val Ser Phe Gly
                            260                 265                 270

Ser Glu Tyr Phe Pro Ser Lys Glu Glu Met Glu Glu Ile Ala His Gly
                            275                 280                 285

Leu Glu Ala Ser Glu Val His Phe Ile Trp Val Val Arg Phe Pro Gln
            290                 295                 300

Gly Asp Asn Thr Ser Ala Ile Glu Asp Ala Leu Pro Lys Gly Phe Leu
        305                 310                 315                 320

Glu Arg Val Gly Glu Arg Gly Met Val Val Lys Gly Trp Ala Pro Gln
                            325                 330                 335

Ala Lys Ile Leu Lys His Trp Ser Thr Gly Gly Phe Val Ser His Cys
                            340                 345                 350

Gly Trp Asn Ser Val Met Glu Ser Met Met Phe Gly Val Pro Ile Ile
                            355                 360                 365

Gly Val Pro Met His Leu Asp Gln Pro Phe Asn Ala Gly Leu Ala Glu
                            370                 375                 380

Glu Ala Gly Val Gly Val Glu Ala Lys Arg Asp Pro Asp Gly Lys Ile
        385                 390                 395                 400

Gln Arg Asp Glu Val Ala Lys Leu Ile Lys Glu Val Val Glu Lys
                            405                 410                 415

Thr Arg Glu Asp Val Arg Lys Lys Ala Arg Glu Met Ser Glu Ile Leu
                            420                 425                 430

Arg Ser Lys Gly Glu Lys Met Asp Glu Met Val Ala Ala Ile Ser
            435                 440                 445

Leu Phe Leu Lys Ile
            450

<210> SEQ ID NO 25
<211> LENGTH: 472
<212> TYPE: PRT
<213> ORGANISM: Momordica charantia

<400> SEQUENCE: 25

Met Ala Gln Pro Gln Thr Gln Ala Arg Val Leu Val Phe Pro Tyr Pro
1               5                   10                  15

Thr Val Gly His Ile Lys Pro Phe Leu Ser Leu Ala Glu Leu Leu Ala
                20                  25                  30

Asp Gly Gly Leu Asp Val Val Phe Leu Ser Thr Glu Tyr Asn His Arg
            35                  40                  45

Arg Ile Pro Asn Leu Glu Ala Leu Ala Ser Arg Phe Pro Thr Leu His
        50                  55                  60
```

```
Phe Asp Thr Ile Pro Asp Gly Leu Pro Ile Asp Lys Pro Arg Val Ile
 65                  70                  75                  80

Ile Gly Gly Glu Leu Tyr Thr Ser Met Arg Asp Gly Val Lys Gln Arg
                 85                  90                  95

Leu Arg Gln Val Leu Gln Ser Tyr Asn Asp Gly Ser Ser Pro Ile Thr
                100                 105                 110

Cys Val Ile Cys Asp Val Met Leu Ser Gly Pro Ile Glu Ala Ala Glu
                115                 120                 125

Glu Leu Gly Ile Pro Val Val Thr Phe Cys Pro Tyr Ser Ala Arg Tyr
                130                 135                 140

Leu Cys Ala His Phe Val Met Pro Lys Leu Ile Glu Glu Gly Gln Ile
145                 150                 155                 160

Pro Phe Thr Asp Gly Asn Leu Ala Gly Glu Ile Gln Gly Val Pro Leu
                165                 170                 175

Phe Gly Gly Leu Leu Arg Arg Asp His Leu Pro Gly Phe Trp Phe Val
                180                 185                 190

Lys Ser Leu Ser Asp Glu Val Trp Ser His Ala Phe Leu Asn Gln Thr
                195                 200                 205

Leu Ala Val Gly Arg Thr Ser Ala Leu Ile Ile Asn Thr Leu Asp Glu
210                 215                 220

Leu Glu Ala Pro Phe Leu Ala His Leu Ser Ser Thr Phe Asp Lys Ile
225                 230                 235                 240

Tyr Pro Ile Gly Pro Leu Asp Ala Leu Ser Lys Ser Arg Leu Gly Asp
                245                 250                 255

Ser Ser Ser Ser Ser Thr Val Leu Thr Ala Phe Trp Lys Glu Asp Gln
                260                 265                 270

Ala Cys Met Ser Trp Leu Asp Ser Gln Pro Pro Lys Ser Val Ile Phe
                275                 280                 285

Val Ser Phe Gly Ser Thr Met Arg Met Thr Ala Asp Lys Leu Val Glu
                290                 295                 300

Phe Trp His Gly Leu Val Asn Ser Gly Thr Arg Phe Leu Cys Val Leu
305                 310                 315                 320

Arg Ser Asp Ile Val Glu Gly Gly Ala Ala Asp Leu Ile Lys Gln
                325                 330                 335

Val Gly Glu Thr Gly Asn Gly Ile Val Val Glu Trp Ala Ala Gln Glu
                340                 345                 350

Lys Val Leu Ala His Arg Ala Val Gly Gly Phe Leu Thr His Cys Gly
                355                 360                 365

Trp Asn Ser Thr Met Glu Ser Ile Ala Ala Gly Val Pro Met Met Cys
370                 375                 380

Trp Gln Ile Tyr Gly Asp Gln Met Ile Asn Ala Thr Trp Ile Gly Lys
385                 390                 395                 400

Val Trp Lys Ile Gly Ile Glu Arg Asp Asp Lys Trp Asp Arg Ser Thr
                405                 410                 415

Val Glu Lys Met Ile Lys Glu Leu Met Glu Gly Glu Lys Gly Ala Glu
                420                 425                 430

Ile Gln Arg Ser Met Glu Lys Phe Ser Lys Leu Ala Asn Asp Lys Val
                435                 440                 445

Val Lys Gly Gly Thr Ser Phe Glu Asn Leu Glu Leu Ile Val Glu Tyr
                450                 455                 460

Leu Lys Lys Leu Lys Pro Ser Asn
465                 470
```

<210> SEQ ID NO 26
<211> LENGTH: 466
<212> TYPE: PRT
<213> ORGANISM: Momordica charantia

<400> SEQUENCE: 26

```
Met Ala Gln Pro Arg Val Leu Leu Phe Pro Phe Pro Ala Met Gly His
1               5                   10                  15

Val Lys Pro Phe Leu Ser Leu Ala Glu Leu Leu Ser Asp Ala Gly Val
            20                  25                  30

Glu Val Val Phe Leu Ser Thr Glu Tyr Asn His Arg Arg Ile Pro Asp
        35                  40                  45

Ile Gly Ala Leu Ala Ala Arg Phe Pro Thr Leu His Phe Glu Thr Ile
    50                  55                  60

Pro Asp Gly Leu Pro Pro Asp Gln Pro Arg Val Leu Ala Asp Gly His
65                  70                  75                  80

Leu Tyr Phe Ser Met Leu Asp Gly Thr Lys Pro Arg Phe Arg Gln Leu
                85                  90                  95

Ile Gln Ser Leu Asn Gly Asn Pro Arg Pro Ile Thr Cys Ile Ile Asn
            100                 105                 110

Asp Val Met Leu Ser Ser Pro Ile Glu Val Ala Glu Glu Phe Gly Ile
        115                 120                 125

Pro Val Ile Ala Phe Cys Pro Cys Ser Ala Arg Phe Leu Ser Val His
    130                 135                 140

Phe Phe Met Pro Asn Phe Ile Glu Glu Ala Gln Ile Pro Tyr Thr Asp
145                 150                 155                 160

Glu Asn Pro Met Gly Lys Ile Glu Glu Ala Thr Val Phe Glu Gly Leu
                165                 170                 175

Leu Arg Arg Lys Asp Leu Pro Gly Leu Trp Cys Ala Lys Ser Ser Asn
            180                 185                 190

Ile Ser Phe Ser His Arg Phe Ile Asn Gln Thr Ile Ala Ala Gly Arg
        195                 200                 205

Ala Ser Ala Leu Ile Leu Asn Thr Phe Asp Glu Leu Glu Ser Pro Phe
    210                 215                 220

Leu Asn His Leu Ser Ser Ile Phe Pro Lys Ile Tyr Cys Ile Gly Pro
225                 230                 235                 240

Leu Asn Ala Leu Ser Arg Ser Arg Leu Gly Lys Ser Ser Ser Ser Ser
                245                 250                 255

Ser Ala Leu Ala Gly Phe Trp Lys Glu Asp Gln Ala Tyr Met Ser Trp
            260                 265                 270

Leu Glu Ser Gln Pro Pro Arg Ser Val Ile Phe Val Ser Phe Gly Ser
        275                 280                 285

Thr Met Lys Met Glu Ala Trp Lys Leu Ala Glu Phe Trp Tyr Gly Leu
    290                 295                 300

Val Asn Ser Gly Ser Pro Phe Leu Phe Val Phe Arg Pro Asp Cys Val
305                 310                 315                 320

Ile Asn Ser Gly Asp Ala Ala Glu Val Met Glu Gly Arg Gly Arg Gly
                325                 330                 335

Met Val Val Glu Trp Ala Ser Gln Glu Lys Val Leu Ala His Pro Ala
            340                 345                 350

Val Gly Gly Phe Leu Thr His Cys Gly Trp Asn Ser Thr Val Glu Ser
        355                 360                 365

Ile Val Ala Gly Val Pro Met Met Cys Cys Pro Ile Val Ala Asp Gln
    370                 375                 380
```

```
Leu Ser Asn Ala Thr Trp Ile His Lys Val Trp Lys Ile Gly Ile Glu
385                 390                 395                 400

Gly Asp Glu Lys Trp Asp Arg Ser Thr Val Glu Met Met Ile Lys Glu
            405                 410                 415

Leu Met Glu Ser Gln Lys Gly Thr Glu Ile Arg Thr Ser Ile Glu Met
            420                 425                 430

Leu Ser Lys Leu Ala Asn Glu Lys Val Val Lys Gly Thr Ser Leu
        435                 440                 445

Asn Asn Phe Glu Leu Leu Val Glu Asp Ile Lys Thr Leu Arg Arg Pro
450                 455                 460

Tyr Thr
465

<210> SEQ ID NO 27
<211> LENGTH: 482
<212> TYPE: PRT
<213> ORGANISM: Momordica charantia

<400> SEQUENCE: 27

Met Glu Gln Ser Asp Ser Asn Ser Asp Asp His Gln His His Val Leu
1               5                   10                  15

Leu Phe Pro Phe Pro Ala Lys Gly His Ile Lys Pro Phe Leu Cys Leu
                20                  25                  30

Ala Gln Leu Leu Cys Gly Ala Gly Leu Gln Val Thr Phe Leu Asn Thr
            35                  40                  45

Asp His Asn His Arg Arg Ile Asp Asp Arg His Arg Arg Leu Leu Ala
        50                  55                  60

Thr Gln Phe Pro Met Leu His Phe Lys Ser Ile Ser Asp Gly Leu Pro
65                  70                  75                  80

Pro Asp His Pro Arg Asp Leu Leu Asp Gly Lys Leu Ile Ala Ser Met
                85                  90                  95

Arg Arg Val Thr Glu Ser Leu Phe Arg Gln Leu Leu Leu Ser Tyr Asn
            100                 105                 110

Gly Tyr Gly Asn Gly Thr Asn Asn Val Ser Asn Ser Gly Arg Arg Pro
        115                 120                 125

Pro Ile Ser Cys Val Ile Thr Asp Val Ile Phe Ser Phe Pro Val Glu
130                 135                 140

Val Ala Glu Glu Leu Gly Ile Pro Val Phe Ser Phe Ala Thr Phe Ser
145                 150                 155                 160

Ala Arg Phe Leu Phe Leu Tyr Phe Trp Ile Pro Lys Leu Ile Gln Glu
                165                 170                 175

Gly Gln Leu Pro Phe Pro Asp Gly Lys Thr Asn Gln Glu Leu Tyr Gly
            180                 185                 190

Val Pro Gly Ala Glu Gly Ile Ile Arg Cys Lys Asp Leu Pro Gly Ser
        195                 200                 205

Trp Ser Val Glu Ala Val Ala Lys Asn Asp Pro Met Asn Phe Val Lys
210                 215                 220

Gln Thr Leu Ala Ser Ser Arg Ser Ser Gly Leu Ile Leu Asn Thr Phe
225                 230                 235                 240

Glu Asp Leu Glu Ala Pro Phe Val Thr His Leu Ser Asn Thr Phe Asp
                245                 250                 255

Lys Ile Tyr Thr Ile Gly Pro Ile His Ser Leu Leu Gly Thr Ser His
            260                 265                 270

Cys Gly Leu Trp Lys Glu Asp Tyr Ala Cys Leu Ala Trp Leu Asp Ala
        275                 280                 285
```

```
Arg Pro Arg Lys Ser Val Val Phe Val Ser Phe Gly Ser Leu Val Lys
        290                 295                 300

Thr Thr Ser Arg Glu Leu Met Glu Leu Trp His Gly Leu Val Ser Ser
305                 310                 315                 320

Gly Lys Ser Phe Leu Leu Val Leu Arg Ser Asp Val Val Glu Gly Glu
                325                 330                 335

Asp Glu Glu Gln Val Val Lys Glu Ile Leu Glu Ser Asn Gly Glu Gly
                340                 345                 350

Lys Trp Leu Val Val Gly Trp Ala Pro Gln Glu Val Leu Ala His
                355                 360                 365

Glu Ala Ile Gly Gly Phe Leu Thr His Ser Gly Trp Asn Ser Thr Met
370                 375                 380

Glu Ser Ile Ala Ala Gly Val Pro Met Val Cys Trp Pro Lys Ile Gly
385                 390                 395                 400

Asp Gln Pro Ser Asn Cys Thr Trp Val Ser Arg Val Trp Lys Val Gly
                405                 410                 415

Leu Glu Met Glu Glu Arg Tyr Asp Arg Ser Thr Val Ala Arg Met Ala
                420                 425                 430

Arg Ser Met Met Glu Gln Glu Gly Lys Glu Met Glu Arg Ile Ala
                435                 440                 445

Glu Leu Ala Lys Arg Val Lys Tyr Arg Val Gly Lys Asp Gly Glu Ser
450                 455                 460

Tyr Arg Asn Leu Glu Ser Leu Ile Arg Asp Ile Lys Ile Thr Lys Ser
465                 470                 475                 480

Ser Asn

<210> SEQ ID NO 28
<211> LENGTH: 471
<212> TYPE: PRT
<213> ORGANISM: Cucumis sativus

<400> SEQUENCE: 28

Met Gly Leu Ser Pro Thr Asp His Val Leu Leu Phe Pro Phe Pro Ala
1               5                   10                  15

Lys Gly His Ile Lys Pro Phe Phe Cys Leu Ala His Leu Leu Cys Asn
                20                  25                  30

Ala Gly Leu Arg Val Thr Phe Leu Ser Thr Glu His His His Gln Lys
            35                  40                  45

Leu His Asn Leu Thr His Leu Ala Ala Gln Ile Pro Ser Leu His Phe
    50                  55                  60

Gln Ser Ile Ser Asp Gly Leu Ser Leu Asp His Pro Arg Asn Leu Leu
65                  70                  75                  80

Asp Gly Gln Leu Phe Lys Ser Met Pro Gln Val Thr Lys Pro Leu Phe
                85                  90                  95

Arg Gln Leu Leu Leu Ser Tyr Lys Asp Gly Thr Ser Pro Ile Thr Cys
            100                 105                 110

Val Ile Thr Asp Leu Ile Leu Arg Phe Pro Met Asp Val Ala Gln Glu
        115                 120                 125

Leu Asp Ile Pro Val Phe Cys Phe Ser Thr Phe Ser Ala Arg Phe Leu
    130                 135                 140

Phe Leu Tyr Phe Ser Ile Pro Lys Leu Leu Glu Asp Gly Gln Ile Pro
145                 150                 155                 160

Tyr Pro Glu Gly Asn Ser Asn Gln Val Leu His Gly Ile Pro Gly Ala
                165                 170                 175
```

```
Glu Gly Leu Leu Arg Cys Lys Asp Leu Pro Gly Tyr Trp Ser Val Glu
            180                 185                 190

Ala Val Ala Asn Tyr Asn Pro Met Asn Phe Val Asn Gln Thr Ile Ala
        195                 200                 205

Thr Ser Lys Ser His Gly Leu Ile Leu Asn Thr Phe Asp Glu Leu Glu
    210                 215                 220

Val Pro Phe Ile Thr Asn Leu Ser Lys Ile Tyr Lys Val Tyr Thr
225                 230                 235                 240

Ile Gly Pro Ile His Ser Leu Leu Lys Lys Ser Val Gln Thr Gln Tyr
                245                 250                 255

Glu Phe Trp Lys Glu Asp His Ser Cys Leu Ala Trp Leu Asp Ser Gln
            260                 265                 270

Pro Pro Arg Ser Val Met Phe Val Ser Phe Gly Ser Ile Val Lys Leu
        275                 280                 285

Lys Ser Ser Gln Leu Lys Glu Phe Trp Asn Gly Leu Val Asp Ser Gly
    290                 295                 300

Lys Ala Phe Leu Leu Val Leu Arg Ser Asp Ala Leu Val Glu Glu Thr
305                 310                 315                 320

Gly Glu Glu Asp Glu Lys Gln Lys Glu Leu Val Ile Lys Glu Ile Met
                325                 330                 335

Glu Thr Lys Glu Glu Gly Arg Trp Val Ile Val Asn Trp Ala Pro Gln
            340                 345                 350

Glu Lys Val Leu Glu His Lys Ala Ile Gly Gly Phe Leu Thr His Ser
        355                 360                 365

Gly Trp Asn Ser Thr Leu Glu Ser Val Ala Val Gly Val Pro Met Val
    370                 375                 380

Ser Trp Pro Gln Ile Gly Asp Gln Pro Ser Asn Ala Thr Trp Leu Ser
385                 390                 395                 400

Lys Val Trp Lys Ile Gly Val Glu Met Glu Asp Ser Tyr Asp Arg Ser
                405                 410                 415

Thr Val Glu Ser Lys Val Arg Ser Ile Met Glu His Glu Asp Lys Lys
            420                 425                 430

Met Glu Asn Ala Ile Val Glu Leu Ala Lys Arg Val Asp Asp Arg Val
        435                 440                 445

Ser Lys Glu Gly Thr Ser Tyr Gln Asn Leu Gln Arg Leu Ile Glu Asp
    450                 455                 460

Ile Glu Gly Phe Lys Leu Asn
465                 470

<210> SEQ ID NO 29
<211> LENGTH: 462
<212> TYPE: PRT
<213> ORGANISM: Cucurbita maxima

<400> SEQUENCE: 29

Met Glu Leu Ser His Thr His His Val Leu Leu Phe Pro Phe Pro Ala
1               5                   10                  15

Lys Gly His Ile Lys Pro Phe Phe Ser Leu Ala Gln Leu Leu Cys Asn
            20                  25                  30

Ala Gly Leu Arg Val Thr Phe Leu Asn Thr Asp His His Arg Arg
        35                  40                  45

Ile His Asp Leu Asn Arg Leu Ala Ala Gln Leu Pro Thr Leu His Phe
    50                  55                  60

Asp Ser Val Ser Asp Gly Leu Pro Pro Asp Glu Pro Arg Asn Val Phe
```

```
                65                  70                  75                  80
Asp Gly Lys Leu Tyr Glu Ser Ile Arg Gln Val Thr Ser Ser Leu Phe
                    85                  90                  95
Arg Glu Leu Leu Val Ser Tyr Asn Asn Gly Thr Ser Ser Gly Arg Pro
                100                 105                 110
Pro Ile Thr Cys Val Ile Thr Asp Val Met Phe Arg Phe Pro Ile Asp
                115                 120                 125
Ile Ala Glu Glu Leu Gly Ile Pro Val Phe Thr Phe Ser Thr Phe Ser
130                 135                 140
Ala Arg Phe Leu Phe Leu Ile Phe Trp Ile Pro Lys Leu Leu Glu Asp
145                 150                 155                 160
Gly Gln Leu Arg Tyr Pro Glu Gln Glu Leu His Gly Val Pro Gly Ala
                165                 170                 175
Glu Gly Leu Ile Arg Trp Lys Asp Leu Pro Gly Phe Trp Ser Val Glu
                180                 185                 190
Asp Val Ala Asp Trp Asp Pro Met Asn Phe Val Asn Gln Thr Leu Ala
                195                 200                 205
Thr Ser Arg Ser Ser Gly Leu Ile Leu Asn Thr Phe Asp Glu Leu Glu
    210                 215                 220
Ala Pro Phe Leu Thr Ser Leu Ser Lys Ile Tyr Lys Lys Ile Tyr Ser
225                 230                 235                 240
Leu Gly Pro Ile Asn Ser Leu Leu Lys Asn Phe Gln Ser Gln Pro Gln
                245                 250                 255
Tyr Asn Leu Trp Lys Glu Asp His Ser Cys Met Ala Trp Leu Asp Ser
                260                 265                 270
Gln Pro Arg Lys Ser Val Val Phe Val Ser Phe Gly Ser Val Val Lys
                275                 280                 285
Leu Thr Ser Arg Gln Leu Met Glu Phe Trp Asn Gly Leu Val Asn Ser
                290                 295                 300
Gly Met Pro Phe Leu Leu Val Leu Arg Ser Asp Val Ile Glu Ala Gly
305                 310                 315                 320
Glu Glu Val Val Arg Glu Ile Met Glu Arg Lys Ala Glu Gly Arg Trp
                325                 330                 335
Val Ile Val Ser Trp Ala Pro Gln Glu Glu Val Leu Ala His Asp Ala
                340                 345                 350
Val Gly Gly Phe Leu Thr His Ser Gly Trp Asn Ser Thr Leu Glu Ser
                355                 360                 365
Leu Ala Ala Gly Val Pro Met Ile Ser Trp Pro Gln Ile Gly Asp Gln
370                 375                 380
Thr Ser Asn Ser Thr Trp Ile Ser Lys Val Trp Arg Ile Gly Leu Gln
385                 390                 395                 400
Leu Glu Asp Gly Phe Asp Ser Ser Thr Ile Glu Thr Met Val Arg Ser
                405                 410                 415
Ile Met Asp Gln Thr Met Glu Lys Thr Val Ala Glu Leu Ala Glu Arg
                420                 425                 430
Ala Lys Asn Arg Ala Ser Lys Asn Gly Thr Ser Tyr Arg Asn Phe Gln
                435                 440                 445
Thr Leu Ile Gln Asp Ile Thr Asn Ile Ile Glu Thr His Ile
    450                 455                 460

<210> SEQ ID NO 30
<211> LENGTH: 462
<212> TYPE: PRT
<213> ORGANISM: Cucurbita moschata
```

<400> SEQUENCE: 30

```
Met Glu Leu Ser Pro Thr His His Leu Leu Phe Pro Phe Pro Ala
1               5                   10                  15

Lys Gly His Ile Lys Pro Phe Phe Ser Leu Ala Gln Leu Leu Cys Asn
            20                  25                  30

Ala Gly Ala Arg Val Thr Phe Leu Asn Thr Asp His His Arg Arg
        35                  40                  45

Ile His Asp Leu Asp Arg Leu Ala Ala Gln Leu Pro Thr Leu His Phe
    50                  55                  60

Asp Ser Val Ser Asp Gly Leu Pro Pro Asp Glu Ser Arg Asn Val Phe
65                  70                  75                  80

Asp Gly Lys Leu Tyr Glu Ser Ile Arg Gln Val Thr Ser Ser Leu Phe
                85                  90                  95

Arg Glu Leu Leu Val Ser Tyr Asn Asn Gly Thr Ser Ser Gly Arg Pro
                100                 105                 110

Pro Ile Thr Cys Val Ile Thr Asp Cys Met Phe Arg Phe Pro Ile Asp
            115                 120                 125

Ile Ala Glu Glu Leu Gly Ile Pro Val Phe Thr Phe Ser Thr Phe Ser
130                 135                 140

Ala Arg Phe Leu Phe Leu Phe Phe Trp Ile Pro Lys Leu Leu Glu Asp
145                 150                 155                 160

Gly Gln Leu Arg Tyr Pro Glu Gln Glu Leu His Gly Val Pro Gly Ala
                165                 170                 175

Glu Gly Leu Ile Arg Cys Lys Asp Leu Pro Gly Phe Leu Ser Asp Glu
            180                 185                 190

Asp Val Ala His Trp Lys Pro Ile Asn Phe Val Asn Gln Ile Leu Ala
            195                 200                 205

Thr Ser Arg Ser Ser Gly Leu Ile Leu Asn Thr Phe Asp Glu Leu Glu
210                 215                 220

Ala Pro Phe Leu Thr Ser Leu Ser Lys Ile Tyr Lys Lys Ile Tyr Ser
225                 230                 235                 240

Leu Gly Pro Ile Asn Ser Leu Leu Lys Asn Phe Gln Ser Gln Pro Gln
                245                 250                 255

Tyr Asn Leu Trp Lys Glu Asp His Ser Cys Met Ala Trp Leu Asp Ser
            260                 265                 270

Gln Pro Pro Lys Ser Val Val Phe Val Ser Phe Gly Ser Val Val Lys
            275                 280                 285

Leu Thr Asn Arg Gln Leu Val Glu Phe Trp Asn Gly Leu Val Asn Ser
290                 295                 300

Gly Lys Pro Phe Leu Leu Val Leu Arg Ser Asp Val Ile Glu Ala Gly
305                 310                 315                 320

Glu Glu Val Val Arg Glu Asn Met Glu Arg Lys Ala Glu Gly Arg Trp
                325                 330                 335

Met Ile Val Ser Trp Ala Pro Gln Glu Val Leu Ala His Asp Ala
            340                 345                 350

Val Gly Gly Phe Leu Thr His Ser Gly Trp Asn Ser Thr Leu Glu Ser
            355                 360                 365

Leu Ala Ala Gly Val Pro Met Ile Ser Trp Thr Gln Ile Gly Asp Gln
370                 375                 380

Thr Ser Asn Ser Thr Trp Val Ser Lys Val Trp Arg Ile Gly Leu Gln
385                 390                 395                 400

Leu Glu Asp Gly Phe Asp Ser Phe Thr Ile Glu Thr Met Val Arg Ser
```

```
                405                 410                 415
Val Met Asp Gln Thr Met Glu Lys Thr Val Ala Glu Leu Ala Glu Arg
        420                 425                 430

Ala Lys Asn Arg Ala Ser Lys Asn Gly Thr Ser Tyr Arg Asn Phe Gln
        435                 440                 445

Thr Leu Ile Gln Asp Ile Thr Asn Ile Ile Glu Thr His Ile
        450                 455                 460

<210> SEQ ID NO 31
<211> LENGTH: 474
<212> TYPE: PRT
<213> ORGANISM: Prunus persica

<400> SEQUENCE: 31

Met Ala Met Lys Gln Pro His Val Ile Phe Pro Phe Pro Leu Gln
1               5                   10                  15

Gly His Met Lys Pro Leu Leu Cys Leu Ala Glu Leu Leu Cys His Ala
            20                  25                  30

Gly Leu His Val Thr Tyr Val Asn Thr His His Asn His Gln Arg Leu
        35                  40                  45

Ala Asn Arg Gln Ala Leu Ser Thr His Phe Pro Thr Leu His Phe Glu
    50                  55                  60

Ser Ile Ser Asp Gly Leu Pro Glu Asp Pro Arg Thr Leu Asn Ser
65                  70                  75                  80

Gln Leu Leu Ile Ala Leu Lys Thr Ser Ile Arg Pro His Phe Arg Glu
                85                  90                  95

Leu Leu Lys Thr Ile Ser Leu Lys Ala Glu Ser Asn Asp Thr Leu Val
            100                 105                 110

Pro Pro Pro Ser Cys Ile Met Thr Asp Gly Leu Val Thr Phe Ala Phe
        115                 120                 125

Asp Val Ala Glu Glu Leu Gly Leu Pro Ile Leu Ser Phe Asn Val Pro
    130                 135                 140

Cys Pro Arg Tyr Leu Trp Thr Cys Leu Cys Leu Pro Lys Leu Ile Glu
145                 150                 155                 160

Asn Gly Gln Leu Pro Phe Gln Asp Asp Met Asn Val Glu Ile Thr
                165                 170                 175

Gly Val Pro Gly Met Glu Gly Leu Leu His Arg Gln Asp Leu Pro Gly
            180                 185                 190

Phe Cys Arg Val Lys Gln Ala Asp His Pro Ser Leu Gln Phe Ala Ile
        195                 200                 205

Asn Glu Thr Gln Thr Leu Lys Arg Ala Ser Ala Leu Ile Leu Asp Thr
    210                 215                 220

Val Tyr Glu Leu Asp Ala Pro Cys Ile Ser His Met Ala Leu Met Phe
225                 230                 235                 240

Pro Lys Ile Tyr Thr Leu Gly Pro Leu His Ala Leu Leu Asn Ser Gln
                245                 250                 255

Ile Gly Asp Met Ser Arg Gly Leu Ala Ser His Gly Ser Leu Trp Lys
            260                 265                 270

Ser Asp Leu Asn Cys Met Thr Trp Leu Asp Ser Gln Pro Ser Lys Ser
        275                 280                 285

Ile Ile Tyr Val Ser Phe Gly Thr Leu Val His Leu Thr Arg Ala Gln
    290                 295                 300

Val Ile Glu Phe Trp Tyr Gly Leu Val Asn Ser Gly His Pro Phe Leu
305                 310                 315                 320
```

```
Trp Val Met Arg Ser Asp Ile Thr Ser Gly Asp His Gln Ile Pro Ala
            325                 330                 335

Glu Leu Glu Asn Gly Thr Lys Glu Arg Gly Cys Ile Val Asp Trp Val
            340                 345                 350

Ser Gln Glu Glu Val Leu Ala His Lys Ser Val Gly Gly Phe Leu Thr
            355                 360                 365

His Ser Gly Trp Asn Ser Thr Leu Glu Ser Ile Val Ala Gly Leu Pro
            370                 375                 380

Met Ile Cys Trp Pro Lys Leu Gly Asp His Tyr Ile Ile Ser Ser Thr
385                 390                 395                 400

Val Cys Arg Gln Trp Lys Ile Gly Leu Gln Leu Asn Glu Asn Cys Asp
            405                 410                 415

Arg Ser Asn Ile Glu Ser Met Val Gln Thr Leu Met Gly Ser Lys Arg
            420                 425                 430

Glu Glu Ile Gln Ser Ser Met Asp Ala Ile Ser Lys Leu Ser Arg Asp
            435                 440                 445

Ser Val Ala Glu Gly Gly Ser Ser His Asn Asn Leu Gly Gln Leu Ile
            450                 455                 460

Glu Tyr Ile Arg Asn Leu Gln His Gln Asn
465                 470

<210> SEQ ID NO 32
<211> LENGTH: 468
<212> TYPE: PRT
<213> ORGANISM: Theobroma cacao

<400> SEQUENCE: 32

Met Arg Gln Pro His Val Leu Val Leu Pro Phe Pro Ala Gln Gly His
1               5                   10                  15

Ile Lys Pro Met Leu Cys Leu Ala Glu Leu Leu Cys Gln Ala Gly Leu
            20                  25                  30

Arg Val Thr Phe Leu Asn Thr His His Ser His Arg Arg Leu Asn Asn
            35                  40                  45

Leu Gln Asp Leu Ser Thr Arg Phe Pro Thr Leu His Phe Glu Ser Val
    50                  55                  60

Ser Asp Gly Leu Pro Glu Asp His Pro Arg Asn Leu Val His Phe Met
65                  70                  75                  80

His Leu Val His Ser Ile Lys Asn Val Thr Lys Pro Leu Leu Arg Asp
                85                  90                  95

Leu Leu Thr Ser Leu Ser Leu Lys Thr Asp Ile Pro Pro Val Ser Cys
            100                 105                 110

Ile Ile Ala Asp Gly Ile Leu Ser Phe Ala Ile Asp Val Ala Glu Glu
            115                 120                 125

Leu Gln Ile Lys Val Ile Ile Phe Arg Thr Ile Ser Ser Cys Cys Leu
    130                 135                 140

Trp Ser Tyr Leu Cys Val Pro Lys Leu Ile Gln Gln Gly Glu Leu Gln
145                 150                 155                 160

Phe Ser Asp Ser Asp Met Gly Gln Lys Val Ser Ser Val Pro Glu Met
                165                 170                 175

Lys Gly Ser Leu Arg Leu His Asp Arg Pro Tyr Ser Phe Gly Leu Lys
            180                 185                 190

Gln Leu Glu Asp Pro Asn Phe Gln Phe Phe Val Ser Glu Thr Gln Ala
            195                 200                 205

Met Thr Arg Ala Ser Ala Val Ile Phe Asn Thr Phe Asp Ser Leu Glu
    210                 215                 220
```

```
Ala Pro Val Leu Ser Gln Met Ile Pro Leu Leu Pro Lys Val Tyr Thr
225                 230                 235                 240

Ile Gly Pro Leu His Ala Leu Arg Lys Ala Arg Leu Gly Asp Leu Ser
            245                 250                 255

Gln His Ser Ser Phe Asn Gly Asn Leu Arg Glu Ala Asp His Asn Cys
        260                 265                 270

Ile Thr Trp Leu Asp Ser Gln Pro Leu Arg Ser Val Val Tyr Val Ser
    275                 280                 285

Phe Gly Ser His Val Val Leu Thr Ser Glu Glu Leu Glu Phe Trp
290                 295                 300

His Gly Leu Val Asn Ser Gly Lys Arg Phe Leu Trp Val Leu Arg Pro
305                 310                 315                 320

Asp Ile Ile Ala Gly Glu Lys Asp His Asn Gln Ile Ile Ala Arg Glu
                325                 330                 335

Pro Asp Leu Gly Thr Lys Glu Lys Gly Leu Leu Val Asp Trp Ala Pro
            340                 345                 350

Gln Glu Glu Val Leu Ala His Pro Ser Val Gly Gly Phe Leu Thr His
        355                 360                 365

Cys Gly Trp Asn Ser Thr Leu Glu Ser Met Val Ala Gly Val Pro Met
370                 375                 380

Leu Cys Trp Pro Lys Leu Pro Asp Gln Leu Val Asn Ser Ser Cys Val
385                 390                 395                 400

Ser Glu Val Trp Lys Ile Gly Leu Asp Leu Lys Asp Met Cys Asp Arg
                405                 410                 415

Ser Thr Val Glu Lys Met Val Arg Ala Leu Met Glu Asp Arg Arg Glu
            420                 425                 430

Glu Val Met Arg Ser Val Asp Gly Ile Ser Lys Leu Ala Arg Glu Ser
        435                 440                 445

Val Ser His Gly Gly Ser Ser Ser Asn Leu Glu Met Leu Ile Gln
    450                 455                 460

Glu Leu Glu Thr
465

<210> SEQ ID NO 33
<211> LENGTH: 450
<212> TYPE: PRT
<213> ORGANISM: Momordica charantia

<400> SEQUENCE: 33

Met Asp Ala His Gln Gln Ala Glu His Thr Thr Thr Ile Leu Met Leu
1               5                   10                  15

Pro Trp Val Gly Tyr Gly His Leu Thr Ala Tyr Leu Glu Leu Ala Lys
            20                  25                  30

Ala Leu Ser Arg Arg Asn Phe His Ile Tyr Tyr Cys Ser Thr Pro Val
        35                  40                  45

Asn Ile Glu Ser Ile Lys Pro Lys Leu Thr Ile Pro Cys Ser Ser Ile
    50                  55                  60

Gln Phe Val Glu Leu His Leu Pro Ser Ser Asp Asp Leu Pro Pro Asn
65                  70                  75                  80

Leu His Thr Thr Asn Gly Leu Pro Ser His Leu Met Pro Thr Leu His
                85                  90                  95

Gln Ala Phe Ser Ala Ala Ala Pro Leu Phe Glu Glu Ile Leu Gln Thr
            100                 105                 110

Leu Cys Pro His Leu Leu Ile Tyr Asp Ser Leu Gln Pro Trp Ala Pro
```

```
            115                 120                 125
Lys Ile Ala Ser Ser Leu Lys Ile Pro Ala Leu Asn Phe Asn Thr Ser
    130                 135                 140

Gly Val Ser Val Ile Ala Gln Ala Leu His Ala Ile His His Pro Asp
145                 150                 155                 160

Ser Lys Phe Pro Leu Ser Asp Phe Ile Leu His Asn Tyr Trp Lys Ser
                165                 170                 175

Thr Tyr Thr Thr Ala Asp Gly Gly Ala Ser Glu Lys Thr Arg Arg Ala
            180                 185                 190

Arg Glu Ala Phe Leu Tyr Cys Leu Asn Ser Ser Gly Asn Ala Ile Leu
        195                 200                 205

Ile Asn Thr Phe Arg Glu Leu Glu Gly Glu Tyr Ile Asp Tyr Leu Ser
    210                 215                 220

Leu Leu Leu Asn Lys Lys Val Ile Pro Ile Gly Pro Leu Val Tyr Glu
225                 230                 235                 240

Pro Asn Gln Asp Glu Asp Gln Asp Glu Glu Tyr Arg Ser Ile Lys Asn
                245                 250                 255

Trp Leu Asp Lys Lys Glu Pro Cys Ser Thr Val Phe Val Ser Phe Gly
            260                 265                 270

Ser Glu Tyr Phe Pro Ser Asn Glu Glu Met Glu Glu Ile Ala Pro Gly
        275                 280                 285

Leu Glu Glu Ser Gly Ala Asn Phe Ile Trp Val Val Arg Phe Pro Lys
290                 295                 300

Leu Glu Asn Arg Asn Gly Ile Ile Glu Glu Gly Leu Leu Glu Arg Ala
305                 310                 315                 320

Gly Glu Arg Gly Met Val Ile Lys Glu Trp Ala Pro Gln Ala Arg Ile
                325                 330                 335

Leu Arg His Gly Ser Ile Gly Gly Phe Val Ser His Cys Gly Trp Asn
            340                 345                 350

Ser Val Met Glu Ser Ile Ile Cys Gly Val Pro Val Ile Gly Val Pro
        355                 360                 365

Met Arg Val Asp Gln Pro Tyr Asn Ala Gly Leu Val Glu Glu Ala Gly
    370                 375                 380

Val Gly Val Glu Ala Lys Arg Asp Pro Asp Gly Lys Ile Gln Arg His
385                 390                 395                 400

Glu Val Ser Lys Leu Ile Lys Gln Val Val Glu Lys Thr Arg Asp
                405                 410                 415

Asp Val Arg Lys Lys Val Ala Gln Met Ser Glu Ile Leu Arg Arg Lys
            420                 425                 430

Gly Asp Glu Lys Ile Asp Glu Met Val Ala Leu Ile Ser Leu Leu Pro
        435                 440                 445

Lys Gly
    450

<210> SEQ ID NO 34
<211> LENGTH: 454
<212> TYPE: PRT
<213> ORGANISM: Cucurbita maxima

<400> SEQUENCE: 34

Met Asp Ala Gln Lys Ala Val Asp Thr Pro Thr Thr Val Leu Met
1               5                   10                  15

Leu Pro Trp Ile Gly Tyr Gly His Leu Ser Ala Tyr Leu Glu Leu Ala
            20                  25                  30
```

```
Lys Ala Leu Ser Arg Arg Asn Phe His Val Tyr Phe Cys Ser Thr Pro
             35                  40                  45

Val Asn Leu Asp Ser Ile Lys Pro Asn Leu Ile Pro Pro Pro Ser Ser
 50                  55                  60

Ile Gln Phe Val Asp Leu His Leu Pro Ser Ser Pro Glu Leu Pro Pro
 65                  70                  75                  80

His Leu His Thr Thr Asn Gly Leu Pro Ser His Leu Lys Pro Thr Leu
                 85                  90                  95

His Gln Ala Phe Ser Ala Ala Gln His Phe Glu Ala Ile Leu Gln
                100                 105                 110

Thr Leu Ser Pro His Leu Leu Ile Tyr Asp Ser Leu Gln Pro Trp Ala
                115                 120                 125

Pro Arg Ile Ala Ser Ser Leu Asn Ile Pro Ala Ile Asn Phe Asn Thr
130                 135                 140

Thr Ala Val Ser Ile Ile Ala His Ala Leu His Ser Val His Tyr Pro
145                 150                 155                 160

Asp Ser Lys Phe Pro Phe Ser Asp Phe Val Leu His Asp Tyr Trp Lys
                165                 170                 175

Ala Lys Tyr Thr Thr Ala Asp Gly Ala Thr Ser Glu Lys Ile Arg Arg
                180                 185                 190

Gly Ala Glu Ala Phe Leu Tyr Cys Leu Asn Ala Ser Cys Asp Val Val
                195                 200                 205

Leu Val Asn Ser Phe Arg Glu Leu Glu Gly Glu Tyr Met Asp Tyr Leu
                210                 215                 220

Ser Val Leu Leu Lys Lys Lys Val Val Ser Val Gly Pro Leu Val Tyr
225                 230                 235                 240

Glu Pro Ser Glu Gly Glu Glu Asp Glu Glu Tyr Trp Arg Ile Lys Lys
                245                 250                 255

Trp Leu Asp Glu Lys Glu Ala Leu Ser Thr Val Leu Val Ser Phe Gly
                260                 265                 270

Ser Glu Tyr Phe Pro Ser Lys Glu Glu Met Glu Glu Ile Ala His Gly
                275                 280                 285

Leu Glu Glu Ser Glu Ala Asn Phe Ile Trp Val Val Arg Phe Pro Lys
290                 295                 300

Gly Glu Glu Ser Cys Arg Gly Ile Glu Glu Ala Leu Pro Lys Gly Phe
305                 310                 315                 320

Val Glu Arg Ala Gly Glu Arg Ala Met Val Val Lys Lys Trp Ala Pro
                325                 330                 335

Gln Gly Lys Ile Leu Lys His Gly Ser Ile Gly Gly Phe Val Ser His
                340                 345                 350

Cys Gly Trp Asn Ser Val Leu Glu Ser Ile Arg Phe Gly Val Pro Val
                355                 360                 365

Ile Gly Val Pro Met His Leu Asp Gln Pro Tyr Asn Ala Gly Leu Leu
                370                 375                 380

Glu Glu Ala Gly Ile Gly Val Glu Ala Lys Arg Asp Ala Asp Gly Lys
385                 390                 395                 400

Ile Gln Arg Asp Gln Val Ala Ser Leu Ile Lys Arg Val Val Glu
                405                 410                 415

Lys Thr Arg Glu Asp Ile Trp Lys Thr Val Arg Glu Met Arg Glu Val
                420                 425                 430

Leu Arg Arg Arg Asp Asp Asp Met Ile Asp Glu Met Val Ala Glu Ile
                435                 440                 445

Ser Val Val Leu Lys Ile
```

<210> SEQ ID NO 35
<211> LENGTH: 450
<212> TYPE: PRT
<213> ORGANISM: Momordica charantia

<400> SEQUENCE: 35

```
Met Asp Ala Arg Gln Gln Ala Glu His Thr Thr Ile Leu Met Leu
1               5                   10                  15

Pro Trp Val Gly Tyr Gly His Leu Ser Ala Tyr Leu Glu Leu Ala Lys
            20                  25                  30

Ala Leu Ser Arg Arg Asn Phe His Ile Tyr Tyr Cys Ser Thr Pro Val
        35                  40                  45

Asn Ile Glu Ser Ile Lys Pro Lys Leu Thr Ile Pro Cys Ser Ser Ile
50                  55                  60

Gln Phe Val Glu Leu His Leu Pro Phe Ser Asp Asp Leu Pro Pro Asn
65                  70                  75                  80

Leu His Thr Thr Asn Gly Leu Pro Ser His Leu Met Pro Ala Leu His
                    85                  90                  95

Gln Ala Phe Ser Ala Ala Ala Pro Leu Phe Glu Ala Ile Leu Gln Thr
            100                 105                 110

Leu Cys Pro His Leu Leu Ile Tyr Asp Ser Leu Gln Pro Trp Ala Pro
        115                 120                 125

Gln Ile Ala Ser Ser Leu Lys Ile Pro Ala Leu Asn Phe Asn Thr Thr
130                 135                 140

Gly Val Ser Val Ile Ala Arg Ala Leu His Thr Ile His His Pro Asp
145                 150                 155                 160

Ser Lys Phe Pro Leu Ser Glu Ile Val Leu His Asn Tyr Trp Lys Ala
                    165                 170                 175

Thr His Ala Thr Ala Asp Gly Ala Asn Pro Glu Lys Phe Arg Arg Asp
            180                 185                 190

Leu Glu Ala Leu Leu Cys Cys Leu His Ser Ser Cys Asn Ala Ile Leu
        195                 200                 205

Ile Asn Thr Phe Arg Glu Leu Glu Gly Glu Tyr Ile Asp Tyr Leu Ser
210                 215                 220

Leu Leu Leu Asn Lys Lys Val Thr Pro Ile Gly Pro Leu Val Tyr Glu
225                 230                 235                 240

Pro Asn Gln Asp Glu Glu Gln Asp Glu Glu Tyr Arg Ser Ile Lys Asn
                    245                 250                 255

Trp Leu Asp Lys Lys Glu Pro Tyr Ser Thr Ile Phe Val Ser Phe Gly
            260                 265                 270

Ser Glu Tyr Phe Pro Ser Asn Glu Glu Met Glu Glu Ile Ala Arg Gly
        275                 280                 285

Leu Glu Glu Ser Gly Ala Asn Phe Ile Trp Val Val Arg Phe His Lys
290                 295                 300

Leu Glu Asn Gly Asn Gly Ile Thr Glu Glu Gly Leu Leu Glu Arg Ala
305                 310                 315                 320

Gly Glu Arg Gly Met Val Ile Gln Gly Trp Ala Pro Gln Ala Arg Ile
                    325                 330                 335

Leu Arg His Gly Ser Ile Gly Gly Phe Val Ser His Cys Gly Trp Asn
            340                 345                 350

Ser Val Met Glu Ser Ile Ile Cys Gly Val Pro Val Ile Gly Val Pro
        355                 360                 365
```

-continued

Met Gly Leu Asp Gln Pro Tyr Asn Ala Gly Leu Val Glu Glu Ala Gly
            370                 375                 380

Val Gly Val Glu Ala Lys Arg Asp Pro Asp Gly Lys Ile Gln Arg His
385                 390                 395                 400

Glu Val Ser Lys Leu Ile Lys Gln Val Val Glu Lys Thr Arg Asp
                405                 410                 415

Asp Val Arg Lys Lys Val Ala Gln Met Ser Glu Ile Leu Arg Arg Lys
                420                 425                 430

Gly Asp Glu Lys Ile Asp Glu Met Val Ala Leu Ile Ser Leu Leu Leu
                435                 440                 445

Lys Gly
    450

<210> SEQ ID NO 36
<211> LENGTH: 457
<212> TYPE: PRT
<213> ORGANISM: Cucurbita moschata

<400> SEQUENCE: 36

Met Asp Ala Gln Lys Ala Val Asp Thr Pro Pro Thr Thr Val Leu Met
1               5                   10                  15

Leu Pro Trp Ile Gly Tyr Gly His Leu Ser Ala Tyr Leu Glu Leu Ala
                20                  25                  30

Lys Ala Leu Ser Arg Arg Asn Phe His Val Tyr Phe Cys Ser Thr Pro
            35                  40                  45

Val Asn Leu Asp Ser Ile Lys Pro Asn Leu Ile Pro Pro Pro Pro Ser
        50                  55                  60

Ile Gln Phe Val Asp Leu His Leu Pro Ser Ser Pro Glu Leu Pro Pro
65                  70                  75                  80

His Leu His Thr Thr Asn Gly Leu Pro Ser His Leu Lys Pro Thr Leu
                85                  90                  95

His Gln Ala Phe Ser Ala Ala Gln His Phe Glu Ala Ile Leu Gln
            100                 105                 110

Thr Leu Ser Pro His Leu Leu Ile Tyr Asp Ser Leu Gln Pro Trp Ala
            115                 120                 125

Pro Arg Ile Ala Ser Ser Leu Asn Ile Pro Ala Ile Asn Phe Asn Thr
        130                 135                 140

Thr Ala Val Ser Ile Ile Ala His Ala Leu His Ser Val His Tyr Pro
145                 150                 155                 160

Asp Ser Lys Phe Pro Phe Ser Asp Phe Val Leu His Asp Tyr Trp Lys
                165                 170                 175

Ala Lys Tyr Thr Thr Ala Asp Gly Ala Thr Ser Glu Lys Thr Arg Arg
            180                 185                 190

Gly Val Glu Ala Phe Leu Tyr Cys Leu Asn Ala Ser Cys Asp Val Val
        195                 200                 205

Leu Val Asn Ser Phe Arg Glu Leu Glu Gly Gly Tyr Met Asp Tyr Leu
210                 215                 220

Ser Val Leu Leu Lys Lys Val Ser Val Gly Pro Leu Val Tyr
225                 230                 235                 240

Glu Pro Ser Glu Gly Glu Glu Asp Glu Glu Tyr Trp Arg Ile Lys Lys
                245                 250                 255

Trp Leu Asp Glu Lys Glu Ala Leu Ser Thr Val Leu Val Ser Phe Gly
            260                 265                 270

Ser Glu Tyr Phe Pro Pro Lys Glu Glu Met Glu Glu Ile Ala His Gly
        275                 280                 285

```
Leu Glu Glu Ser Glu Ala Asn Phe Ile Trp Val Val Arg Phe Pro Lys
            290                 295                 300

Gly Glu Glu Ser Ser Ser Arg Gly Ile Glu Glu Ala Leu Pro Lys Gly
305                 310                 315                 320

Phe Val Glu Arg Ala Gly Glu Arg Ala Met Val Val Lys Lys Trp Ala
                325                 330                 335

Pro Gln Gly Lys Ile Leu Lys His Gly Ser Ile Gly Gly Phe Val Ser
                340                 345                 350

His Cys Gly Trp Asn Ser Val Leu Glu Ser Ile Arg Phe Gly Val Pro
            355                 360                 365

Val Ile Gly Ala Pro Met His Leu Asp Gln Pro Tyr Asn Ala Gly Leu
        370                 375                 380

Leu Glu Glu Ala Gly Ile Gly Val Glu Ala Lys Arg Asp Ala Asp Gly
385                 390                 395                 400

Lys Ile Gln Arg Asp Gln Val Ala Ser Leu Ile Lys Gln Val Val Val
                405                 410                 415

Glu Lys Thr Arg Glu Asp Ile Trp Lys Lys Val Arg Glu Met Arg Glu
            420                 425                 430

Val Leu Arg Arg Arg Asp Asp Asp Met Met Ile Asp Glu Met Val
            435                 440                 445

Ala Val Ile Ser Val Val Leu Lys Ile
            450                 455

<210> SEQ ID NO 37
<211> LENGTH: 492
<212> TYPE: PRT
<213> ORGANISM: Cucurbita maxima

<400> SEQUENCE: 37

Met Ser Ser Asn Leu Phe Leu Lys Ile Ser Ile Pro Phe Gly Arg Leu
1               5                   10                  15

Arg Asp Ser Ala Leu Asn Cys Ser Val Phe His Cys Lys Leu His Leu
                20                  25                  30

Ala Ile Ala Ile Ala Met Asp Ala Gln Gln Ala Ala Asn Lys Ser Pro
            35                  40                  45

Thr Ala Thr Thr Ile Phe Met Leu Pro Trp Ala Gly Tyr Gly His Leu
50                  55                  60

Ser Ala Tyr Leu Glu Leu Ala Lys Ala Leu Ser Thr Arg Asn Phe His
65                  70                  75                  80

Ile Tyr Phe Cys Ser Thr Pro Val Ser Leu Ala Ser Ile Lys Pro Arg
                85                  90                  95

Leu Ile Pro Ser Cys Ser Ser Ile Gln Phe Val Glu Leu His Leu Pro
            100                 105                 110

Ser Ser Asp Glu Phe Pro Pro His Leu His Thr Thr Asn Gly Leu Pro
        115                 120                 125

Ser Arg Leu Val Pro Thr Phe His Gln Ala Phe Ser Glu Ala Ala Gln
130                 135                 140

Thr Phe Glu Ala Phe Leu Gln Thr Leu Arg Pro His Leu Leu Ile Tyr
145                 150                 155                 160

Asp Ser Leu Gln Pro Trp Ala Pro Arg Ile Ala Ser Ser Leu Asn Ile
                165                 170                 175

Pro Ala Ile Asn Phe Phe Thr Ala Gly Ala Phe Ala Val Ser His Val
            180                 185                 190

Leu Arg Ala Phe His Tyr Pro Asp Ser Gln Phe Pro Ser Ser Asp Phe
```

```
            195                 200                 205
Val Leu His Ser Arg Trp Lys Ile Lys Asn Thr Thr Ala Glu Ser Pro
210                 215                 220

Thr Gln Ala Lys Leu Pro Lys Ile Gly Glu Ala Ile Gly Tyr Cys Leu
225                 230                 235                 240

Asn Ala Ser Arg Gly Val Ile Leu Thr Asn Ser Phe Arg Glu Leu Glu
                245                 250                 255

Gly Lys Tyr Ile Asp Tyr Leu Ser Val Ile Leu Lys Lys Arg Val Phe
            260                 265                 270

Pro Ile Gly Pro Leu Val Tyr Gln Pro Asn Gln Asp Glu Glu Asp Glu
        275                 280                 285

Asp Tyr Ser Arg Ile Lys Asn Trp Leu Asp Arg Lys Glu Ala Ser Ser
    290                 295                 300

Thr Val Leu Val Ser Phe Gly Ser Glu Phe Phe Leu Ser Lys Glu Glu
305                 310                 315                 320

Thr Glu Ala Ile Ala His Gly Leu Glu Gln Ser Glu Ala Asn Phe Ile
                325                 330                 335

Trp Gly Ile Arg Phe Pro Lys Gly Ala Lys Lys Asn Ala Ile Glu Glu
            340                 345                 350

Ala Leu Pro Glu Gly Phe Leu Glu Arg Ala Gly Gly Arg Ala Met Val
        355                 360                 365

Val Glu Glu Trp Val Pro Gln Gly Lys Ile Leu Lys His Gly Ser Ile
370                 375                 380

Gly Gly Phe Val Ser His Cys Gly Trp Asn Ser Ala Met Glu Ser Ile
385                 390                 395                 400

Val Cys Gly Val Pro Ile Ile Gly Ile Pro Met Gln Val Asp Gln Pro
                405                 410                 415

Phe Asn Ala Gly Ile Leu Glu Glu Ala Gly Val Gly Val Glu Ala Lys
            420                 425                 430

Arg Asp Ser Asp Gly Lys Ile Gln Arg Asp Glu Val Ala Lys Leu Ile
        435                 440                 445

Lys Glu Val Val Val Glu Arg Thr Arg Glu Asp Ile Arg Asn Lys Leu
    450                 455                 460

Glu Lys Ile Asn Glu Ile Leu Arg Ser Arg Arg Glu Glu Lys Leu Asp
465                 470                 475                 480

Glu Leu Ala Thr Glu Ile Ser Leu Leu Ser Arg Asn
                485                 490

<210> SEQ ID NO 38
<211> LENGTH: 455
<212> TYPE: PRT
<213> ORGANISM: Cucurbita moschata

<400> SEQUENCE: 38

Met Asp Ala Gln Gln Ala Ala Asn Lys Ser Pro Thr Ala Ser Thr Ile
1               5                   10                  15

Phe Met Leu Pro Trp Val Gly Tyr Gly His Leu Ser Ala Tyr Leu Glu
                20                  25                  30

Leu Ala Lys Ala Leu Ser Thr Arg Asn Phe His Val Tyr Phe Cys Ser
            35                  40                  45

Thr Pro Val Ser Leu Ala Ser Ile Lys Pro Arg Leu Ile Pro Ser Cys
        50                  55                  60

Ser Ser Ile Gln Phe Val Glu Leu His Leu Pro Ser Ser Asp Glu Phe
65                  70                  75                  80
```

Pro Pro His Leu His Thr Thr Asn Gly Leu Pro Ala His Leu Val Pro
            85                  90                  95

Thr Ile His Gln Ala Phe Ala Ala Ala Gln Thr Phe Glu Ala Phe
        100                 105                 110

Leu Gln Thr Leu Arg Pro His Leu Leu Ile Tyr Asp Ser Leu Gln Pro
        115                 120                 125

Trp Ala Pro Arg Ile Ala Ser Ser Leu Asn Ile Pro Ala Ile Asn Phe
130                 135                 140

Phe Thr Ala Gly Ala Phe Ala Val Ser His Val Leu Arg Ala Phe His
145                 150                 155                 160

Tyr Pro Asp Ser Gln Phe Pro Ser Ser Asp Phe Val Leu His Ser Arg
                165                 170                 175

Trp Lys Ile Lys Asn Thr Thr Ala Glu Ser Pro Thr Gln Val Lys Ile
        180                 185                 190

Pro Lys Ile Gly Glu Ala Ile Gly Tyr Cys Leu Asn Ala Ser Arg Gly
        195                 200                 205

Val Ile Leu Thr Asn Ser Phe Arg Glu Leu Gly Lys Tyr Ile Asp
    210                 215                 220

Tyr Leu Ser Val Ile Leu Lys Lys Arg Val Leu Pro Ile Gly Pro Leu
225                 230                 235                 240

Val Tyr Gln Pro Asn Gln Asp Glu Glu Asp Tyr Ser Arg Ile
                245                 250                 255

Lys Asn Trp Leu Asp Arg Lys Glu Ala Ser Ser Thr Val Leu Val Ser
            260                 265                 270

Phe Gly Ser Glu Phe Phe Leu Ser Lys Glu Glu Thr Glu Ala Ile Ala
        275                 280                 285

His Gly Leu Glu Gln Ser Glu Ala Asn Phe Ile Trp Gly Ile Arg Phe
    290                 295                 300

Pro Lys Gly Ala Lys Lys Asn Ala Ile Glu Glu Ala Leu Pro Glu Gly
305                 310                 315                 320

Phe Leu Glu Arg Val Gly Gly Arg Ala Met Val Val Glu Glu Trp Val
                325                 330                 335

Pro Gln Gly Lys Ile Leu Lys His Gly Asn Ile Gly Gly Phe Val Ser
        340                 345                 350

His Cys Gly Trp Asn Ser Ala Met Glu Ser Ile Met Cys Gly Val Pro
    355                 360                 365

Val Ile Gly Ile Pro Met Gln Val Asp Gln Pro Phe Asn Ala Gly Ile
    370                 375                 380

Leu Glu Glu Ala Gly Val Gly Val Glu Ala Lys Arg Asp Ser Asp Gly
385                 390                 395                 400

Lys Ile Gln Arg Asp Glu Val Ala Lys Leu Ile Lys Glu Val Val Val
                405                 410                 415

Glu Arg Thr Arg Glu Asp Ile Arg Asn Lys Leu Glu Glu Ile Asn Glu
            420                 425                 430

Ile Leu Arg Thr Arg Arg Glu Glu Lys Leu Asp Glu Leu Ala Thr Glu
        435                 440                 445

Ile Ser Leu Leu Cys Lys Asn
    450                 455

<210> SEQ ID NO 39
<211> LENGTH: 462
<212> TYPE: PRT
<213> ORGANISM: Corchorus capsularis

<400> SEQUENCE: 39

-continued

```
Met Asp Ser Lys Gln Lys Lys Met Ser Val Leu Met Phe Pro Trp Leu
1               5                   10                  15

Ala Tyr Gly His Ile Ser Pro Phe Leu Glu Leu Ala Lys Lys Leu Ser
            20                  25                  30

Lys Arg Asn Phe His Thr Phe Phe Ser Thr Pro Ile Asn Leu Asn
        35                  40                  45

Ser Ile Lys Ser Lys Leu Ser Pro Lys Tyr Ala Gln Ser Ile Gln Phe
    50                  55                  60

Val Glu Leu His Leu Pro Ser Leu Pro Asp Leu Pro Pro His Tyr His
65                  70                  75                  80

Thr Thr Asn Gly Leu Pro Pro His Leu Met Asn Thr Leu Lys Lys Ala
                85                  90                  95

Phe Asp Met Ser Ser Leu Gln Phe Ser Lys Ile Leu Lys Thr Leu Asn
            100                 105                 110

Pro Asp Leu Leu Val Tyr Asp Phe Ile Gln Pro Trp Ala Pro Leu Leu
        115                 120                 125

Ala Leu Ser Asn Lys Ile Pro Ala Val His Phe Leu Cys Thr Ser Ala
    130                 135                 140

Ala Met Ser Ser Phe Ser Val His Ala Phe Lys Lys Pro Cys Glu Asp
145                 150                 155                 160

Phe Pro Phe Pro Asn Ile Tyr Val His Gly Asn Phe Met Asn Ala Lys
                165                 170                 175

Phe Asn Asn Met Glu Asn Cys Ser Ser Asp Asp Ser Ile Ser Asp Gln
            180                 185                 190

Asp Arg Val Leu Gln Cys Phe Glu Arg Ser Thr Lys Ile Ile Leu Val
        195                 200                 205

Lys Thr Phe Glu Glu Leu Glu Gly Lys Phe Met Asp Tyr Leu Ser Val
    210                 215                 220

Leu Leu Asn Lys Lys Ile Val Pro Thr Gly Pro Leu Thr Gln Asp Pro
225                 230                 235                 240

Asn Glu Asp Glu Gly Asp Asp Glu Arg Thr Lys Leu Leu Leu Glu
                245                 250                 255

Trp Leu Asn Lys Lys Ser Lys Ser Ser Thr Val Phe Val Ser Phe Gly
            260                 265                 270

Ser Glu Tyr Phe Leu Ser Lys Glu Glu Arg Glu Glu Ile Ala Tyr Gly
        275                 280                 285

Leu Glu Leu Ser Lys Val Asn Phe Ile Trp Val Ile Arg Phe Pro Leu
    290                 295                 300

Gly Glu Asn Lys Thr Asn Leu Glu Glu Ala Leu Pro Gln Gly Phe Leu
305                 310                 315                 320

Gln Arg Val Ser Glu Arg Gly Leu Val Val Glu Asn Trp Ala Pro Gln
                325                 330                 335

Ala Lys Ile Leu Gln His Ser Ser Ile Gly Gly Phe Val Ser His Cys
            340                 345                 350

Gly Trp Ser Ser Val Met Glu Ser Leu Lys Phe Gly Val Pro Ile Ile
        355                 360                 365

Ala Ile Pro Met His Leu Asp Gln Pro Leu Asn Ala Arg Leu Val Val
    370                 375                 380

Asp Val Gly Val Gly Leu Glu Val Ile Arg Asn His Gly Ser Leu Glu
385                 390                 395                 400

Arg Glu Glu Ile Ala Lys Leu Ile Lys Glu Val Val Leu Gly Asn Gly
                405                 410                 415
```

```
Asn Asp Gly Glu Ile Val Arg Arg Lys Ala Arg Glu Met Ser Asn His
            420                 425                 430

Ile Lys Lys Lys Gly Glu Lys Asp Met Asp Glu Leu Val Glu Glu Leu
            435                 440                 445

Met Leu Ile Cys Lys Met Lys Pro Asn Ser Cys His Leu Ser
450                 455                 460

<210> SEQ ID NO 40
<211> LENGTH: 448
<212> TYPE: PRT
<213> ORGANISM: Ziziphus jujuba

<400> SEQUENCE: 40

Met Met Glu Arg Gln Arg Ser Ile Lys Val Leu Met Phe Pro Trp Leu
1               5                   10                  15

Ala His Gly His Ile Ser Pro Phe Leu Glu Leu Ala Lys Arg Leu Thr
            20                  25                  30

Asp Arg Asn Phe Gln Ile Tyr Phe Cys Ser Thr Pro Val Asn Leu Thr
        35                  40                  45

Ser Val Lys Pro Lys Leu Ser Gln Lys Tyr Ser Ser Ile Lys Leu
50                  55                  60

Val Glu Leu His Leu Pro Ser Leu Pro Asp Leu Pro Pro His Tyr His
65                  70                  75                  80

Thr Thr Asn Gly Leu Ala Leu Asn Leu Ile Pro Thr Leu Lys Lys Ala
                85                  90                  95

Phe Asp Met Ser Ser Ser Ser Phe Ser Thr Ile Leu Ser Thr Ile Lys
            100                 105                 110

Pro Asp Leu Leu Ile Tyr Asp Phe Leu Gln Pro Trp Ala Pro Gln Leu
        115                 120                 125

Ala Ser Cys Met Asn Ile Pro Ala Val Asn Phe Leu Ser Ala Gly Ala
130                 135                 140

Ser Met Val Ser Phe Val Leu His Ser Ile Lys Tyr Asn Gly Asp Asp
145                 150                 155                 160

His Asp Asp Glu Phe Leu Thr Thr Glu Leu His Leu Ser Asp Ser Met
                165                 170                 175

Glu Ala Lys Phe Ala Glu Met Thr Glu Ser Ser Pro Asp Glu His Ile
            180                 185                 190

Asp Arg Ala Val Thr Cys Leu Glu Arg Ser Asn Ser Leu Ile Leu Ile
        195                 200                 205

Lys Ser Phe Arg Glu Leu Glu Gly Lys Tyr Leu Asp Tyr Leu Ser Leu
210                 215                 220

Ser Phe Ala Lys Lys Val Pro Ile Gly Pro Leu Val Ala Gln Asp
225                 230                 235                 240

Thr Asn Pro Glu Asp Asp Ser Met Asp Ile Ile Asn Trp Leu Asp Lys
                245                 250                 255

Lys Glu Lys Ser Ser Thr Val Phe Val Ser Phe Gly Ser Glu Tyr Tyr
            260                 265                 270

Leu Thr Asn Glu Glu Met Glu Glu Ile Ala Tyr Gly Leu Glu Leu Ser
        275                 280                 285

Lys Val Asn Phe Ile Trp Val Arg Phe Pro Leu Gly Gln Lys Met
290                 295                 300

Ala Val Glu Glu Ala Leu Pro Lys Gly Phe Leu Glu Arg Val Gly Glu
305                 310                 315                 320

Lys Gly Met Val Val Glu Asp Trp Ala Pro Gln Met Lys Ile Leu Gly
                325                 330                 335
```

```
His Ser Ser Ile Gly Gly Phe Val Ser His Cys Gly Trp Ser Ser Leu
                340                 345                 350

Met Glu Ser Leu Lys Leu Gly Val Pro Ile Ile Ala Met Pro Met Gln
                355                 360                 365

Leu Asp Gln Pro Ile Asn Ala Lys Leu Val Glu Arg Ser Gly Val Gly
            370                 375                 380

Leu Glu Val Lys Arg Asp Lys Asn Gly Arg Ile Glu Arg Glu Tyr Leu
385                 390                 395                 400

Ala Lys Val Ile Arg Glu Ile Val Glu Lys Ala Arg Gln Asp Ile
                405                 410                 415

Glu Lys Lys Ala Arg Glu Met Ser Asn Ile Ile Thr Glu Lys Gly Glu
                420                 425                 430

Glu Glu Ile Asp Asn Val Val Glu Leu Ala Lys Leu Cys Gly Met
            435                 440                 445

<210> SEQ ID NO 41
<211> LENGTH: 446
<212> TYPE: PRT
<213> ORGANISM: Vitis vinifera

<400> SEQUENCE: 41

Met Asp Ala Arg Gln Ser Asp Gly Ile Ser Val Leu Met Phe Pro Trp
1               5                   10                  15

Leu Ala His Gly His Ile Ser Pro Phe Leu Gln Leu Ala Lys Lys Leu
                20                  25                  30

Ser Lys Arg Asn Phe Ser Ile Tyr Phe Cys Ser Thr Pro Val Asn Leu
            35                  40                  45

Asp Pro Ile Lys Gly Lys Leu Ser Glu Ser Tyr Ser Leu Ser Ile Gln
50                  55                  60

Leu Val Lys Leu His Leu Pro Ser Leu Pro Glu Leu Pro Pro Gln Tyr
65                  70                  75                  80

His Thr Thr Asn Gly Leu Pro Pro His Leu Met Pro Thr Leu Lys Met
                85                  90                  95

Ala Phe Asp Met Ala Ser Pro Asn Phe Ser Asn Ile Leu Lys Thr Leu
                100                 105                 110

His Pro Asp Leu Leu Ile Tyr Asp Phe Leu Gln Pro Trp Ala Pro Ala
            115                 120                 125

Ala Ala Ser Ser Leu Asn Ile Pro Ala Val Gln Phe Leu Ser Thr Gly
        130                 135                 140

Ala Thr Leu Gln Ser Phe Leu Ala His Arg His Arg Lys Pro Gly Ile
145                 150                 155                 160

Glu Phe Pro Phe Gln Glu Ile His Leu Pro Asp Tyr Glu Ile Gly Arg
                165                 170                 175

Leu Asn Arg Phe Leu Glu Pro Ser Ala Gly Arg Ile Ser Asp Arg Asp
            180                 185                 190

Arg Ala Asn Gln Cys Leu Glu Arg Ser Arg Phe Ser Leu Ile Lys
        195                 200                 205

Thr Phe Arg Glu Ile Glu Ala Lys Tyr Leu Asp Tyr Val Ser Asp Leu
210                 215                 220

Thr Lys Lys Lys Met Val Thr Val Gly Pro Leu Gln Asp Pro Glu
225                 230                 235                 240

Asp Glu Asp Glu Ala Thr Asp Ile Val Glu Trp Leu Asn Lys Lys Cys
                245                 250                 255

Glu Ala Ser Ala Val Phe Val Ser Phe Gly Ser Glu Tyr Phe Val Ser
```

```
            260                 265                 270
Lys Glu Glu Met Glu Glu Ile Ala His Gly Leu Glu Leu Ser Asn Val
            275                 280                 285

Asp Phe Ile Trp Val Val Arg Phe Pro Met Gly Glu Lys Ile Arg Leu
        290                 295                 300

Glu Asp Ala Leu Pro Pro Gly Phe Leu His Arg Leu Gly Asp Arg Gly
305                 310                 315                 320

Met Val Val Glu Gly Trp Ala Pro Gln Arg Lys Ile Leu Gly His Ser
                325                 330                 335

Ser Ile Gly Gly Phe Val Ser His Cys Gly Trp Ser Ser Val Met Glu
            340                 345                 350

Gly Met Lys Phe Gly Val Pro Ile Ile Ala Met Pro Met His Leu Asp
        355                 360                 365

Gln Pro Ile Asn Ala Lys Leu Val Glu Ala Val Gly Val Gly Arg Glu
            370                 375                 380

Val Lys Arg Asp Glu Asn Arg Lys Leu Glu Arg Glu Ile Ala Lys
385                 390                 395                 400

Val Ile Lys Glu Val Val Gly Glu Lys Asn Gly Glu Asn Val Arg Arg
                405                 410                 415

Lys Ala Arg Glu Leu Ser Glu Thr Leu Arg Lys Lys Gly Asp Glu Glu
            420                 425                 430

Ile Asp Val Val Glu Glu Leu Lys Gln Leu Cys Ser Tyr
        435                 440                 445

<210> SEQ ID NO 42
<211> LENGTH: 456
<212> TYPE: PRT
<213> ORGANISM: Juglans regia

<400> SEQUENCE: 42

Met Asp Thr Ala Arg Lys Arg Ile Arg Val Val Met Leu Pro Trp Leu
1               5                   10                  15

Ala His Gly His Ile Ser Pro Phe Leu Glu Leu Ser Lys Lys Leu Ala
                20                  25                  30

Lys Arg Asn Phe His Ile Tyr Phe Cys Ser Thr Pro Val Asn Leu Ser
            35                  40                  45

Ser Ile Lys Pro Lys Leu Ser Gly Lys Tyr Ser Arg Ser Ile Gln Leu
        50                  55                  60

Val Glu Leu His Leu Pro Ser Leu Pro Glu Leu Pro Pro Gln Tyr His
65                  70                  75                  80

Thr Thr Lys Gly Leu Pro Pro His Leu Asn Ala Thr Leu Lys Arg Ala
                85                  90                  95

Phe Asp Met Ala Gly Pro His Phe Ser Asn Ile Leu Lys Thr Leu Ser
            100                 105                 110

Pro Asp Leu Leu Ile Tyr Asp Phe Leu Gln Pro Trp Ala Pro Ala Ile
        115                 120                 125

Ala Ala Ser Gln Asn Ile Pro Ala Ile Asn Phe Leu Ser Thr Gly Ala
    130                 135                 140

Ala Met Thr Ser Phe Val Leu His Ala Met Lys Lys Pro Gly Asp Glu
145                 150                 155                 160

Phe Pro Phe Pro Glu Ile His Leu Asp Glu Cys Met Lys Thr Arg Phe
                165                 170                 175

Val Asp Leu Pro Glu Asp His Ser Pro Ser Asp His Asn His Ile
            180                 185                 190
```

```
Ser Asp Lys Asp Arg Ala Leu Lys Cys Phe Glu Arg Ser Gly Phe
            195                 200                 205

Val Met Met Lys Thr Phe Glu Glu Leu Glu Gly Lys Tyr Ile Asn Phe
210                 215                 220

Leu Ser His Leu Met Gln Lys Lys Ile Val Pro Val Gly Pro Leu Val
225                 230                 235                 240

Gln Asn Pro Val Arg Gly Asp His Glu Lys Ala Lys Thr Leu Glu Trp
            245                 250                 255

Leu Asp Lys Arg Lys Gln Ser Ser Ala Val Phe Val Ser Phe Gly Thr
            260                 265                 270

Glu Tyr Phe Leu Ser Lys Glu Glu Met Glu Glu Ile Ala Tyr Gly Leu
            275                 280                 285

Glu Leu Ser Asn Val Asn Phe Ile Trp Val Val Arg Phe Pro Glu Gly
290                 295                 300

Glu Lys Val Lys Leu Glu Glu Ala Leu Pro Glu Gly Phe Leu Gln Arg
305                 310                 315                 320

Val Gly Glu Lys Gly Met Val Val Glu Gly Trp Ala Pro Gln Ala Lys
            325                 330                 335

Ile Leu Met His Pro Ser Ile Gly Gly Phe Val Ser His Cys Gly Trp
            340                 345                 350

Ser Ser Val Met Glu Ser Ile Asp Phe Gly Val Pro Ile Val Ala Ile
355                 360                 365

Pro Met Gln Leu Asp Gln Pro Val Asn Ala Lys Val Val Glu Gln Ala
            370                 375                 380

Gly Val Gly Val Glu Val Lys Arg Asp Arg Asp Gly Lys Leu Glu Arg
385                 390                 395                 400

Glu Glu Val Ala Thr Val Ile Arg Glu Val Val Met Gly Asn Ile Gly
                405                 410                 415

Glu Ser Val Arg Lys Lys Glu Arg Glu Met Arg Asp Asn Ile Arg Lys
            420                 425                 430

Lys Gly Glu Glu Lys Met Asp Gly Val Ala Gln Glu Leu Val Gln Leu
            435                 440                 445

Tyr Gly Asn Gly Ile Lys Asn Val
    450                 455

<210> SEQ ID NO 43
<211> LENGTH: 456
<212> TYPE: PRT
<213> ORGANISM: Hevea brasiliensis

<400> SEQUENCE: 43

Met Glu Thr Leu Gln Arg Arg Lys Ile Ser Val Leu Met Phe Pro Trp
1               5                   10                  15

Leu Ala His Gly His Leu Ser Pro Phe Leu Glu Leu Ser Lys Lys Leu
            20                  25                  30

Asn Lys Arg Asn Phe His Val Tyr Phe Cys Ser Thr Pro Val Asn Leu
        35                  40                  45

Asp Ser Ile Lys Pro Lys Leu Ser Ala Glu Tyr Ser Phe Ser Ile Gln
    50                  55                  60

Leu Val Glu Leu His Leu Pro Ser Ser Pro Glu Leu Pro Leu His Tyr
65                  70                  75                  80

His Thr Thr Asn Gly Leu Pro Pro His Leu Met Lys Asn Leu Lys Asn
                85                  90                  95

Ala Phe Asp Met Ala Ser Ser Phe Phe Asn Ile Leu Lys Thr Leu
            100                 105                 110
```

Lys Pro Asp Leu Leu Ile Tyr Asp Phe Ile Gln Pro Trp Ala Pro Ala
            115                 120                 125

Leu Ala Ser Ser Leu Asn Ile Pro Ala Val Asn Phe Leu Cys Thr Ser
130                 135                 140

Met Ala Met Ser Cys Phe Gly Leu His Leu Asn Asn Gln Glu Ala Lys
145                 150                 155                 160

Phe Pro Phe Pro Gly Ile Tyr Pro Arg Asp Tyr Met Arg Met Lys Val
                165                 170                 175

Phe Gly Ala Leu Glu Ser Ser Asn Asp Ile Lys Asp Gly Glu Arg
            180                 185                 190

Ala Gly Arg Cys Met Asp Gln Ser Phe His Leu Ile Leu Ala Lys Thr
            195                 200                 205

Phe Arg Glu Leu Glu Gly Lys Tyr Ile Asp Tyr Leu Ser Val Lys Leu
            210                 215                 220

Met Lys Lys Ile Val Pro Val Gly Pro Leu Val Gln Asp Pro Ile Phe
225                 230                 235                 240

Glu Asp Asp Glu Lys Ile Met Asp His His Gln Val Ile Lys Trp Leu
                245                 250                 255

Glu Lys Lys Glu Arg Leu Ser Thr Val Phe Val Ser Phe Gly Thr Glu
            260                 265                 270

Tyr Phe Leu Ser Thr Glu Glu Met Glu Glu Ile Ala Tyr Gly Leu Glu
            275                 280                 285

Leu Ser Lys Ala His Phe Ile Trp Val Val Arg Phe Pro Thr Gly Glu
            290                 295                 300

Lys Ile Asn Leu Glu Glu Ser Leu Pro Lys Arg Tyr Leu Glu Arg Val
305                 310                 315                 320

Gln Glu Arg Gly Lys Ile Val Glu Gly Trp Ala Pro Gln Gln Lys Ile
            325                 330                 335

Leu Arg His Ser Ser Ile Gly Gly Phe Val Ser His Cys Gly Trp Ser
            340                 345                 350

Ser Ile Met Glu Ser Met Lys Phe Gly Val Pro Ile Ile Ala Met Pro
            355                 360                 365

Met Asn Leu Asp Gln Pro Val Asn Ser Arg Ile Val Glu Asp Ala Gly
            370                 375                 380

Val Gly Ile Glu Val Arg Arg Asn Lys Ser Gly Glu Leu Glu Arg Glu
385                 390                 395                 400

Glu Ile Ala Lys Thr Ile Arg Lys Val Val Val Glu Lys Asp Gly Lys
                405                 410                 415

Asn Val Ser Arg Lys Ala Arg Glu Met Ser Asp Thr Ile Arg Lys Lys
            420                 425                 430

Gly Glu Glu Glu Ile Asp Gly Val Val Asp Glu Leu Leu Gln Leu Cys
            435                 440                 445

Asp Val Lys Thr Asn Tyr Leu Gln
    450                 455

<210> SEQ ID NO 44
<211> LENGTH: 461
<212> TYPE: PRT
<213> ORGANISM: Manihot esculenta

<400> SEQUENCE: 44

Met Ala Thr Ala Gln Thr Arg Lys Ile Ser Val Leu Met Phe Pro Trp
1               5                   10                  15

Leu Ala His Gly His Leu Ser Pro Phe Leu Glu Leu Ser Lys Lys Leu

```
                20                  25                  30
Ala Asn Arg Asn Phe His Val Tyr Phe Cys Ser Thr Pro Val Asn Leu
            35                  40                  45
Asp Ser Ile Lys Pro Lys Leu Ser Pro Glu Tyr His Phe Ser Ile Gln
            50                  55                  60
Phe Val Glu Leu His Leu Pro Ser Ser Pro Glu Leu Pro Ser His Tyr
65                  70                  75                  80
His Thr Thr Asn Gly Leu Pro Pro His Leu Met Lys Thr Leu Lys Lys
                85                  90                  95
Ala Phe Asp Met Ala Ser Ser Phe Phe Asn Ile Leu Lys Thr Leu
            100                 105                 110
Asn Pro Asp Leu Leu Ile Tyr Asp Phe Leu Gln Pro Trp Ala Pro Ala
            115                 120                 125
Leu Ala Ser Ser Leu Asn Ile Pro Ala Val Asn Phe Leu Cys Ser Ser
            130                 135                 140
Met Ala Met Ser Cys Phe Gly Leu Asn Leu Asn Lys Asn Lys Glu Ile
145                 150                 155                 160
Lys Phe Leu Phe Pro Glu Ile Tyr Pro Arg Asp Tyr Met Glu Met Lys
                165                 170                 175
Leu Phe Arg Val Phe Glu Ser Ser Asn Gln Ile Lys Asp Gly Glu
            180                 185                 190
Arg Ala Gly Arg Cys Ile Asp Gln Ser Phe His Val Ile Leu Ala Lys
            195                 200                 205
Thr Phe Arg Glu Leu Glu Gly Lys Tyr Ile Asp Tyr Val Ser Val Lys
            210                 215                 220
Cys Asn Lys Lys Ile Val Pro Val Gly Pro Leu Val Glu Asp Thr Ile
225                 230                 235                 240
His Glu Asp Asp Glu Lys Thr Met Asp His His His His His Asp
                245                 250                 255
Glu Val Ile Lys Trp Leu Glu Lys Lys Glu Arg Ser Thr Thr Val Phe
            260                 265                 270
Val Ser Phe Gly Ser Glu Tyr Phe Leu Ser Lys Glu Glu Met Glu Glu
            275                 280                 285
Ile Ala His Gly Leu Glu Leu Ser Lys Val Asn Phe Ile Trp Val Val
            290                 295                 300
Arg Phe Pro Lys Gly Glu Lys Ile Asn Leu Glu Glu Ser Leu Pro Glu
305                 310                 315                 320
Gly Tyr Leu Glu Arg Ile Gln Glu Arg Gly Lys Ile Val Glu Gly Trp
                325                 330                 335
Ala Pro Gln Arg Lys Ile Leu Gly His Ser Ser Ile Gly Gly Phe Val
            340                 345                 350
Ser His Cys Gly Trp Ser Ser Ile Met Glu Ser Met Lys Leu Gly Val
            355                 360                 365
Pro Ile Ile Ala Met Pro Met Asn Leu Asp Gln Pro Ile Asn Ser Arg
            370                 375                 380
Ile Val Glu Ala Ala Gly Val Gly Ile Glu Val Ser Arg Asn Gln Ser
385                 390                 395                 400
Gly Glu Leu Glu Arg Glu Met Ala Lys Thr Ile Arg Lys Val Val
                405                 410                 415
Val Glu Arg Glu Gly Val Tyr Val Arg Arg Lys Ala Arg Glu Met Ser
            420                 425                 430
Asp Val Leu Arg Lys Lys Gly Glu Glu Ile Asp Gly Val Val Asp
            435                 440                 445
```

Glu Leu Val Gln Leu Cys Asp Met Lys Thr Asn Tyr Leu
    450                 455                 460

<210> SEQ ID NO 45
<211> LENGTH: 452
<212> TYPE: PRT
<213> ORGANISM: Cephalotus follicularis

<400> SEQUENCE: 45

Met Asp Leu Lys Arg Arg Ser Ile Arg Val Leu Met Leu Pro Trp Leu
1               5                   10                  15

Ala His Gly His Ile Ser Pro Phe Leu Glu Leu Ala Lys Lys Leu Thr
            20                  25                  30

Asn Arg Asn Phe Leu Ile Tyr Phe Cys Ser Thr Pro Ile Asn Leu Asn
        35                  40                  45

Ser Ile Lys Pro Lys Leu Ser Ser Lys Tyr Ser Phe Ser Ile Gln Leu
    50                  55                  60

Val Glu Leu His Leu Pro Ser Leu Pro Glu Leu Pro Pro His Tyr His
65                  70                  75                  80

Thr Thr Asn Gly Leu Pro Leu His Leu Met Asn Thr Leu Lys Thr Ala
                85                  90                  95

Phe Asp Met Ala Ser Pro Ser Phe Leu Asn Ile Leu Lys Thr Leu Lys
            100                 105                 110

Pro Asp Leu Leu Ile Cys Asp His Leu Gln Pro Trp Ala Pro Ser Leu
        115                 120                 125

Ala Ser Ser Leu Asn Ile Pro Ala Ile Ile Phe Pro Thr Asn Ser Ala
    130                 135                 140

Ile Met Met Ala Phe Ser Leu His His Ala Lys Asn Pro Gly Glu Glu
145                 150                 155                 160

Phe Pro Phe Pro Ser Ile Asn Ile Asn Asp Asp Met Val Lys Ser Ile
                165                 170                 175

Asn Phe Leu His Ser Ala Ser Asn Gly Leu Thr Asp Met Asp Arg Val
            180                 185                 190

Leu Gln Cys Leu Glu Arg Ser Ser Asn Thr Met Leu Leu Lys Thr Phe
        195                 200                 205

Arg Gln Leu Glu Ala Lys Tyr Val Asp Tyr Ser Ser Ala Leu Leu Lys
    210                 215                 220

Lys Lys Ile Val Leu Ala Gly Pro Leu Val Gln Val Pro Asp Asn Glu
225                 230                 235                 240

Asp Glu Lys Ile Glu Ile Ile Lys Trp Leu Asp Ser Arg Gly Gln Ser
                245                 250                 255

Ser Thr Val Phe Val Ser Phe Gly Ser Glu Tyr Phe Leu Ser Lys Glu
            260                 265                 270

Glu Arg Glu Asp Ile Ala His Gly Leu Glu Leu Ser Lys Val Asn Phe
        275                 280                 285

Ile Trp Val Val Arg Phe Pro Val Gly Glu Lys Val Lys Leu Glu Glu
    290                 295                 300

Ala Leu Pro Asn Gly Phe Ala Glu Arg Ile Gly Glu Arg Gly Leu Val
305                 310                 315                 320

Val Glu Gly Trp Ala Pro Gln Ala Met Ile Leu Ser His Ser Ser Ile
                325                 330                 335

Gly Gly Phe Val Ser His Cys Gly Trp Ser Ser Met Met Glu Ser Met
            340                 345                 350

Lys Phe Gly Val Pro Ile Ile Ala Met Pro Met His Ile Asp Gln Pro

```
                355                 360                 365
Leu Asn Ala Arg Leu Val Glu Asp Val Gly Val Gly Leu Glu Ile Lys
    370                 375                 380

Arg Asn Lys Asp Gly Arg Phe Glu Arg Glu Leu Ala Arg Val Ile
385                 390                 395                 400

Lys Glu Val Leu Val Tyr Lys Asn Gly Asp Ala Val Arg Ser Lys Ala
                405                 410                 415

Arg Glu Met Ser Glu His Ile Lys Lys Asn Gly Asp Gln Glu Ile Asp
                420                 425                 430

Gly Val Ala Asp Ala Leu Val Lys Leu Cys Glu Met Lys Thr Asn Ser
                435                 440                 445

Leu Asn Gln Asp
    450

<210> SEQ ID NO 46
<211> LENGTH: 451
<212> TYPE: PRT
<213> ORGANISM: Coffea Arabica

<400> SEQUENCE: 46

Met Glu Asn His Ala Thr Phe Asn Val Leu Met Leu Pro Trp Leu Ala
1               5                   10                  15

His Gly His Val Ser Pro Tyr Leu Glu Leu Ala Lys Lys Leu Thr Ala
            20                  25                  30

Arg Asn Phe Asn Val Tyr Leu Cys Ser Ser Pro Ala Thr Leu Ser Ser
        35                  40                  45

Val Arg Ser Lys Leu Thr Glu Lys Phe Ser Gln Ser Ile His Leu Val
    50                  55                  60

Glu Leu His Leu Pro Lys Leu Pro Glu Leu Pro Ala Glu Tyr His Thr
65                  70                  75                  80

Thr Asn Gly Leu Pro Pro His Leu Met Pro Thr Leu Lys Asp Ala Phe
                85                  90                  95

Asp Met Ala Lys Pro Asn Phe Cys Asn Val Leu Lys Ser Leu Lys Pro
                100                 105                 110

Asp Leu Leu Ile Tyr Asp Leu Leu Gln Pro Trp Ala Pro Glu Ala Ala
            115                 120                 125

Ser Ala Phe Asn Ile Pro Ala Val Val Phe Ile Ser Ser Ser Ala Thr
    130                 135                 140

Met Thr Ser Phe Gly Leu His Phe Phe Lys Asn Pro Gly Thr Lys Tyr
145                 150                 155                 160

Pro Tyr Gly Asn Ala Ile Phe Tyr Arg Asp Tyr Glu Ser Val Phe Val
                165                 170                 175

Glu Asn Leu Thr Arg Arg Asp Arg Asp Thr Tyr Arg Val Ile Asn Cys
                180                 185                 190

Met Glu Arg Ser Ser Lys Ile Ile Leu Ile Lys Gly Phe Asn Glu Ile
            195                 200                 205

Glu Gly Lys Tyr Phe Asp Tyr Phe Ser Cys Leu Thr Gly Lys Lys Val
    210                 215                 220

Val Pro Val Gly Pro Leu Val Gln Asp Pro Val Leu Asp Asp Glu Asp
225                 230                 235                 240

Cys Arg Ile Met Gln Trp Leu Asn Lys Lys Glu Lys Gly Ser Thr Val
                245                 250                 255

Phe Val Ser Phe Gly Ser Glu Tyr Phe Leu Ser Lys Lys Asp Met Glu
                260                 265                 270
```

```
Glu Ile Ala His Gly Leu Glu Val Ser Asn Val Asp Phe Ile Trp Val
            275                 280                 285

Val Arg Phe Pro Lys Gly Glu Asn Ile Val Ile Glu Glu Thr Leu Pro
    290                 295                 300

Lys Gly Phe Phe Glu Arg Val Gly Glu Arg Gly Leu Val Asn Gly
305                 310                 315                 320

Trp Ala Pro Gln Ala Lys Ile Leu Thr His Pro Asn Val Gly Gly Phe
                325                 330                 335

Val Ser His Cys Gly Trp Asn Ser Val Met Glu Ser Met Lys Phe Gly
            340                 345                 350

Leu Pro Ile Ile Ala Met Pro Met His Leu Asp Gln Pro Ile Asn Ala
        355                 360                 365

Arg Leu Ile Glu Glu Val Gly Ala Gly Val Glu Val Leu Arg Asp Ser
    370                 375                 380

Lys Gly Lys Leu His Arg Glu Arg Met Ala Glu Thr Ile Asn Lys Val
385                 390                 395                 400

Met Lys Glu Ala Ser Gly Glu Ser Val Arg Lys Ala Arg Glu Leu
                405                 410                 415

Gln Glu Lys Leu Glu Leu Lys Gly Asp Glu Glu Ile Asp Asp Val Val
                420                 425                 430

Lys Glu Leu Val Gln Leu Cys Ala Thr Lys Asn Lys Arg Asn Gly Leu
        435                 440                 445

His Tyr Tyr
    450

<210> SEQ ID NO 47
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 47

Gly Ser Gly Gly Ser Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 48

Gly Ser Gly Gly Ser Gly Gly Ser Gly
1               5
```

PRODUCTION OF STEVIOL GLYCOSIDES THROUGH WHOLE CELL BIOTRANSFORMATION OF STEVIOL GLYCOSIDE INTERMEDIATES

PRIORITY

This application claims priority to, and the benefit of, U.S. Provisional Application No. 62/698,617 filed Jul. 16, 2018, which is hereby incorporated by reference in its entirety.

BACKGROUND

Glycosyltransferases of small molecules are encoded by a large multigene family in the plant kingdom. These enzymes transfer sugars from nucleotide sugars to a wide range of secondary metabolites, thereby altering the physical and chemical properties of the acceptor molecule. For example, steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in stevia leaves, composing approximately 10% to 20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other steviol glycosides are present at small or trace amounts, including rebaudioside B, D, E, F, G, H, I, J, K, L, M and O, dulcoside B, steviolbioside and rubusoside.

The minor glycosylation product rebaudioside M (RebM) is estimated to be about 200-350 times more potent than sucrose, and is described as possessing a clean, sweet taste with a slightly bitter or licorice aftertaste. Prakash I. et al., *Development of Next Generation Stevia Sweetener: Rebaudioside M*, Foods 3(1), 162-175 (2014). While RebM is of great interest to the global food industry, its low prevalence in stevia extract necessitates innovative processes for its synthesis.

There remains a need for economical methods for producing high value glycosides that are minor products of natural plant extract.

SUMMARY OF THE INVENTION

In various aspects and embodiments, the invention provides microbial cells and methods for producing advanced glycosylation products from lower glycosylated intermediates. The microbial cell expresses one or more UDP-dependent glycosyltransferase enzymes for glycosylation of the intermediates. When incubating the microbial strain with a plant extract or fraction thereof comprising the glycoside intermediates, these intermediates are available for further glycosylation by the microbial cells. In various embodiments, the advanced glycosylation products are recovered from the media and/or microbial cells.

The glycoside intermediates can be any glycosylated secondary metabolite, such as those naturally found in plant extracts, including glycosylated terpenoids, flavonoids, cannabinoids, polyketides, stilbenoids, and polyphenols, among others. In some embodiments, the glycosylated intermediate is a glycosylated terpenoid, such as steviol glycoside or mogroside, and may find use as a sweetener. In some embodiments, biosynthesis of the product involves at least two glycosylation reactions of the glycoside intermediate in the microbial cell.

In some embodiments, the glycoside intermediates are from stevia leaf extract. For example, RebM and other advanced glycosylation products may be biosynthesized from steviol glycoside intermediates such as stevioside, steviolbioside, rebaudioside A (RebA), and rebaudioside C (RebC), among others. The microbial cell expresses one or more UDP-dependent glycosyl transferase enzymes in the cytoplasm, for glycosylation of the lower value intermediates. When incubating the microbial strain with a stevia leaf extract or fraction thereof comprising the steviol glycoside intermediates, these intermediates are available to the cells for further glycosylation, and these products can be recovered from the media and/or microbial cells. Accordingly, this process uses advanced intermediates in the stevia leaf extract, namely steviol glycosides having from one to five glycosylations (as well as in some embodiments the aglycone core, steviol). Advanced intermediates from stevia leaf extract are readily available from existing industrial extraction of steviol glycosides.

In various embodiments, the microbial cell expresses at least one, or at least two, or at least three, or at least four UGT enzymes that glycosylate a glycoside intermediate, and may be selected from those listed in Table 1 and those provided herein as SEQ ID NOS: 1-45, as well as derivatives thereof. In various embodiments, the UGT enzymes are independently selected from 1-2' glycosylating UGT enzymes, 1-3' glycosylating UGT enzymes, and O-glycosylating UGT enzymes. In various embodiments, these enzymes are expressed intracellularly, in that they do not contain membrane translocation or secretion signals.

In some embodiments, particularly with respect to glycosylation of steviol glycoside intermediates in stevia leaf extract, the microbial cell expresses four UGT enzymes, such as a 13-O UGT glycosylating enzyme, a 19-O UGT glycosylating enzyme, a 1-2' UGT glycosylating enzyme, and a 1-3' UGT glycosylating enzyme.

In various embodiments, the microbial cell expresses a 1-3' glycosylating UGT enzyme. For example, the 1-3' glycosylating UGT enzyme may be selected from SrUGT76G1, MbUGT1-3, and derivatives thereof (e.g., UGT76G1 L200A or MbUGT1-3_1, MbUGT1-3_1.5, or MbUGT1-3_2).

In these and other embodiments, the microbial cell expresses a 1-2' glycosylating UGT enzyme. For example, the 1-2' glycosylating UGT enzyme may be selected from SrUGT91D2, SrUGT91D1, SrUGT91D2e, OsUGT1-2, MbUGT1,2, MbUGT1,2.2, and derivatives thereof.

In these or other embodiments, the microbial cell expresses a C13 O-glycosylating UGT enzyme. For example, the C13 O-glycosylating UGT enzyme may be selected from SrUGT85C2 and derivatives thereof (e.g., MbUGTC13).

In these or other embodiments, the microbial cell expresses a C19 O-glycosylating UGT enzyme. For example, the C19 O-glycosylating enzyme may be selected from SrUGT74G1, MbUGTc19, and derivatives thereof (e.g., MbUGTc19-2).

Whole cell conversion requires that enzymes which are expressed intracellularly act on externally fed substrate (e.g., glycosylated intermediates) and that the cell provides UDP-glucose cofactor regeneration. This is in contrast to processes that rely on enzymes that are purified or secreted outside the cell, which requires an exogenous UDP-glucose supply or UDP-glucose precursor or UDP-glucose regeneration mechanism or UDP-glucose regeneration enzyme system. In embodiments of the present invention, catalysis (glycosylation) is carried out with live microbial cells. UDP-glucose cofactor recycling takes place using the native cellular metabolism without requiring additional externally provided enzymes or substrate feeding.

In accordance with the present disclosure, genetic modifications to the microbial cell allow for glycoside intermediates to be available for further glycosylation by intracellularly expressed enzymes. In some embodiments, advanced glycosylated products can be recovered from the medium, as opposed to extracted from lysed cells. In some embodiments, the microbial cell has one or more genetic modifications that increase UDP-glucose availability. In some embodiments, without wishing to be bound by theory, these modifications may also stress the cell for glucose availability, leading to the increased expression of endogenous transporters to import the glycoside intermediates into the cell. In some embodiments, without wishing to be bound by theory, the cells are rendered permeable through genetic modification or media components, allowing passive diffusion of products and substrates.

In various embodiments, the microbial cell has an overexpression of one or more endogenous transporters (e.g., as compared to a parent microbial strain), or in certain embodiments, is modified to express a recombinant and/or engineered transport protein. In some embodiments, the microbial cell expresses one or more additional copies of an endogenous transport protein, or derivative thereof. For example, expression or activity of transport proteins can be modified to increase transport into the cell of steviol glycoside substrates (e.g., one or more of stevioside, steviolbioside, RebA, and/or RebC), while exporting product, such as RebM and/or RebD as well as other advanced glycosylation products. Exemplary transport proteins that can be overexpressed or engineered for altered activity or substrate specificity in the microbial cell include *E. coli* acrAD, xylE, ascF, bglF, chbA, ptsG/crr, wzxE, rfbX, as well as orthologs or derivatives thereof. Other transport proteins include those selected from bacterial or endogenous transport proteins that transport the desired glycoside intermediate. For example, the transporter may be from the host species, or another bacterial or yeast species, and may be engineered to adjust its affinity for the particular glycoside intermediates or products.

In various embodiments, the method results in at least 40% conversion, or at least 50% conversion, or at least 75% conversion of the glycoside intermediates to desired product (e.g., conversion of stevioside, steviolbioside, and RebA to RebD, RebM, and/or other highly glycosylated rebaudiosides). In the production of RebM, the product profile can strongly favor RebM over RebD.

The method may be performed by batch fermentation, fed-batch fermentation, continuous fermentation, or semi-continuous fermentation. For example, in some embodiments, the method is conducted by batch fermentation with incubation times of less than about 72 hours, or in some embodiments, less than about 48 hours, or less than about 24 hours.

In some aspects, the invention provides methods for making a product comprising an advanced steviol glycoside, such as RebM. The method comprises incorporating the target steviol glycoside into a product, such as a food, beverage, oral care product, sweetener, flavoring agent, or other product. In some aspects, the invention provides methods for making a sweetener composition comprising a plurality of high-intensity sweeteners, such as two or more of a steviol glycoside, a mogroside, sucralose, aspartame, neotame, advantame, acesulfame potassium, saccharin, cyclamate, neohesperidin dihydrochalcone, gnetifolin E, and/or piceatannol 4'-O-β-D-glucopyranoside.

Other aspects and embodiments of the invention will be apparent from the following detailed description.

DETAILED DESCRIPTION OF THE INVENTION

Figure 1:
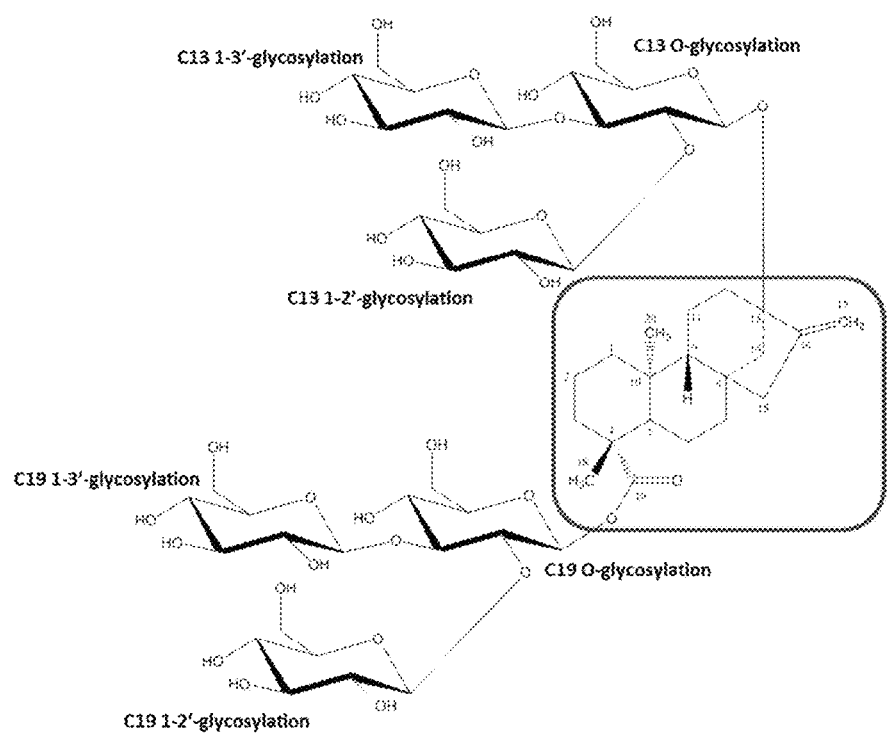
FIG. 1. Structure of RebM. The steviol scaffold (a diterpenoid) is shown boxed. RebM contains six glycosylations: (1) a C13 O-glycosylation, (2) a C13 1-2' glycosylation, (3) a C13 1-3' glycosylation, (4) a C19 O-glycosylation, (5) a C19 1-2' glycosylation, and (6) a C19 1-3' glycosylation.

In various aspects and embodiments, the invention provides microbial cells and methods for producing advanced glycosylation products from lower glycosylated intermediates. In various embodiments, the microbial cell expresses one or more UDP-dependent glycosyl transferase enzymes (e.g., intracellularly), for glycosylation of the intermediates. In various embodiments, the microbial cell has one or more genetic modifications that increase the availability of UDP-glucose. When incubating the microbial strain with the glycoside intermediates (e.g., from a plant extract or fraction thereof), these glycoside intermediates are available to the cell for further glycosylation by intracellularly-expressed glycosyltransferase enzymes. In some embodiments, the advanced glycosylation products can be recovered from the media, or in some embodiments, are recovered from the media and microbial cells.

The glycoside intermediates can be any glycosylated secondary metabolite, such as those naturally found in plant extracts, including glycosylated terpenoids, glycosylated flavonoids, glycosylated cannabinoids, glycosylated polyketides, glycosylated stilbenoids, and glycosylated polyphenols, among others. In some embodiments, the glycoside intermediate is a glycosylated terpenoid, such as steviol glycoside or mogroside. In some embodiments, the glycoside intermediate has one, two, three, four, or five glycosyl groups, including glycosyl groups selected from glucosyl, galactosyl, mannosyl, xylosyl, and rhamnosyl groups, among others. In various embodiments, the glycosylated product has at least four glycosyl groups, or at least five glycosyl groups, or at least six glycosyl groups. In other embodiments, the product has seven, eight, nine, or more glycosyl groups. In some embodiments, biosynthesis of the product involves at least two glycosylations of the intermediate by the microbial cell.

In some embodiments, the glycoside intermediates are from stevia leaf extract. For example, steviol glycosides having five, six, or more glycosylations (such as RebD or RebM) may be biosynthesized from steviol glycoside intermediates such as stevioside, steviolbioside, rebaudioside A, dulcoside A, dulcoside B, rebaudioside C, and rebaudioside F, among others. The microbial cell expresses one or more UDP-dependent glycosyl transferase enzymes for glycosylation of these lower value precursors. When incubating the microbial strain with a stevia leaf extract or fraction thereof comprising the steviol glycoside intermediates, these intermediates are available for further glycosylation to RebD or RebM or other advanced glycosylation product (e.g., RebI), which can be recovered from the media and/or microbial cells.

In various embodiments, the UDP-dependent glycosyl transferase enzymes are expressed "intracellularly", in that the enzymes do not possess membrane translocation or secretion peptides or domains. Thus, expression of the UGT enzymes takes place in the cytoplasm, and these enzymes are not directed outside the cell via a secretion or transport signal. In various embodiments, the UGT enzymes do not contain membrane anchoring domains. That is, in various embodiments the UGT enzymes do not comprise a transmembrane domain.

In some embodiments, the process uses advanced intermediates in the stevia leaf extract, namely steviol (the aglycone intermediate) and steviol glycosides having from one to five glycosylations, which are available to the microbial cell for further glycosylation. Advanced intermediates from stevia leaf extract are readily available from existing industrial extraction of steviol glycosides. As shown in Table 2, leaf extract may contain primarily the pathway intermediates stevioside and rebaudioside A (RebA). In various embodiments, the stevia leaf extract is an extraction of steviol glycosides. In some embodiments, the extract comprises one or more of stevioside, steviolbioside, and rebaudioside A, as prominent components. In some embodiments, the extract comprises one or more of dulcoside A, dulcoside B, RebC and/or RebF as prominent components. A prominent component generally makes up at least about 10% of the steviol glycosides in the extract or fraction thereof, but in some embodiments, may make up at least about 20%, or at least about 25%, or at least about 30% of the steviol glycosides in the extract or fraction thereof.

RebM is illustrated in FIG. 1. RebM contains six glycosylations of a steviol core: (1) a C13 O-glycosylation, (2) a C13 1-2' glycosylation, (3) a C13 1-3' glycosylation, (4) a C19 O-glycosylation, (5) a C19 1-2' glycosylation, and (6) a C19 1-3' glycosylation. While various glycosylation products are possible (FIG. 2), RebM can be synthesized from steviol through the action of four UGT enzymes, and UGT glycosylation enzymes are each capable of acting on a number of substrates. For example, both UGT91D2 and OsUGT1-2 are 1-2' glycosylating enzymes that can produce steviolbioside from steviolmonoside (by action at C13), as well as RebD from RebA (by action at C19). Further, UGT76G1 is a 1-3' glycosylating enzyme that can produce RebA from stevioside (by action at C13), as well as RebM from RebD (by action at C19).

UGT enzymes for glycosylation of steviol and steviol glycosides (including for biosynthesis of RebM) are disclosed in US 2017/0332673, which is hereby incorporated by reference in its entirety. Exemplary UGT enzymes are listed in Table 1, below (referenced patent applications are hereby incorporated by reference in their entirety):

TABLE 1

Example UGT Enzymes

| Type of glycosylation | Enzyme | Gene ID | Protein ID | Description |
|---|---|---|---|---|
| C13 | SrUGT85C2 | AY345978.1 | AAR06916.1 | |
| | MbUGTC13 | | | US 2017/0332673 |
| C19 | SrUGT74G1 | AY345982.1 | AAR06920.1 | |
| | MbUGTc19 | — | — | US 2017/0332673 |
| | MbUGTc19-2 | | | US 2017/0332673 |
| 1-2' | SrUGT91D1 | AY345980.1 | AAR06918.1 | |
| | SrUGT91D2 | ACE87855.1 | ACE87855.1 | |
| | SrUGT91D2e | — | — | US 2011/038967 |
| | OsUGT1-2 | NM_001057542.1 | NP_001051007.2 | WO 2013/022989 |
| | MbUGT1,2 | — | — | US 2017/0332673 |
| | MbUGT1,2.2 | — | — | US 2017/0332673 |
| 1-3' | SrUGT76G1 | FB917645.1 | CAX02464.1 | |
| | MbUGT1-3 | | | US 2017/0332673 |
| | 76G1_L200A | | | US 2017/0332673 |
| | MbUGT1-3_1 | | | U.S. Ser. No. 62/866,148 |
| | MbUGT1-3_1.5 | | | This disclosure |
| | MbUGT1-3_2 | | | U.S. Ser. No. 62/866,148 |

Amino acid sequences for exemplary UGT enzymes are provided by this disclosure as SEQ ID NOS: 1-17. SEQ ID NO:1 is *Stevia rebaudiana* UGT85C2. SEQ ID NO:13 is SrUGT85C2 with a P215T substitution, and insertion of an Ala at the 2nd position to increase stability. SEQ ID NO:2 is *Stevia rebaudiana* UGT74G1 (with insertion of Ala at the 2nd position). SEQ ID NOS:8 and 12 are circular permutants based on SrUGT74G1 (MbUGTC19 and MbUGTC19-2). SEQ ID NO:3 is *Stevia rebaudiana* UGT76G1. Circular permutants with 1-3' glycosylating activity are disclosed as SEQ ID NO:10 (MbUGT1-3) and SEQ ID NOS:15, 16, and 17 (MbUGT1-3_1, MbUGT1-3_1.5, and MbUGT1-3_2, respectively). UGT76G1 with a L200A substitution, and Ala at position 2, is disclosed as SEQ ID NO:14. *Stevia rebaudiana* UGT91D1, UGT91D2, and UGT91D2e are disclosed as SEQ ID NOS:4, 5, and 6. *Oryza sativa* UGT1-2 is disclosed as SEQ ID NO:7. MbUGT1,2 and MbUGT1,2.2 are circular permutant enzymes with 1-2' glycosylating activity (SEQ ID NOS: 9 and 11).

Additional UGT enzymes are provided as SEQ ID NOS: 18 to 46, from species *Siraitia grosvenorii* (monk fruit), *Momordica charantia* (bitter melon), *Cucumis sativa* (Cucumber), *Cucurbita maxima* (squash), *Cucurbita moschata* (squash, pumpkin), *Prunus persica* (peach), *Theobroma cacao* (cacao), *Corchorus capsularis* (white jute), *Ziziphus jujube* (red date), *Vitis vinifera* (grape vine), *Juglans regia* (walnut), *Hevea brasihensis* (rubber tree), *Manihot esculenta* (cassava), *Cephalotus follicularis* (pitcher plant), and *Coffea Arabica* (coffee). UGT enzymes can be selected and optionally engineered based on the desired product and available intermediate.

Figure 2:
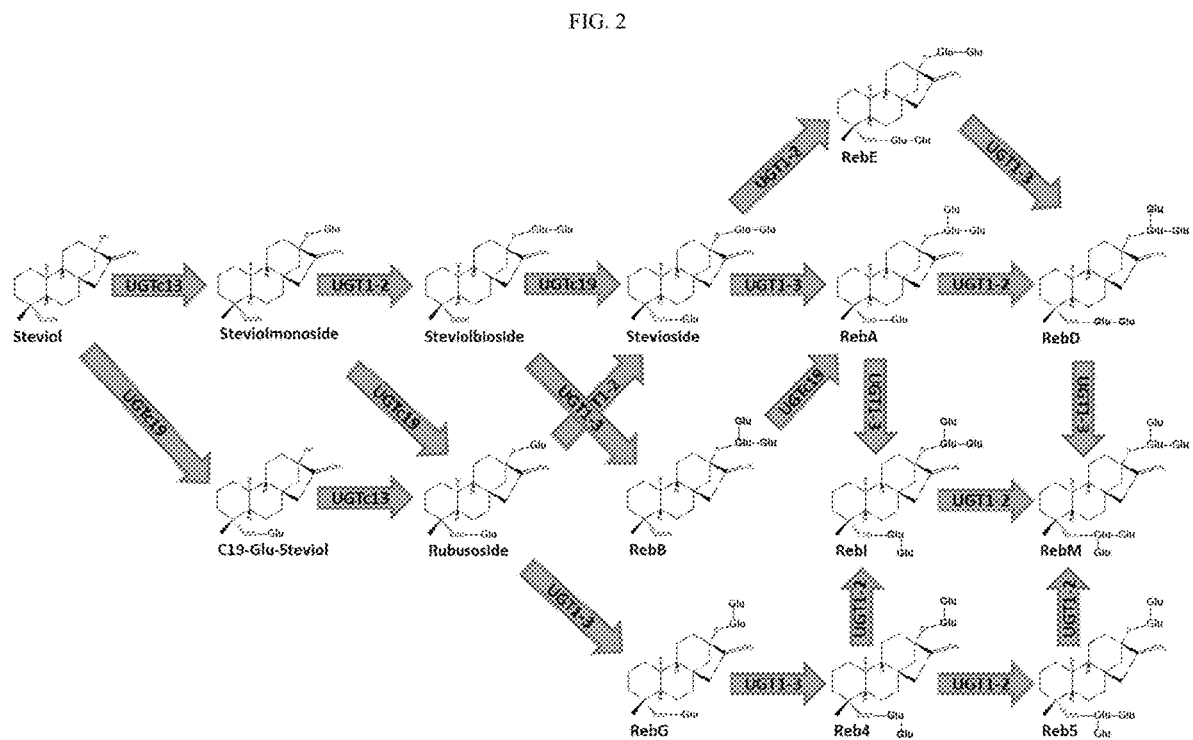
FIG. 2. Glycosylation products produced by action of UGT enzymes on steviol and steviol glycoside intermediates.
Figure 3:
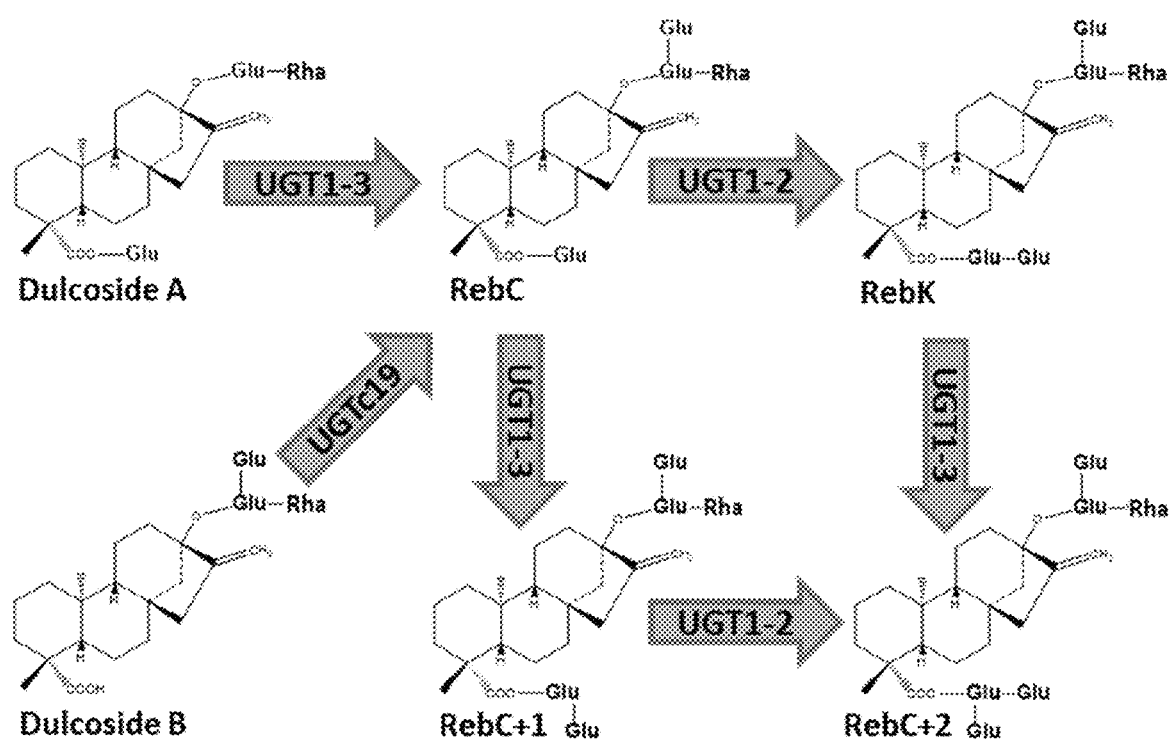
FIG. 3. Glycosylated products produced by action of UGT enzymes on steviol glycoside intermediates containing rhamnose.

In various embodiments, the microbial cell expresses at least one, or at least two, or at least three, or at least four UGT enzymes. In some embodiments, the UGT enzymes glycosylate a steviol glycoside substrate, including those listed in Table 2. In some embodiments, the microbial cell expresses four UGT enzymes that glycosylate a steviol glycoside intermediate, such as a 13-O UGT glycosylating enzyme, a 19-O UGT glycosylating enzyme, a 1-2' UGT glycosylating enzyme, and a 1-3' UGT glycosylating enzyme. The action of these general classes of UGT enzymes on glycosylated intermediates of the stevia leaf are depicted in FIGS. 2 and 3.

In various embodiments, the microbial cell expresses a 1-3' glycosylating UGT enzyme. For example, the 1-3' glycosylating UGT enzyme may be selected from SrUGT76G1, MbUGT1-3_1, MbUGT1-3_1.5, and MbUGT1-3_2, and derivatives thereof.

In these and other embodiments, the microbial cell expresses a 1-2' glycosylating UGT enzyme. For example, the 1-2' glycosylating UGT enzyme may be selected from SrUGT91D2, SrUGT91D1, SrUGT91D2e, OsUGT1-2, MbUGT1,2, MbUGT1,2.2, and derivatives thereof.

In these or other embodiments, the microbial cell expresses a C13 O-glycosylating UGT enzyme. For example, the C13 O-glycosylating UGT enzyme may be selected from SrUGT85C2 and derivatives thereof (e.g., MbUGTC13).

In these or other embodiments, the microbial cell expresses a C19 O-glycosylating UGT enzyme. For example, the C19 O-glycosylating enzyme may be selected from SrUGT74G1, MbUGTc19, and derivatives thereof (e.g., MbUGTc19-2).

In these or other embodiments, the microbial cell expresses a 1-3' glycosylating UGT enzyme and a 1-2' glycosylating UGT enzyme. In some embodiments, the microbial cell expresses a 1-3' glycosylating UGT enzyme, a 1-2' glycosylating UGT enzyme, and a C13 O-glycosylating UGT enzyme. In some embodiments, the microbial cell expresses a 1-3' glycosylating UGT enzyme, a 1-2' glycosylating UGT enzyme, a C19 O-glycosylating UGT enzyme, and a C19 O-glycosylating UGT enzyme. In some embodiments, the microbial cell expresses a 1-3' glycosylating UGT enzyme, a 1-2' glycosylating UGT enzyme, a C19 O-glycosylating UGT enzyme, and a C13 O-glycosylating UGT enzyme. In some embodiments, the microbial cell expresses a SrUGT85C2 or derivative thereof (e.g., MbUGTC13), MbUGT1,2.2 or derivative thereof, SrUGT74G1 or derivative thereof (e.g., MbUGTc19 or MbUGTc19-2), and SrUGT76G1 or MbUGT1-3_1 or derivative thereof (e.g., 76G1 L200A, MbUGT1-3_1.5, or MbUGT1-3_2). Without being bound by theory, engineered UGT enzymes may provide for increased carbon flux to RebM (as well as higher glycosylation products), and particularly due to substrate binding pockets that are better able to accommodate larger substrates, without substantial loss of activity on lower glycosylated intermediates. In these embodiments, the UGT enzymes (such as the 1-3' and 1-2' glycosylating UGT enzymes) may have an increased rate of activity (e.g., rate of substrate binding and turnover) with more highly glycosylated steviol substrates such as RebA or RebD.

Derivatives of UGT enzymes generally comprise an amino acid sequence having at least about 50% identity, at least about 60% identity, at least about 70% identity, at least about 80% identity, at least about 85% identity, or at least about 90% identity, or at least about 95% identity, or at least 96%, 97%, 98% or 99% identity to one or more of SEQ ID NOS: 1 to 46. In some embodiments, the derivative has from 1 to 20 or from 1 to 10, or from 1 to 5 amino acid modifications (independently selected from amino acid substitutions, insertions, and deletions), with respect to one of SEQ ID NOS:1 to 46. In some embodiments, for example with regard to production of RebM and other advanced steviol glycosides (e.g., having at least 5 glycosyl groups) from steviol glycoside intermediates, derivatives of these UGT enzymes comprise an amino acid sequence having at least about 50% identity, at least about 60% identity, at least about 70% identity, at least about 80% identity, at least about 85% identity, or at least about 90% identity, or at least about 95% identity, or at least 96%, 97%, 98% or 99% identity to one or more of SEQ ID NOS: 1 to 17. In some embodiments, the derivative has from 1 to 20 or from 1 to 10, or from 1 to 5 amino acid modifications (independently selected from amino acid substitutions, insertions, and deletions), with respect to one of SEQ ID NOS: 1 to 17.

In some embodiments, the microbial cell expresses a 1-3' UGT enzyme comprising an amino acid sequence that is at least about 75% identical to the amino acid sequence of SEQ ID NO:15, SEQ ID NO:16, or SEQ ID NO:17. In some embodiments, the 1-3' UGT comprises an amino acid sequence that is at least about 80% identical to SEQ ID NO:15, 16, or 17. In some embodiments, the amino acid sequence of the 1-3' UGT enzyme is at least about 85% identical to SEQ ID NO:15, 16, or 17, or at least about 90% identical to SEQ ID NO:15, 16, or 17 or at least about 95% identical to SEQ ID NO:15, 16, or 17, or at least about 98% identical to SEQ ID NO: 15, 16, or 17. In some embodiments, the amino acid sequence of the 1-3' UGT enzyme comprises the amino acid of SEQ ID NO:15, 16, or 17.

For example, the amino acid sequence may have from 1 to 20 amino acid modifications independently selected from substitutions, deletions, and insertions, with respect to the amino acid sequence SEQ ID NO:15, 16, or 17. In some embodiments, the amino acid sequence has from 1 to 10 amino acid modifications (e.g., from 1 to 5) independently selected from substitutions, deletions, and insertions, with respect to the amino acid sequence of SEQ ID NO:15, 16, or 17. Amino acid modifications to the amino acid sequence of SEQ ID NO:15, 16, or 17 can be guided by available enzyme structures and construction of homology models. Exemplary structures are described in, e.g., Li, et al., *Crystal Structure of Medicago truncatula UGT85H2-insights into the Structural Basis of a Multifunctional (iso) Flavonoid Glycosyltransferase, J. of Mol. Biol.* 370.5 (2007): 951-963. Publicly available crystal structures (e.g., PDB entry: 2PQ6) may be used to inform amino acid modifications. For example, one or more amino acid modifications can be made to the active site or in the vicinity of the active site to improve the binding of substrate, and/or to improve reaction geometries of these substrates with catalytic side chains.

In some embodiments, the 1-3' UGT enzyme comprises an amino acid substitution at positions corresponding to positions 29, 200, 357, and 414 of SEQ ID NO:3 (*Stevia rebaudiana* UGT76G1). Substitutions at these positions, which are included in the enzyme of SEQ ID NOS:15 and 17 (positions 183, 354, 54, and 111, respectfully, in SEQ ID NO:15) can provide dramatic improvements in activity. In some embodiments, the identity of amino acids at positions corresponding to positions 183, 354, 54, and 111 of SEQ ID NO:15, allows for further modification at other positions. For example, in some embodiments, the 1-3' UGT enzyme comprises an amino acid sequence that is at least about 60% identical to the amino acid sequence of SEQ ID NO:15 or 17, wherein the UGT enzyme comprises: a glycine (G) or threonine (T) at the position corresponding to position 54 of SEQ ID NO:15; a leucine (L) or isoleucine (I) at the position corresponding to position 111 of SEQ ID NO:15; a methionine (M) or leucine (L) at the position corresponding to position 183 of SEQ ID NO:15; and an alanine (A), or glycine (G), or serine (S) at the position corresponding to position 354 of SEQ ID NO:15. In some embodiments, the 1-3' UGT enzyme comprises a methionine (M) at the position corresponding to position 183 of SEQ ID NO:15. In some embodiments, the 1-3' UGT enzyme comprises a glycine (G) at the position corresponding to position 54 of SEQ ID NO:15. In some embodiments, the 1-3' UGT enzyme comprises a leucine (L) at the position corresponding to position 111 of SEQ ID NO:15. In some embodiments, the 1-3' UGT has two or three of a methionine (M) at the position corresponding to position 183 of SEQ ID NO:15, a glycine (G) at the position corresponding to position 54 of SEQ ID NO:15, and a leucine (L) at the position corresponding to position 111 of SEQ ID NO:15. These modifications can provide substantial improvements to the activity of the enzyme.

In some embodiments, the 1-3' UGT enzyme comprises an insertion of from 5 to about 15 amino acids, such as from 6 to 12 amino acids, or about 6 or about 11 amino acids, after the position corresponding to position 155 of SEQ ID NO:15. In some embodiments, the insertion is a flexible and hydrophilic sequence that is predominately Glycine and Serine residues. In some embodiments, the sequence is GSGGSG (SEQ ID NO:47) or GSGGSGGSG (SEQ ID NO:48).

In various embodiments, the 1-3' UGT enzyme shows improved conversion of stevioside to Reb A, and improved conversion of RebD to RebM, as compared to UGT76G1-L200A (SEQ ID NO:14). This improved conversion is exhibited in a bioconversion assay where stevioside or RebD substrate is fed to microbial cells expressing the 1-3' UGT enzyme. Improved conversion can be demonstrated in reactions with cell lysates containing recombinantly expressed 1-3' UGT, or in vitro reactions with purified or partially purified 1-3' UGT.

Changes to the amino acid sequence of an enzyme can alter its activity or have no measurable effect. Silent changes with no measurable effect are often conservative substitutions and small insertions or deletions on solvent-exposed surfaces that are located away from active sites and substrate-binding sites. In contrast, enzymatic activity is more likely to be affected by non-conservative substitutions, large insertions or deletions, and changes within active sites, substrate-binding sites, and at buried positions important for protein folding or conformation. Changes that alter enzymatic activity may increase or decrease the reaction rate or increase or decrease the affinity or specificity for a particular substrate. For example, changes that increase the size of a substrate-binding site may permit an enzyme to act on larger substrates and changes that position a catalytic amino acid side chain closer to a target site on a substrate may increase the enzymatic rate.

Knowledge of the three-dimensional structure of an enzyme and the location of relevant active sites, substrate-binding sites, and other interaction sites can facilitate the rational design of derivatives and provide mechanistic insight into the phenotype of specific changes. Plant UGTs share a highly conserved secondary and tertiary structure while having relatively low amino acid sequence identity. Osmani et al, *Substrate specificity of plant UDP-dependent glycosyltransferases predicted from crystal structures and homology modeling, Phytochemistry* 70 (2009) 325-347. The sugar acceptor and sugar donor substrates of UGTs are accommodated in a cleft formed between the N- and C-terminal domains. Several regions of the primary sequence contribute to the formation of the substrate binding pocket including structurally conserved domains as well as loop regions differing both with respect to their amino acid sequence and sequence length.

Construction of UGT derivatives can be guided based on homology modeling compared to known structures. For example, based on crystal structure analysis of SrUGT76G1_L200A and an amino acid sequence alignment of SrUGT76G1 to MbUGT3-1_1, it is predicted that the steviol core of stevioside is close (within 4 Å) to the following residues of MbUGT3-1_1: 1244, L280, W351, A354, I357, M362, and T438. Further, the C19 1-2 glycosylation is predicted to be close (within 4 Å) to T438. The steviol core of RebD is predicted to be close (within 4A) of the following hydrophobic side chains of MbUGT3-1_1: L239, M242, I244, L280, I353, A354, and I357. The C13 1-2' glycosylation is predicted to be close (within 4 Å) of the following hydrogen bonding side chains of MbUGT3-1_1: S301 and D77. Positioning and amino acid content of the V341-Q352 and K355-A367 helices of MbUGT3-1_1 may be important for catalysis as the mutation corresponding to L200A is in a loop between these helices. Positions L76 and/or D77 of MbUGT3-1_1 may interact with the C13 glycosylation of stevioside.

The amino acid sequence of one or more of the UGT enzymes can optionally include an alanine inserted or substituted at position 2 to decrease turnover in the cell. In various embodiments, one or more UGT enzymes comprise an alanine amino acid residue inserted or substituted at position 2 to provide additional stability in vivo.

Identity of amino acid sequences, i.e. the percentage of sequence identity, can be determined via sequence alignments. Such alignments can be carried out with several known algorithms, such as that described by Karlin and Altschul (Karlin & Altschul (1993) *Proc. Natl. Acad. Sci. USA* 90: 5873-5877), with hmmalign (HMMER package) or with the CLUSTAL algorithm (Thompson, J. D., Higgins, D. G. & Gibson, T. J. (1994) *Nucleic Acids Res.* 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) *J. Mol. Biol.* 215: 403-410. BLAST protein alignments may be performed with the BLASTP program, score=50, word length=3. To obtain gapped alignments for comparative purposes, Gapped BLAST is utilized as described in Altschul et al (1997) *Nucleic Acids Res.* 25: 3389-3402. When utilizing BLAST and Gapped BLAST programs, the default parameters of the respective programs are used.

The UGT enzymes may be integrated into the chromosome of the microbial cell, or alternatively, are expressed extrachromosomally. For example, the UGT enzymes may be expressed from a bacterial artificial chromosome (BAC) or yeast artificial chromosome (YAC).

Expression of the UGT enzymes can be tuned for optimal activity, using, for example, gene modules (e.g., operons) or independent expression of the UGT enzymes. For example, expression of the genes or operons can be regulated through selection of promoters, such as inducible or constitutive promoters, with different strengths (e.g., strong, intermediate, or weak). Several non-limiting examples of promoters of different strengths include Trc, T5 and T7. Additionally, expression of genes or operons can be regulated through manipulation of the copy number of the gene or operon in the cell. In some embodiments, the cell expresses a single copy of each UGT enzyme. In some embodiments, expression of genes or operons can be regulated through manipulating the order of the genes within a module, where the genes transcribed first are generally expressed at a higher level.

In some embodiments, expression of genes or operons is regulated through integration of one or more genes or operons into the chromosome.

Optimization of UGT expression can also be achieved through selection of appropriate promoters and ribosomal binding sites. In some embodiments, this may include the selection of high-copy number plasmids, or single-, low- or medium-copy number plasmids. The step of transcription termination can also be targeted for regulation of gene expression, through the introduction or elimination of structures such as stem-loops.

Whole cell conversion requires that substrate (e.g., glycoside intermediates) is available to the cell for glycosylation by the expressed enzymes (e.g., the intracellularly expressed enzymes) and preferably product can be extracted from the extracellular media. Whole cell systems have advantages, since the cell provides UDP-glucose cofactor regeneration. This is in contrast to processes that use enzymes from cell lysis or secretion outside the cell, which requires an exogenous UDP-glucose supply or UDP-glucose precursor or UDP-glucose regeneration mechanism or UDP-glucose regeneration enzyme system. In embodiments of the present invention, catalysis (glycosylation) is carried out with live microbial cells, and UDP-glucose cofactor recycling takes place using the cellular metabolism without requiring enzyme feeding or substrate feeding for UDP-glucose regeneration.

US 2017/0332673 describes *E. coli* strains that overexpress MEP pathway enzymes, along with a downstream steviol biosynthesis pathway, and UGT enzymes to drive production of RebM from glucose. However, these strains do not perform biocatalysis of fed steviol glycoside intermediates to RebM, which may be, in part, due to the inability of the host cell to gain access to the steviol glycoside substrate. In accordance with the present disclosure, genetic modifications to the microbial cell allow for glycosylated intermediates to be available for further glycosylation in a whole cell system. Further, product can be recovered from the extracellular media, which facilitates downstream purification and processing of the product.

In some embodiments, the microbial cell has one or more genetic modifications that increase UDP-glucose availability. In some embodiments, without wishing to be bound by theory, these modifications may also stress the cell for glucose availability, leading to the increased expression of endogenous transporters to import steviol glycosides into the cell. Wild-type UDP-glucose levels in exponentially growing *E. coli* is about 2.5 mM (Bennett B D, Kimball E H, Gao M, Osterhout R, Van dien S J, Rabinowitz J D. *Absolute metabolite concentrations and implied enzyme active site occupancy in Escherichia coli. Nat Chem Biol.* 2009; 5(8): 593-9.). In some embodiments, genetic modifications to the host cell are engineered to increase UDP-glucose, e.g., to at least 5 mM, or at least 10 mM, in exponentially growing cells (e.g., that do not have recombinant expression of UGT enzymes).

In some embodiments, the microbial cell has a deletion, inactivation, or reduced activity or expression of a gene encoding an enzyme that consumes UDP-glucose. For example, the microbial cell may have a deletion, inactivation, or reduced activity of ushA (UDP-sugar hydrolase) and/or one or more of galE, galT, galK, and galM (which are responsible for UDP-galactose biosynthesis from UDP-glucose), or ortholog thereof in the microbial species. In some embodiments, galETKM genes are inactivated, deleted, or substantially reduced in expression. Alternatively or in addition, the microbial cell has a deletion, inactivation, or reduced activity or expression of *E. coli* otsA (trehalose-6-phosphate synthase), or ortholog thereof in the microbial species. Alternatively or in addition, the microbial cell has a deletion, inactivation, or reduced activity or expression of *E. coli* ugd (UDP-glucose 6-dehydrogenase), or ortholog thereof in the microbial species. Reducing or eliminating activity of otsA and ugd can remove or reduce UDP-glucose sinks to trehalose or UDP-glucuronidate, respectively.

Other UDP-glucose sinks that can be reduced or eliminated include eliminating or reducing activity or expression of genes responsible for lipid glycosylation and LPS biosynthesis, and genes responsible for glycosylating undecaprenyl-diphosphate (UPP). Genes involved in glycosylating lipids or LPS biosynthesis include *E. coli* waaG (lipopolysaccharide glucosyltransferase 1), *E. coli* waaO (UDP-D-glucose:(glucosyl)LPS α-1,3-glucosyltransferase)), and *E. coli* waaJ (UDP-glucose:(glycosyl)LPS α-1,2-glucosyltransferase)). Genes responsible for glycosylating undecaprenyl-diphosphate (UPP) include *E. coli* yfdG (putative bactoprenol-linked glucose translocase), *E. coli* yfdH (bactoprenol glucosyl transferase), *E. coli* yfdI (serotype specific glucosyl transferase), and *E. coli* wcaJ (undecaprenyl-phosphate glucose phosphotransferase). Deletion, inactivation, or reduction in activity or expression of one or more of these gene products (or corresponding otholgs in the microbial cell) can increase UDP-glucose availability.

In these or other embodiments, the microbial cell has a deletion, inactivation, or reduced activity or expression of a gene encoding an enzyme that consumes a precursor to UDP-glucose. For example, in some embodiments, the microbial cell has a deletion, inactivation, or reduced activity or expression of pgi (glucose-6 phosphate isomerase), or ortholog thereof in the microbial species of the host cell.

In these or other embodiments, the cell has an overexpression or increased activity of one or more genes encoding an enzyme involved in converting glucose-6-phosphate to UDP-glucose. For example, pgm (phosphoglucomutase) and/or galU (UTP-glucose-1-phosphate uridylyltransferase) (or ortholog or derivative thereof) can be overexpressed, or modified to increase enzyme productivity. Alternatively or in addition, *E. coli* ycjU (β-phosphoglucomutase), which converts glucose-6-phosphate to glucose-1-phosphate, and *Bifidobacterium bifidum* ugpA, which converts glucose-1-phosphate to UDP, or ortholog or derivative of these enzymes, can be overexpressed, or modified to increase enzyme productivity.

Alternatively or in addition, the microbial cell has one or more genetic modifications that increase flux to the pentose phosphate pathway (PPP), such as an overexpression or increased activity of *E. coli* zwf (or homologue or engineered derivative thereof), which is an NADP+-dependent glucose-6-phosphate dehydrogenase.

Alternatively or in addition, the microbial cell has one or more genetic modifications that increase glucose transport. Such modifications include increased expression or activity of *E. coli* galP (galactose:H+symporter) and *E. coli* glk (glucokinase), or alternatively *Zymomonas mobilis* glf and *E. coli* glk, or homologues, orthologs, or engineered derivatives of these genes.

Alternatively or in addition, the microbial cell has one or more genetic modifications that increase UTP production and recycling. Such modifications include increased expression or activity of *E. coli* pyrH (UMP kinase), *E. coli* cmk (cytidylate kinase), *E. coli* adk (adenylate kinase), or *E. coli* ndk (nucleoside diphosphate kinase), or homologs, orthologs, or engineered derivatives of these enzymes.

Alternatively or in addition, the microbial cell has one or more genetic modifications that increase UDP production. Such modifications include overexpression or increased activity of one or more of *E. coli* upp (uracil phosphoribosyltransferase), *E. coli* dctA (C4 dicarboxylate/orotate:H+ symporter), *E. coli* pyrE (orotate phosphoribosyltransferase), and *E. coli* pyrF (orotidine-5'-phosphate decarboxylase), including homologs, orthologs, or engineered derivatives thereof. For example, in some embodiments, the microbial cell overexpresses or has increased activity of upp, pyrH and cmk, or homolog or engineered derivative thereof. Alternatively, the microbial cell overexpresses or has increased activity of dctA, pyre, pyrH and cmk, or homolog or engineered derivative thereof.

Alternatively or in addition, the microbial cell may have one or more genetic modifications to remove or reduce regulation of glucose uptake. For example, the microbial cell may have a deletion, inactivation, or reduced expression of sgrS, which is a small regulatory RNA in *E. coli*.

Alternatively or in addition, the microbial cell may have one or more genetic modifications that reduce dephosphorylation of glucose-1-phosphate. Exemplary modifications include deletion, inactivation, or reduced expression or activity of one or more of *E. coli* agp (glucose-1-phosphatase), *E. coli* yihX (α-D-glucose-1-phosphate phosphatase), *E. coli* ybiV (sugar phosphatase), *E. coli* yidA (sugar phosphatase), *E. coli* yigL (phosphosugar phosphatase), and *E. coli* phoA (alkaline phosphatase), or an ortholog thereof in the microbial cell.

Alternatively or in addition, the microbial cell may have one or more genetic modifications that reduce conversion of glucose-1-phosphate to TDP-glucose. Exemplary modifications include deletion, inactivation, or reduced expression or activity of one or more of *E. coli* rffH (dTDP-glucose pyrophosphorylase) and *E. coli* rfbA (dTDP glucose pyrophosphorylase), or an ortholog thereof in the microbial cell.

Alternatively or in addition, the microbial cell may have one or more genetic modifications that reduce conversion of glucose-1-phosphate to ADP-glucose. Exemplary modifications include deletion, inactivation, or reduced expression or activity of *E. coli* gigC (glucose-1-phosphate adenylyltransferase), or an ortholog thereof in the microbial cell.

In some embodiments, the microbial cell is a bacterial cell comprising the genetic modifications: ushA and galETKM are deleted, inactivated, or reduced in expression; pgi is deleted, inactivated, or reduced in expression; and pgm and galU are overexpressed or complemented.

In some embodiments, endogenous genes are edited, to either inactivate or reduce enzymatic activity by changing the amino acid sequence of the encoded protein, or to reduce expression through editing of expression control sequences. Editing can modify endogenous promoters, ribosomal binding sequences, or other expression control sequences, and/or in some embodiments modifies trans-acting and/or cis-acting factors in gene regulation. Genome editing can take place using CRISPR/Cas genome editing techniques, or similar techniques employing zinc finger nucleases and TALENs. In some embodiments, the endogenous genes are replaced by homologous recombination.

The microbial cell in various embodiments does not express a recombinant biosynthesis pathway for production of precursors (e.g., comprising one or more plant enzymes). For example, for microbial cells producing RebM (and other advanced glycosylation products) in accordance with embodiments of the invention, do not express a steviol biosynthesis pathway, such as copalyl synthase, kaurene synthase, kaurene oxidase and/or kaurenoic acid hydroxylase, such that production of RebM and other advanced glycosylation products is dependent on feeding steviol glycoside intermediates to the cell.

In various embodiments, the microbial cell is a bacteria selected from *Escherichia* spp., *Bacillus* spp., *Rhodobacter* spp., *Zymomonas* spp., or *Pseudomonas* spp. In some embodiments, the bacterial species is selected from *Escherichia coli*, *Bacillus subtilis*, *Rhodobacter capsulatus*, *Rhodobacter sphaeroides*, *Zymomonas mobilis*, or *Pseudomonas putida*. In some embodiments, the bacterial cell is *E. coli*.

In other embodiments, the cell is a fungal cell such as a yeast cell, such as, for example, *Saccharomyces* spp., *Schizosaccharomyces* spp., *Pichia* spp., *Phaffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. In an embodiment, the yeast may be a species of *Saccharomyces*, *Pichia*, or *Yarrowia*, including *Saccharomyces cerevisiae*, *Pichia pastoris*, and *Yarrowia lipolytica*. In some embodiments, the yeast cell expresses one or more bacterial transporters, or derivatives thereof, that import glycoside intermediates into the cell for further glycosylation.

In various embodiments, the microbial cell has an overexpression of one or more endogenous transporters (e.g., as compared to a parent microbial strain), or in certain embodiments, is modified to express a recombinant and/or engineered transport protein. In some embodiments, the microbial cell expresses one or more additional copies of an endogenous transport protein, or derivative thereof. For example, expression or activity of transport proteins can be modified to increase transport into the cell of steviol glycoside intermediates (e.g., one or more of stevioside, steviolbioside, and RebA, among others), while exporting product, such as RebM and/or RebD, and/or other advanced glycosylated steviol glycosides.

Exemplary transport proteins that can be overexpressed or engineered for altered activity or substrate specificity in the microbial cell include *E. coli* acrAD, xylE, ascF, bglF, chbA, ptsG/crr, wzxE, rfbX, as well as orthologs or derivatives thereof. Derivatives and orthologs of these proteins generally comprise an amino acid sequences having at least about 30%, or at least about 40%, or at least about 50% identity, at least about 60% identity, at least about 70% identity, at least about 80% identity, at least about 85% identity, or at least about 90% identity, or at least about 95% identity, or at least 96%, 97%, 98% or 99% identity to the *E. coli* transport protein.

acrAD is an *E. coli* multidrug efflux pump described in Aires J R and Nikaido H., *Aminoglycosides are captured from both periplasm and cytoplasm by the AcrD multidrug efflux transporter of Escherichia coli, J Bacteriol.* 2005; 187(6):1923-9. Further a homolog structure is described in Yu, E W, et al., *Structural basis of multiple drug-binding capacity of the AcrB multidrug efflux pump, Science* 2003; 300(5621):976-80.

xylE is an *E. coli* xylose transporter with homology to glucose transporters. xylE is described in Sumiya M, et al., *Molecular genetics of a receptor protein for D-xylose, encoded by the gene xylF, in Escherichia coli, Recept Channels* 1995; 3(2):117-28, with structure described by Sun L, et al., *Crystal structure of a bacterial homologue of glucose transporters GLUT-1-4*, Nature 2012; 490(7420): 361-6.

ascF is described by Hall B G and Xu L, *Nucleotide sequence, function, activation, and evolution of the cryptic asc operon of Escherichia coli K12, Mol. Biol. Evol.* 1992; 9(4):688-706. The asc operon is considered to play a role in cellobiose metabolism in *E. coli*.

bglF is described by Schnetz K, et al., *Identification of catalytic residues in the beta-glucoside permease of Escherichia coli by site-specific mutagenesis and demonstration of interdomain cross-reactivity between the beta-glucoside and glucose systems, J. Biol. Chem.* 1990; 265 (23):13464-71. A homologous structure is described in Herzberg O., *An atomic model for protein-protein phosphoryl group transfer, J. Biol. Chem.* 1992; 276(34):24819-23. bglF catalyzes transport and phosphorylation of beta-glucosides.

chba is described in Keyhani N O, et al., *The transport/phosphorylation of N,N'-diacetylchitobiose in Escherichia coli. Characterization of phosphor-IIB(Chb) and of a potential transition state analogue in the phosphotransfer reaction between the proteins IIA(Chb) and IIB(Chb). J. Biol. Chem.* 2000; 275(42):33102-9; with structure described in Tang C, et al., *Solution structure of enzyme IIA(Chitobiose) from the N,N'-diacetylchitobiose branch of the Escherichia coli phosphotransferase system. J. Biol. Chem.* 2005; 280 (12):11770-80. The phosphoenolpyruvate-dependent sugar phosphotransferase system (sugar PTS), is a major carbohydrate active transport system that catalyzes the phosphorylation of incoming sugar substrates concomitantly with their translocation across the cell membrane.

ptsG encodes the glucose-specific permease of the phosphotransferase transport system (PTS) and is described in Meins M, et al., *Glucose permease of Escherichia coli. Purification of the IIGlc subunit and functional characterization of its oligomeric forms. J. Biol. Chem.* 1988; 263 (26):12986-93. A structure is described in Cai M, et al., *Solution structure of the phosphoryl transfer complex between the signal-transducing protein IIAGlucose and the cytoplasmic domain of the glucose transporter IICBGlucose of the Escherichia coli glucose phosphotransferase system. J. Biol. Chem.* 2003; 278(27): 25191-206.

wzxE and its role in molecular transport is described by Rick P D, et al., *Evidence that the wzxE gene of Escherichia coli K-12 encodes a protein involved in the transbilayer movement of a trisaccharide-lipid intermediate in the assembly of enterobacterial common antigen. J. Biol. Chem.* 2003; 278(19):16534-42.

rfbx is a lipopolysaccharide transporter described in Hong Y, et al., *Progress in our understanding of wzx flippase for translocation of bacterial membrane lipid-linked oligosaccharide. J. Bacteriol.* 2018; 200(1).

Other transport proteins include those selected from bacterial or endogenous transport proteins that transport the desired glycoside intermediate into the cell, and/or transport the desired product out of the cell. For example, the transporter may be from the host species, or another bacterial or yeast species, and may be engineered to adjust its affinity for the particular glycoside intermediates or products. For example, the host cell may overexpress a transporter that is at least about 30%, or at least about 40%, or at least about 50% identical to an *E. coli* transporter selected from ampG, araE, araJ, bcr, cynX, emrA, emrB, emrD, emrE, emrK, emrY, entS, exuT, fsr, fucP, galP, garP, glpT, gudP, gudT, hcaT, hsrA, kgtP, lacY, lgoT, lplT, 1ptA, 1ptB, 1ptC, 1ptD, 1ptE, 1ptF, 1ptG, mdfA, mdtD, mdtG, mdtH, mdtM, mdtL, mhpT, msbA, nanT, narK, narU, nepI, nimT, nupG, proP, setA, setB, setC, shiA, tfaP, to1C, tsgA, uhpT, xapB, xylE, yaaU, yajR, ybjJ, ycaD, ydeA, ydeF, ydfJ, ydhC, ydhP, ydjE, ydjK, ydiM, ydiN, yebQ, ydcO, yegT, yfaV, yfcJ, ygaY, ygcE, ygcS, yhhS, yhjE, yhjX, yidT, yihN, yjhB, and ynfM. In some embodiments, the transporter is at least about 60%, at least about 70%, at least about 80%, at least about 90%, or at least about 95% identical to the *E. coli* transporter.

In some embodiments, the microbial cell expresses a transport protein that is at least 50% identical to a transporter from a eukaryotic cell, such as a yeast, fungus, or plant cell. In some embodiments, the transport protein is an ABC family transporter, and which is optionally of a subclass PDR (pleiotropic drug resistance) transporter, MDR (multidrug resistance) transporter, MFS family (Major Facilitator Superfamily) transporter, or SWEET (aka PQ-loop, Saliva, or MtN3 family) family transporter. In other embodiments, the transport protein is of a family selected from: AAAP, SulP, LCT, APC, MOP, ZIP, MPT, VIC, CPA2, ThrE, OPT, Trk, BASS, DMT, MC, AEC, Amt, Nramp, TRP-CC, ACR3, NCS1, PiT, ArsAB, IISP, GUP, MIT, Ctr, and CDF.

In some embodiments, the transporter is an ABC family transport protein (a/k/a ATP-binding cassette transporters), which generally include multiple subunits, one or two of which are transmembrane proteins and one or two of which are membrane-associated ATPases. The ATPase subunits utilize the energy of adenosine triphosphate (ATP) binding and hydrolysis to energize the translocation of various substrates across membranes, either for uptake or for export of the substrate. The ABC family transporter may be of any subclass, including, but not limited to: ABCA, ABCB, ABCC, ABCD, ABCE, ABCF, and ABCG.

In some embodiments, the transport protein is an MFS family transport protein (a/k/a Major Facilitator Superfamily), which are single-polypeptide secondary carriers capable of transporting small solutes in response to chemiosmotic ion gradients. Compounds transported by MFS transport proteins can include simple sugars, oligosaccharides, inositols, drugs, amino acids, nucleosides, organophosphate esters, Krebs cycle metabolites, and a large variety of organic and inorganic anions and cations. By way of example, MFS transport proteins include XylE (from *E. coli*), QacA (from *S. aureus*), Bmr (of *B. subtilis*), UhpT (from *E. coli*), LacY (from *E. coli*), FucP (from *E. coli*), and ExtU (from *E. coli*).

In some embodiments, the transporter is of SWEET (Sugars Will Eventually be Exported Transporters) family of transport proteins (a/k/a the PQ-loop, Saliva or MtN3 family), which is a family of sugar transporters and a member of the TOG superfamily. Eukaryotic family members of SWEET have 7 transmembrane segments (TMSs) in a 3+1+3 repeat arrangement. By way of example, SWEET transporter proteins include SWEET1, SWEET2, SWEET9, SWEET12, SWEET13, and SWEET14.

In some embodiments, the transport protein is at least 50% identical to a transport protein from *S. cerevisiae*. In some embodiments, the transporter is at least about 60%, at least about 70%, at least about 80%, at least about 90%, or at least about 95% identical to the *S. cerevisiae* transporter. Exemplary *S. cerevisiae* transport proteins include AC1, ADP1, ANT1, AQR1, AQY3, ARN1, ARN2, ARR3, ATG22, ATP4, ATP7, ATP19, ATR1, ATX2, AUS1, AVT3, AVT5, AVT6, AVT7, AZR1, CAF16, CCH1, COT1, CRC1, CTR3, DAL4, DNF1, DNF2, DTR1, DUR3, ECM3, ECM27, ENB1, ERS1, FEN2, FLR1, FSF1, FUR4, GAP1, GET3, GEX2, GGC1, GUP1, HOL1, HCT10, HXT3, HXT5, HXT8, HXT9, HXT11, HXT15, KHA1, ITR1, LEU5, LYP1, MCH1, MCH5, MDL2, MME1, MNR2, MPH2, MPH3, MRS2, MRS3, MTM1, MUP3, NFT1, OAC1, ODC2, OPT1, ORT1, PCA1, PDR1, PDR3, PDR5, PDR8, PDR10, PDR11, PDR12, PDR15, PDR18, PDRI, PDRI 1, PETE, PHO89, PIC2, PMA2, PMC1, PMR1, PRM10, PUT4, QDR1, QDR2, QDR3, RCH1, SAL1, SAM3, SBH2, SEO1, SGE1, SIT1, SLY41, SMF1, SNF3, SNQ2, SPF1, SRP101, SSU1, STE6, STL1, SUL1, TAT2, THI7, THI73, TIM8, TIM13, TOK1, TOM7, TOM70, TPN1, TPO1, TPO2, TPO3, TPO4, TRK2, UGA4, VBA3, VBA5, VCX1, VMA1, VMA3, VMA4, VMA6, VMR1, VPS73, YEA6, YHK8, YIA6, YMC1, YMD8, YOR1, YPK9, YVC1, ZRT1; YBR241C, YBR287W, YDR061W, YDR338C, YFRO45W, YGL114W, YGR125W, YIL166C, YKL050C, YMR253C, YMR279C, YNL095C, YOL075C, YPR003C, and YPRO11C.

In some embodiments, the *S. cerevisiae* transport protein is selected from one or more of ADP1, AQR1, ARN1, ARN2, ATR1, AUS1, AZR1, DAL4, DTR1, ENB1, FLR1, GEX2, HOL1, HXT3, HXT8, HXT11, NFT1, PDR1, PDR3, PDR5, PDR8, PDR10, PDR11, PDR12, PDR15, PDR18, QDR1, QDR2, QDR3, SEO1, SGE1, SIT1, SNQ2, SSU1, STE6, THI7, THI73, TIM8, TPN1, TPO1, TPO2, TPO3, TPO4, YHK8, YMD8, YOR1, and YVC1. In some embodiments, *S. cerevisiae* transport protein is selected from one or more of FLR1, PDR1, PDR3, PDR5, PDR10, PDR15, SNQ2, TPO1, and YOR1.

In some embodiments, the transporter is at least 50%, at least 60% identical, at least 70% identical, at least 80% identical, or at least 90 or 95% identical to)CP 013706116.1 (from *Brassica napus*), NP_001288941.1 (from *Brassica rapa*), NEC1 (from *Petunia hybrida*), and SWEET13 (from *Triticum urartu*).

In various embodiments with regard to biosynthesis of RebM, the method results in at least 40% conversion, or at least 50% conversion, or at least 75% conversion of stevioside, steviolbioside, and RebA to RebM. In some embodiments, the ratio of RebM to RebD is at least 2:1, or at least 4:1, or at least 6:1, or at least 8:1, or at least 9:1, or at least 10:1, or at least 15:1, or at least 20:1.

The method may be performed by batch fermentation, fed-batch fermentation, continuous fermentation, or semi-continuous fermentation. For example, in some embodiments, the method is conducted by batch fermentation or fed-batch fermentation with incubation times of less than about 72 hours, or in some embodiments, less than about 48 hours, or less than about 24 hours.

While the native UGT enzymes are generally plant enzymes (which often have optimal temperatures in the range of 20-24° C.) or are derived from plant enzymes, the present disclosure in some embodiments enables production of the glycosylated product at high yield in microbial cells (e.g., bacterial cells such as *E. coli*), with enzyme productivity at temperatures about 24° C. or more, such as from about 24° C. to about 37° C., or from about 27° C. to about 37° C., or from about 30° C. to about 37° C.

In some embodiments, the growth or production phase media may contain one or more detergents in an amount sufficient to enhance cell permeability, without significant impact on growth or viability. Exemplary detergents include Tween 20, Triton X-100, and SDS, among others.

In some embodiments, the process is scalable for large scale production. For example, in some embodiments, the size of the culture is at least about 100 L, at least about 200 L, at least about 500 L, at least about 1,000 L, or at least about 10,000 L.

In various embodiments, methods further include recovering glycosylated product from the cell culture or from cell lysates. In some embodiments, the culture produces at least about 100 mg/L, or at least about 200 mg/L, or at least about 500 mg/L, or at least about 1 g/L, or at least about 2 g/L, or at least about 5 g/L, or at least about 10 g/L, or at least about 20 g/L, or at least about 30 g/L, or at least about 40 g/L, or at least about 50 g/L of the glycosylated product, which in some embodiments is extracted from the culture media.

In some embodiments, the glycosylated products (e.g., RebM) are purified from media components. Thus, in some embodiments, the methods comprise separating growth media from host cells, and isolating the desired glycosylation products (e.g, RebM) from the growth media. In some embodiments, product such as RebM is further extracted from the cellular material.

In some aspects, the invention provides methods for making a product comprising a glycosylated product, such as RebM. The method comprises incorporating the target steviol glycoside (produced according to this disclosure) into a product, such as a food, beverage, oral care product, sweetener, flavoring agent, or other product. Purified steviol glycosides, prepared in accordance with the present invention, may be used in a variety of products including, but not limited to, foods, beverages, texturants (e.g., starches, fibers, gums, fats and fat mimetics, and emulsifiers), pharmaceutical compositions, tobacco products, nutraceutical compositions, oral hygiene compositions, and cosmetic compositions. Non-limiting examples of flavors for which RebM can be used in combination include lime, lemon, orange, fruit, banana, grape, pear, pineapple, mango, bitter almond, cola, cinnamon, sugar, cotton candy and vanilla flavors. Non-limiting examples of other food ingredients include flavors, acidulants, and amino acids, coloring agents, bulking agents, modified starches, gums, texturizers, preservatives, antioxidants, emulsifiers, stabilizers, thickeners and gelling agents.

In some aspects, the invention provides methods for making a sweetener product comprising a plurality of high-intensity sweeteners, said plurality including two or more of a steviol glycoside, a mogroside, sucralose, aspartame, neotame, advantame, acesulfame potassium, saccharin, cyclamate, neohesperidin dihydrochalcone, gnetifolin E, and/or piceatannol 4'-O-β-D-glucopyranoside. The method may further comprise incorporating the sweetener product into a food, beverage, oral care product, sweetener, flavoring agent, or other product, including those described above.

Target steviol glycoside(s), such as RebM, and sweetener compositions comprising the same, can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

Further, target steviol glycoside(s), such as RebM, and sweetener compositions obtained according to this invention, may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, RebM and sweetener compositions can be used as a sweetener not only for drinks, foodstuffs, and other products dedicated for human consumption, but also in animal feed and fodder with improved characteristics.

Examples of products in which target steviol glycoside(s) and sweetener compositions may be used include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Embodiments of the invention are demonstrated in the following, non-limiting examples.

Examples

Table 2 shows the steviol glycoside content of three batches of stevia leaf extract. Two intermediates, RebA and stevioside, on the pathway to RebM, are the two primary glycosides in the batches.

TABLE 2

Steviol Glycoside Composition of Available Stevia Leaf Extract

| % | Batch 1 | Batch 2 | Batch 3 |
| --- | --- | --- | --- |
| Rebaudioside A | 38.2 | 10.5 | 30.3 |
| Stevioside | 8.5 | 9.0 | 18.4 |
| Rebaudioside C | 12.9 | 4.2 | 16.6 |
| Rebaudioside B | 4.3 | 7.1 | 1.2 |
| Rubusoside | 5.0 | 2.2 | 2.0 |
| Rebaudioside F | 2.0 | 2.7 | 2.1 |
| Steviolbioside | 0.3 | 3.7 | 0.3 |
| Rebaudioside D | 0.2 | 2.1 | 0.9 |
| Dulcoside A | 0.9 | 0.4 | 0.5 |

Figure 4:
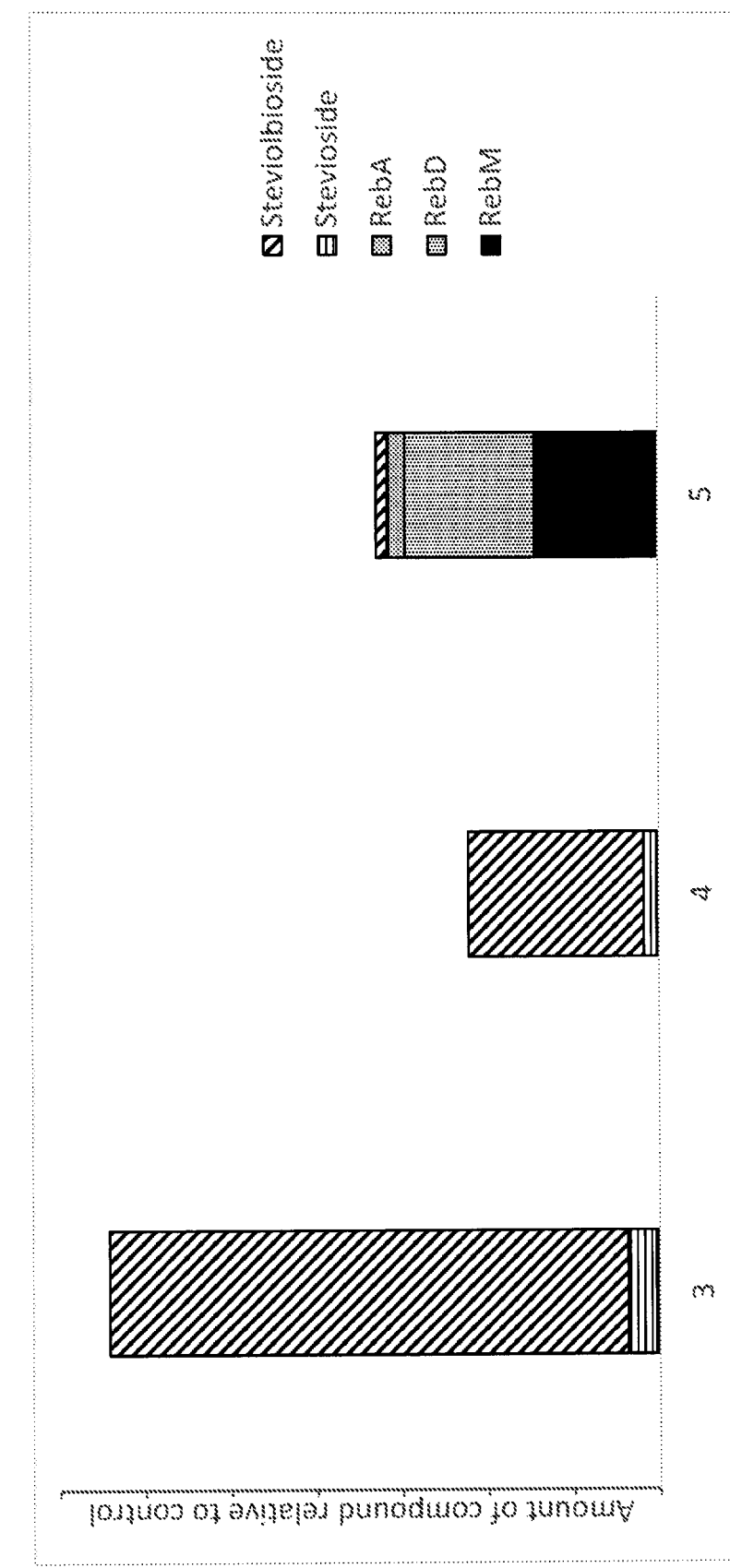
FIG. 4. Conversion of steviolbioside to RebM. For five major compounds in the RebM pathway, compound concentrations are shown relative to the total concentration of these compounds in a control strain that lacks the UGT enzymes. Strains were fed 0.2 mM steviolbioside and incubated with substrate for 48 hours before extraction. Strains 3 and 4 show no conversion of steviolbioside, while Strain 5 shows substantial conversion to RebD and RebM.

FIG. 4 shows bioconversion of glycosylated steviol glycoside intermediates. In the experiment, 0.2 mM steviolbioside was fed to engineered *E. coli* strains in 96 well plates. Product formation was examined after 48 hours. Whole cell bioconversion of even an early intermediate such as steviolbioside is possible, but for native *E. coli* the glycosylated substrate is not available to the UGT enzymes (Strain 5 shows substantial activity, while Strains 3 and 4 show negligible activity). Details of Strains are described in FIG. 8. The values reported in FIG. 4 are the compound concentration relative to control (the concentration of each compound is divided by the total concentration of these compounds for the empty vector control). The modifications contained in Strain 5 demonstrate bioconversion of steviolbioside to RebM.

Each of Strains 1-5 contained a BAC (bacterial artificial chromosome), that is a single copy plasmid, which expresses four UGT enzymes separately: MbUGTC13, MbUGT1.2_2, MbUGTc19_2, and 76G1_L200A. The control contained the same BAC backbone but without the UGT enzymes.

Figure 8:
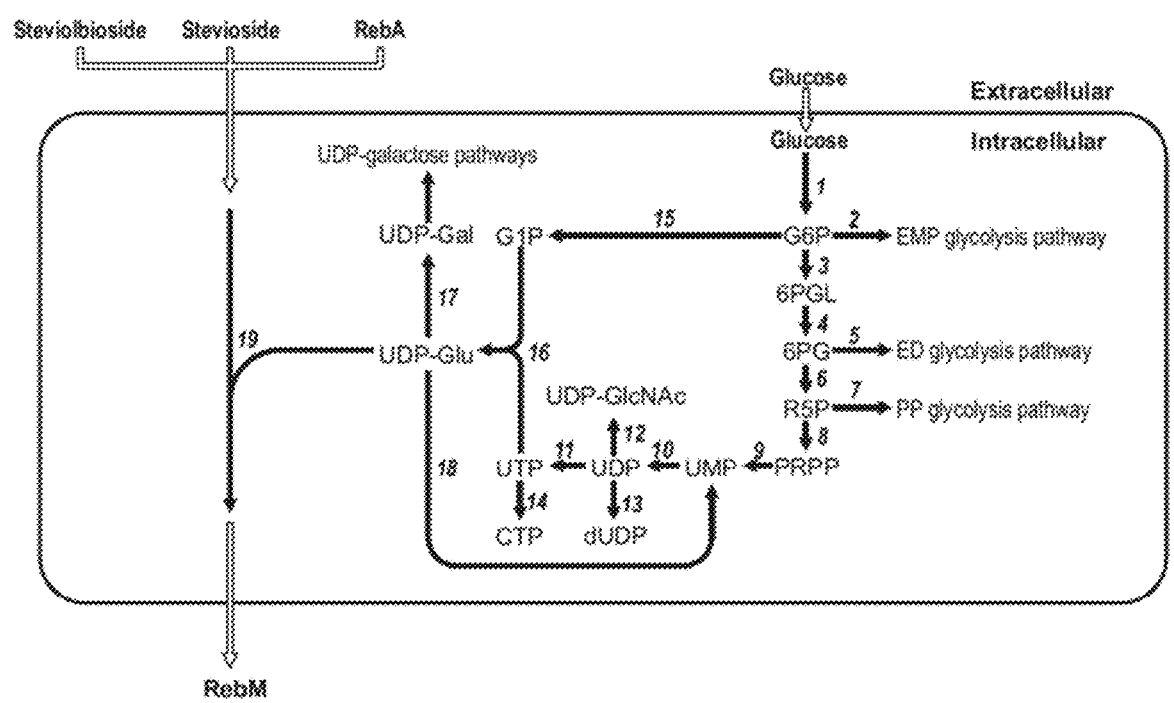
FIG. 8. Genetic modifications to increase the native *E. coli* flux to UDP-glucose. Metabolites: G6P, glucose-6-phosphate; G1P, glucose-1-phosphate; 6PGL, 6-phosphoglucono-1,5-lactone; 6PG, 6-phosphogluconate; R5P, ribose-5-phosphate; PRPP, 5-phosphoribosyl-1-pyrophosphate; UMP, uridine monophosphate; UDP, uridine diphosphate; UTP, uridine triphosphate; UDP-Glu, UDP-glucose; UDP-Gal, UDP-galactose; UDP-GlcNAc, UDP-N-acetylglucosamine; CTP, cytidine triphosphate; dUDP, deoxyuridine-diphosphate; RebA, rebaudioside A; RebM, rebaudioside M. Enzymes: 1. glk, glucokinase; 2. pgi, glucose-6-phosphate isomerase; 3. zwf, glucose-6-phosphate-1-dehydrogenase; 4. pgl, 6-phosphogluconolactonase; 5. edd, phosphogluconate dehydratase; 6. gnd, 6-phosphogluconate dehydrogenase; 7. rpiA, ribose-5-phosphate isomerase or rpe, ribulose-phosphate 3-epimerase; 8. prs, ribose-phosphate diphosphokinase; 9. pyrEF, orotate phosphoribosyltransferase and orotidine-5'phosphate-decarboxylase; 10. pyrK, uridylate kinase; 11. ndk, UDP kinase; 12. murG, N-acetylglucosaminyl transferase; 13. nrdABEF, ribonucleoside-diphosphate reductase; 14. pyrG, CTP synthase; 15. pgm, phosphoglucomutase; 16. galU, UDP-glucose pyrophosphorylase; 17. galETW, UDP-glucose-4-epimerase/galactose-1-phosphate uridylyltransferase/galactokinase/galactose-1-epimerase; 18. ushA, 5'-nucleotidase/ UDP-sugar hydrolase; 19. UGT, UDP-glycosyltransferase. The schematic illustrates the sequential genomic modifications that lead from Strain 1 to Strain 5. Strain 1 is a base *E. coli* strain. Strain 2 has a deletion of 17, and Strain 3 has an addition deletion of 18. Strain 4 was built from Strain 3 by deleting 2. Strain 5 was built from Strain 4 by overexpressing 15 and 16.

FIG. 8 shows genetic modifications to increase the native *E. coli* flux to UDP-glucose, a critical substrate for the UGTs in the RebM pathway. Greater than native flux to UDP-glucose may allow for greater RebM formation by increasing the amount of substrate available to the UGTs. The modifications resulting in Strain 5 also result in the ability of the cell to convert fed steviol glycosides to RebM. For Strain 2 and 3, enzymes that consume UDP-glucose (ushA, galETKM) were deleted. Strain 4 was built from Strain 3 by deleting an enzyme (pgi) that consumes a precursor of UDP-glucose, glucose-6-phosphate (G6P). Strain 5 was built from Strain 4 by overexpressing two enzymes that are used to convert G6P to UDP-glucose (pgm, galU) via glucose-1-phosphate (G1P).

Figure 5:
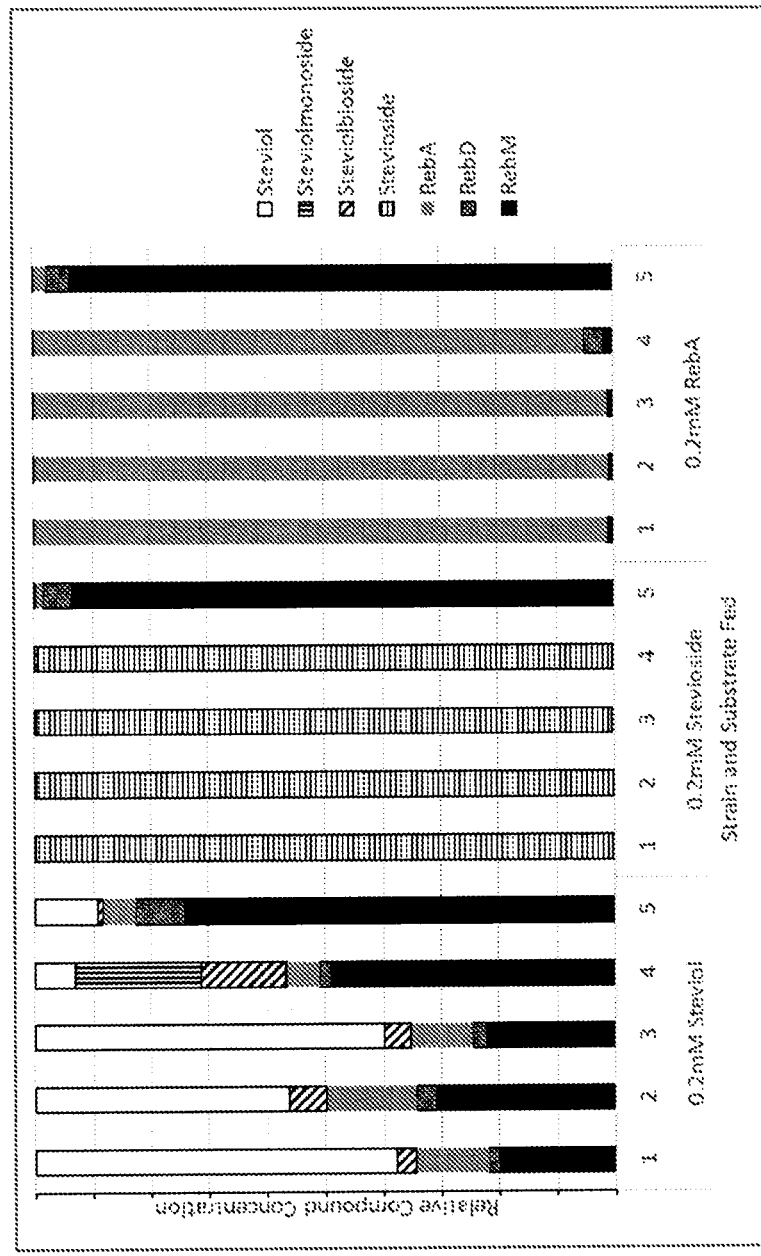
FIG. 5. Conversion of stevioside and RebA to RebM. Bioconversion of two commercially available intermediates found in leaf extract, stevioside and RebA, to RebM, is shown using Strains 1 to 5. Also shown is the bioconversion of the steviol core. The values are reported as the percentage of the total steviol glycoside composition. Conversion of steviol to RebM by all strains shows that all strains are capable of RebM formation. As was the case for steviolbioside, both stevioside and RebA are converted to RebM, but only in Strain 5. For conversion from stevioside and RebA, the ratio of RebD:RebM strongly favors RebM (1:20).

FIG. 5 shows conversion of two commercially available intermediates found in leaf extract, stevioside and RebA, to RebM. Also shown is the bioconversion of the steviol core. The values are reported as the percentage of the total steviol glycoside composition. Conversion of steviol to RebM by all strains shows that all strains are capable of RebM formation. As was the case for steviolbioside, both stevioside and RebA are converted to RebM, but only in Strain 5. It is likely that only Strain 5 makes steviol glycosides available to the UGT enzymes. For conversion from stevioside and RebA, the ratio of RebD:RebM strongly favors RebM (1:20). RebM was secreted into the media.

Figure 6:
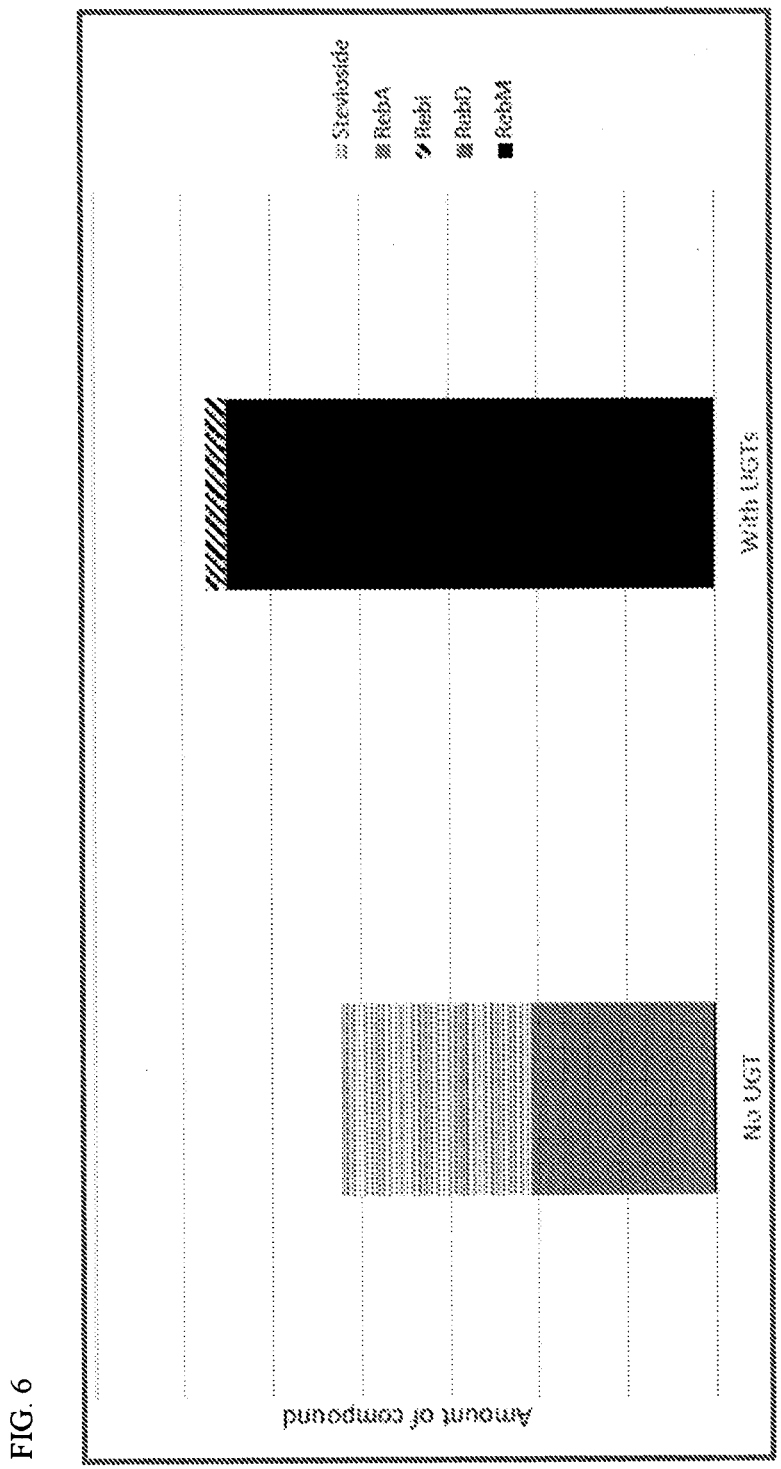
FIG. 6. Bioconversion of steviol glycosides in 96-well plates. For five major compounds in the RebM pathway, compound concentrations are shown with or without UGT enzymes expressed. Strains were fed 0.5 g/L of stevioside/RebA leaf extract and incubated with substrate for 48 hours before sampling.

FIG. 6 shows bioconversion of steviol glycosides in 96-well plates. For these studies, 76G1_L200A was replaced with MbUGT1-3_1.5. For five major compounds in the RebM pathway, compound concentrations are shown with or without UGT enzymes expressed. Strains were fed 0.5 g/L of stevioside/RebA leaf extract and incubated with substrate for 48 hours before sampling. As shown, the cells make almost exclusively RebM, with only small amounts of RebI and RebD.

Figure 7:
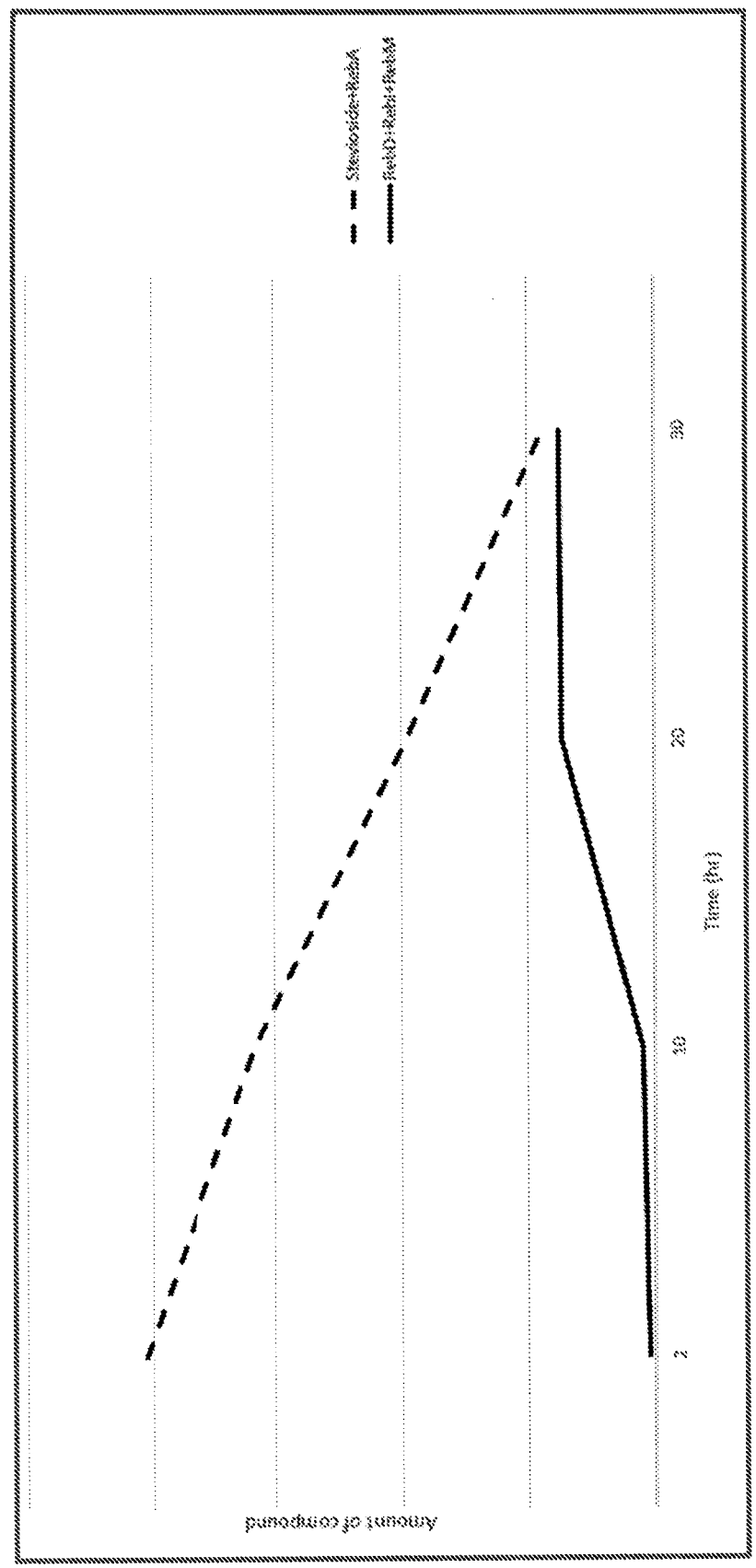
FIG. 7. Bioconversion of a stevioside/RebA leaf extract at bioreactor scale. For five major compounds in the RebM pathway, compound concentrations in the media were sampled at various time points across the fermentation. Strains were fed 2 g/L of the stevioside/RebA leaf extract and incubated with substrate for a total of 30 hours.

The strain was used for initial bioreactor experiments. Specifically, the RebM-producing strain was inoculated from a working cell bank in a 50 mL centrifuge tube containing 10 mL of LB (Luria-Bertani) broth with suitable antibiotics. The first seed was cultured for 20 hours in a shaking incubator at 37° C. After 20 hours, the second seed culture was then started by inoculating 100 mL of fermentation medium in a 500 mL Erlenmeyer flask using the first seed. This second seed was cultured for 10 hours before transferring to the bioreactors, each containing 170 mL of fermentation medium. Sampling was performed every 10 hours. Relevant metabolites in the medium were quantified using LC-MS-MS and YSI. Cell density was measured via a spectrophotometer at absorbance 600 nm. FIG. 7 shows bioconversion of a stevioside/RebA leaf extract at bioreactor scale. For five major compounds in the RebM pathway, compound concentrations in the media were sampled at various time points across the fermentation. Strains were fed 2 g/L of the stevioside/RebA leaf extract and incubated with substrate for a total of 30 hours. As shown in FIG. 7, stevioside and RebA are lost over time, with the corresponding increase in highly glycosylated products such as RebM, RebI, and RebD.

The UGT enzymes that convert pathway intermediates such as steviolbioside, stevioside, and RebA to RebM are expressed in the *E. coli* cytoplasm and thus require intermediates to become available to the UGT enzymes, likely through the action of a transporter or through increased membrane permeability.

Steviol glycosides are large molecules that likely are not taken up by native *E. coli* strains. This would explain the negligible conversion of steviolbioside to RebM by Strain 1. Strains 1-4 can take up an earlier, non-glycosylated intermediate (steviol) and convert it to RebM, suggesting the reason for negligible conversion is a lack of uptake of steviol glycosides to the cytoplasm, not inactivity of the UGT enzymes on the pathway intermediates under these conditions.

```
SEQUENCES
>SrUGT85C2 [Stevia rebaudiana]
                                    (SEQ ID NO: 1)
MDAMATTEKKPHVIFIPFPAQSHIKAMLKLAQL

LHHKGLQITFVNTDFIHNQFLESSGPHCLDGAP

GFRFETIPDGVSHSPEASIPIRESLLRSIETNF

LDRFIDLVTKLPDPPTCIISDGFLSVFTIDAAK

KLGIPVMMYWILAACGFMGFYHIHSLIEKGFAP

LKDASYLINGYLDTVIDWVPGMEGIRLKDEPLD

WSIDLNDKVLMFTTEAPQRSHKVSHHIFHTFDE

LEPSIIKILSLRYNHIYTIGPLQLLLDQIPEEK

KQTGITSLHGYSLVKEEPECFQWLQSKEPNSVV

YVNFGSTIVMSLEDMIEFGWGLANSNHYFLWII

RSNLVIGENAVLPPELEEHIKKRGFIASWCSQE

KVLKHPSVGGFLTHCGWGSTIESLSAGVPMICW

PYSWDQLINCRYICKEWEVGLEMGTKVKRDEVK

RLVQELMGEGGHKMRNKAKDWKEKARIAIAPNG

SSSLNIDKMVKEITVLARN

>SrUGT74G1 [Stevia rebaudiana]
                                    (SEQ ID NO: 2)
MAEQQKIKKSPHVLLIPFPLQGHINPFIQFGKR

LISKGVKITLVITIHTLNSTLNHSNITTISIEI

QAISDGCDEGGFMSAGESYLETFKQVGSKSLAD

LIKKLQSEGITIDAIIYDSMTEWVLDVAIEFGI

DGGSFFTQACVVNSLYYHVHKGLISLPLGETVS

VPGFPVLQRWETPLILQNHEQIQSPWSQMLFGQ

FANIDQARWVFINSFYKLEEEVIEWIRKIWNLK

VIGPTLPSMYLDKRLDDDKDNGFNLYKANHHEC

MNWLDDKPKESVVYVAFGSLVKHGPEQVEEITR

ALIDSDVNFLWVIKHKEEGKLPENLSEVIKTGK

GLIVAWCKQLDVLAHESVGCFVTHCGENSTLEA

ISLGVPVVAMPQFSDQTTNAKLLDEILGVGVRV
```

>SrUGT76G1 [Stevia rebaudiana]
(SEQ ID NO: 3)
MENKTETTVRRRRRIILFPVPFQGHINPILQLA

NVLYSKGFSITIFHINFNKPKTSNYPHFIFRFI

LDNDPQDERISNLPTHGPLAGMRIPIINEHGAD

ELRRELELLMLASEEDEEVSCLITDALWYFAQS

VADSLNLRRLVLMISSLFNFHAHVSLPQFDELG

YLDPDDKIRLEEQASGFPMLKVKDIKSAYSNWQ

ILKEILGKMIKQTKASSGVIWNSFKELEESELE

TVIREIPAPSFLIPLPKHLTASSSSLLDHDRIV

FQWLDQQPPSSVLYVSFGSTSEVDEKDFLEIAR

GLVDSKQSFLWVVRPGFVKGSTWVEPLPDGFLG

ERGRIVKWVPQQEVLAHGAIGAFWTHSGWNSTL

ESVCEGVPMIFSDFGLDQPLNARYMSDVLKVGV

YLENGWERGEIANAIRRVMVDEEGEYIRQNARV

LKQKADVSLMKGGSSYESLESLVSYISSL

>SrUGT91D1 [Stevia rebaudiana]
(SEQ ID NO: 4)
MYNVIYHQNSKAMATSDSIVDDRKQLHVATFPW

LAFGHILPFLQLSKLIAEKGHKVSFLSTIRNIQ

RLSSHISPLINVVQLTLPRVQELPEDAEATTDV

HPEDIQYLKKAVDGLQPEVIRFLEQHSPDWIIY

DFTHYWLPSIAASLGISRAYFCVITPWTIAYLA

PSSDAMINDSDGRTIVEDLTIPPKWFPFPTKVC

WRKHDLARMEPYEAPGISDGYRMGMVFKGSDCL

LFKCYHEFGTQWLPLLETLHQVPVVPVGLLPPE

IPGDEKDETWVSIKKWLDGKQKGSVVYVALGSE

ALVSQTEVVELALGLELSGLPFVWAYRKPKGPA

KSDSVELPDGFVERTRDRGLVWTSWAPQLRILS

HESVCGFLTHCGSGSIVEGLMFGHPLIMLPIFC

DQPLNARLLEDKQVGIEIPRNEEDGCLIKESVA

RSLRSVVVENEGEIYKANARALSKIYNDTKVEK

EYVSQFVDYLEKNARAVAIDHES

>SrUGT91D2 [Stevia rebaudiana]
(SEQ ID NO: 5)
MATSDSIVDDRKQLHVATFPWLAFGHILPYLQL

SKLIAEKGHKVSFLSTIRNIQRLSSHISPLINV

VQLTLPRVQELPEDAEATTDVHPEDIPYLKKAS

DGLQPEVIRFLEQHSPDWIIYDYTHYWLPSIAA

SLGISRAHFSVITPWAIAYMGPSADAMINGSDG

RTIVEDLTIPPKWFPFPTKVCWRKHDLARLVPY

KAPGISDGYRMGLVLKGSDCLLSKCYHEFGTQW

LPLLETLHQVPVVPVGLLPPEVPGDEKDETWVS

IKKWLDGKQKGSVVYVALGSEVLVSQTEVVELA

LGLELSGLPFVWAYRKPKGPAKSDSVELPDGFV

ERTRDRGLVWTSWAPQLRILSHESVCGFLTHCG

SGSIVEGLMFGHPLIMLPIFGDQPLNARLLEDK

QVGIEIPRNEEDGCLIKESVARSLRSVVVEKEG

EIYKANARELSKIYNDTKVEKEYVSQFVDYLEK

NTRAVAIDHES

>SrUGT91D2e [Stevia rebaudiana]
(SEQ ID NO: 6)
MATSDSIVDDRKQLHVATFPWLAFGHILPYLQL

SKLIAEKGHKVSFLSTIRNIQRLSSHISPLINV

VQLTLPRVQELPEDAEATTDVHPEDIPYLKKAS

DGLQPEVIRFLEQHSPDWIIYDYTHYWLPSIAA

SLGISRAHFSVITPWAIAYMGPSADAMINGSDG

RTIVEDLTIPPKWFPFPTKVCWRKHDLARLVPY

KAPGISDGYRMGLVLKGSDCLLSKCYHEFGTQW

LPLLETLHQVPVVPVGLLPPEIPGDEKDETWVS

IKKWLDGKQKGSVVYVALGSEVLVSQTEVVELA

LGLELSGLPFVWAYRKPKGPAKSDSVELPDGFV

ERTRDRGLVWTSWAPQLRILSHESVCGFLTHCG

SGSIVEGLMFGHPLIMLPIFGDQPLNARLLEDK

QVGIEIPRNEEDGCLIKESVARSLRSVVVEKEG

EIYKANARELSKIYNDTKVEKEYVSQFVDYLEK

NARAVAIDHES

>OsUGT1-2 [Oryza sativa]
(SEQ ID NO: 7)
MDSGYSSSYAAAAGMHVVICPWLAFGHLLPCLD

LAQRLASRGHRVSFVSTPRNISRLPPVRPALAP

LVAFVALPLPRVEGLPDGAESINDVPHDRPDMV

ELHRRAFDGLAAPFSEFLGTACADWVIVDVFHH

WAAAALEHKVPCAMMLLGSAHMIASIADRRLE

RAETESPAAAGQGRPAAAPTFEVARMKLIRTKG

SSGMSLAERFSLILSRSSLVVGRSCVEFEPETV

PLLSTLRGKPITFLGLMPPLHEGRREDGEDATV

RWLDAQPAKSVVYVALGSEVPLGVEKVHELALG

LELAGTRFLWALRKPIGVSDADLLPAGFEERTR

GRGVVATRWVPQMSILAHAAVGAFLTHCGWNST

IEGLMFGHPLIMLPIFGDQGPNARLIEAKNAGL

QVARNDGDGSFDREGVAAAIRAVAVEEESSKVF

QAKAKKLQEIVADMACHERYIDGFIQQLRSYKD

-continued

>MbUGTC19 [Circular permutant]
(SEQ ID NO: 8)
MAECMNWLDDKPKESVVYVAFGSLVKHGPEQVE
EITRALIDSDVNFLWVIKHKEEGKLPENLSEVI
KIGKGLIVAWCKQLDVLAHESVGCFVTHCGENS
TLEAISLGVPVVAMPQFSDQTTNAKLLDEILGV
GVRVKADENGIVRRGNLASCIKMIMEEERGVII
RKNAVKWKDLAKVAVHEGGSSDNDIVEFVSELI
KAGSGEQQKIKKSPHVLLIPFPLQGHINPFIQF
GKRLISKGVKITLVITIHTLNSTLNHSNITITS
IEIQAISDGCDEGGFMSAGESYLETFKQVGSKS
LADLIKKLQSEGITIDAIIYDSMTEWVLDVAIE
FGIDGGSFFTQACVVNSLYYHVHKGLISLPLGE
TVSVPGFPVLQRWETPLILQNHEQIQSPWSQML
FGQFANIDQARWVFINSFYKLEEEVIEWIRKIW
NLKVIGPTLPSMYLDKRLDDDKDNGFNLYKANH
H >MbUGT1, 2 [Circular permutant]
(SEQ ID NO: 9)
MAGSSGMSLAERFSLILSRSSLVVGRSCVEFEP
ETVPLLSTLRGKPITFLGLMPPLHEGRREDGED
ATVRWLDAQPAKSVVYVALGSEVPLGVEKVHEL
ALGLELAGTRFLWALRKPIGVSDADLLPAGFEE
RTRGRGVVATRWVPQMSILAHAAVGAFLTHCGW
NSTIEGLMFGHPLIMLPIFGDQGPNARLIEAKN
AGLQVARNDGDGSFDREGVAAAIRAVAVEEESS
KVFQAKAKKLQEIVADMACHERYIDGFIQQLRS
YKDDSGYSSSYAAAAGMHVVICPWLAFGHLLPC
LDLAQRLASRGHRVSFVSTPRNISRLPPVRPAL
APLVAFVALPLPRVEGLPDGAESINDVPHDRPD
MVELHRRAFDGLAAPFSEFLGTACADWVIVDVF
HHWAAAAALEHKVPCAMMLLGSAHMIASIADRR
LERAETESPAAAGQGRPAAAPTFEVARMKLIRT
K >MbUGT1-3 [Circular permutant]
(SEQ ID NO: 10)
MANWQILKEILGKMIKQTKASSGVIWNSFKELE
ESELETVIREIPAPSFLIPLPKHLTASSSSLLD
HDRIVFQWLDQQPPSSVLYVSFGSTSEVDEKDF
LEIARGLVDSKQSFLWVVRPGFVKGSTWVEPLP
DGFLGERGRIVKWVPQQEVLAHGAIGAFWTHSG
WNSTLESVCEGVPMIFSDFGLDQPLNARYMSDV
LKVGVYLENGWERGEIANAIRRVMVDEEGEYIR
QNARVLKQKADVSLMKGGSSYESLESLVSYISS LENKTETTVRRRRRIILFPVPFQGHINPILQLA
NVLYSKGFSITIFHINFNKPKTSNYPHFIFRFI
LDNDPQDERISNLPTHGPLAGMRIPIINEHGAD
ELRRELELLMLASEEDEEVSCLITDALWYFAQS
VADSLNLRRLVLMISSLFNFHAHVSLPQFDELG
YLDPDDKIRLEEQASGFPMLKVKDIKSAYS >MbUGT1, 2.2 [Circular permutant]
(SEQ ID NO: 11)
MATKGSSGMSLAERFWLILSRSSLVVGRSCVEF
EPETVPLLSTLRGKPITFLGLMPPLHEGRREDG
EDATVRWLDAQPAKSVVYVALGSEVPLGVEKVH
ELALGLELAGTRFLWALRKPIGVSDADLLPAGF
EERTRGRGVVATRWVPQMSILAHAAVGAFLTHC
GWNSTIEGLMFGHPLIMLPIFGDQGPNARLIEA
KNAGLQVARNDGDGSFDREGVAAAIRAVAVEEE
SSKVFQAKAKKLQEIVADMACHERYIDGFIQQL
RSYKDDSGYSSSYAAAAGMHVVICPWLAFGHLL
PCLDLAQRLASRGHRVSFVSTPRNISRLPPVRP
ALAPLVAFVALPLPRVEGLPDGAESINDVPHDR
PDMVELHRRAFDGLAAPFSEFLGTACADWVIVD
VFHHWAAAAALEHKVPCAMMLLGSAEMIASIAD
ERLEHAETESPAAAGQGRPAAAPTFEVARMKLI
R >MbUGTC19-2 [Circular permutant]
(SEQ ID NO: 12)
MANHHECMNWLDDKPKESVVYVAFGSLVKHGPE
QVEEITRALIDSDVNFLWVIKHKEEGKLPENLS
EVIKTGKGLIVAWCKQLDVLAHESVGCFVTHCG
ENSTLEAISLGVPVVAMPQFSDQTTNAKLLDEI
LGVGVRVKADENGIVRRGNLASCIKMIMEEERG
VIIRKNAVKWKDLAKVAVHEGGSSDNDIVEFVS
ELIKAGSGEQQKIKKSPHVLLIPFPLQGHINPF
IQFGKRLISKGVKITLVITIHTLNSTLNHSNIT
TTSIEIQAISDGCDEGGFMSAGESYLETFKQVG
SKSLADLIKKLQSEGITIDAIIYDSMTEWVLDV
AIEFGIDGGSFFTQACVVNSLYYHVHKGLISLP
LGETVSVPGFPVLQRWETPLILQNHEQIQSPWS
QMLFGQFANIDQARWVFINSFYKLEEEVIEWIR
KIWNLKVIGPTLPSMYLDKRLDDDKDNGFNLYK
A >MbUGTC13 (*Stevia rebaudiana* UGT85C2, P2151)
(SEQ ID NO: 13)
MADAMATTEKKPHVIFIPFPAQSHIKAMLKLAQ
LLHHKGLQITEVNTDFIHNQFLESSGPHCLDGA
PGFRFETIPDGVSHSPEASIPIRESLLRSIETN
FLDRFIDLVTKLPDPPTCIISDGFLSVFTIDAA
KKLGIPVMMYWILAACGFMGFYHIHSLIEKGFA
PLKDASYLINGYLDTVIDWVPGMEGIRLKDFPL
DWSIDLNDKVLMFTTEATQRSHKVSHHIFHTFD
ELEPSIIKILSLRYNHIYTIGPLQLLLDQIPEE
KKQTGITSLHGYSLVKEEPECFQWLQSKEPNSV
VYVNFGSTIVMSLEDMIEFGWGLANSNHYFLWI
IRSNLVIGENAVLPPELEEHIKKRGFIASWCSQ
EKVLKHPSVGGFLTHCGWGSTIESLSAGVPMIC
WPYSWDQLINCRYICKEWEVGLEMGTKVKRDEV
KRLVQELMGEGGHKMRNKAKDWKEKARIAIAPN
GSSSLNIDKMVKEITVLARN >76G1 L200A [*Stevia rebaudiana*, L200A]
(SEQ ID NO: 14)
MAENKTETTVRRRRIILFPVPFQGHINPILQL
ANVLYSKGFSITIFHINFNKPKTSNYPHFIFRF
ILDNDPQDERISNLPTHGPLAGMRIPIINEHGA
DELRRELELLMLASEEDEEVSCLITDALWYFAQ
SVADSLNLRRLVLMISSLFNFHAHVSLPQFDEL
GYLDPDDKIRLEEQASGFPMLKVKDIKSAYSNW
QIAKEILGKMIKQTKASSGVIWNSFKELEESEL
ETVIREIPAPSFLIPLPKHLTASSSSLLDHDRT
VFQWLDQQPPSSVLYVSFGSTSEVDEKDFLEIA
RGLVDSKQSFLWVVRPGFVKGSTWVEPLPDGFL
GERGRIVKWVPQQEVLAHGAIGAFWTHGWNST
LESVCEGVPMIFSDFGLDQPLNARYMSDVLKVG
VYLENGWERGEIANAIRRVMDEEGEYIRQNAR
VLKQKADVSLMKGGSSYESLESLVSYISSL >MbUGT1-3_1 [Circular permutant]
(SEQ ID NO: 15)
MAFLWVVRPGFVKGSTWVEPLPDGFLGERGRIV
KWVPQQEVLAHGAIGAFWTHGGWNSTLESVCEG
VPMIFSDFGLDQPLNARYMSDVLKVGVYLENGW
ERGEIANAIRRLMVDEEGEYIRQNARVLKQKAD
VSLMKGGSSYESLESLVSYISSLGSGGSGGSGR
RRRIILFPVPFQGHINPMLQLANVLYSKGFSIT
IFHINFNKPKTSNYPHFTFRFILDNDPQDERIS
NLPTHGPLAGMRIPIINEHGADELRRELELLML ASEEDEEVSCLITDALWYFAQSVADSLNLRRLV
LMISSLFNFHAHVSLPQFDELGYLDPDDKIRLE
EQASGFPMLKVKDIKSAYSNWQIAKEILGKMIK
QTKASSGVIWNSFKELEESELETVIREIPAPSF
LIPLPKHLTASSSSLLDHDRIVFQWLDQQPPSS
VLYVSFGSTSEVDEKDFLEIARGLVDSQS >MbUGT1-3_1.5 [Circular permutant]
(SEQ ID NO: 16)
MAFLWVVRPGFVKGSTWVEPLPDGFLGERGRIV
KWVPQQEVLAHGAIGAFWTHGGWNSTLESVCEG
VPMIFSDFGLDQPLNARYMSDVLKVGVYLENGW
ERGEIANAIRRLMVDEEGEYIRQNARVLKQKAD
VSLMKGGSSYESLESLVSYISSLGSGGSGGSGR
RRRIILFPVPFQGHINPMLQLANVLYSKGFSIT
IFHINFNKPKTSNYPHFTFRFILDNDPQTTHGP
LAGMRIPIINEHGADELRRELELQMLASEEDEE
VSCLITDALWYFAQSVADSLNLPRLVLMISSLF
NFHAHVSLPQFDELGYLDPDDKIRLEEQASGFP
MLKVKDIKSAYSNWQIAKEILGKMIKQTKASSG
VIWNSFKELEESELETVIREIPAPSFLIPLPKH
LTASSSSLLDHDRIVFQWLDQQPPSSVLYVSFG
STSEVDEKDFLEIARGLVDSQS >MbUGT1-3_2 [Circular permutant]
(SEQ ID NO: 17)
MAFLWVVRPGFVKGSTWVEPLPDGFLGERGRIV
KWVPQQEVLAHGAIGAFWTHGGWNSTLESVCEG
VPMIFSDFGLDQPLNARYMSDVLKVGVYLENGW
ERGEIANAIRRLMVDEEGEYIRQNARVLKQKAD
VSLMKGGSSYESLESLVSYISSLGSGGSGRRRR
IILFPVPFQGHINPMLQLANVLYSKGFSITIFH
INFNKPKTSNYPHFTFRFILDNDPQDERISNLP
THGPLAGMRIPIINEHGADELRRELELQMLASE
EDEEVSCLITDALWYFAQSVADSLNLPRLVLMI
SSLFNFHAHVSLPQFDELGYLDPDDKIRLEEQA
SGFPMLKVKDIKSAYSNWQIAKEILGKMIKQTK
ASSGVIWNSFKELEESELETVIREIPAPSFLIP
LPKHLTASSSSLLEHDRIVFQWLDQQPPSSVLY
VSFGSTSEVDEKDFLEIARGLVDSQS >SgUGT720-269-1 (*Siraitia grosvenorii*)
(SEQ ID NO: 18)
MEDRNAMDMSRIKYRPQPLRPASMVQPRVLLFP
FPALGHVKPFLSLAELLSDAGIDVVFLSTEYNH -continued
```
RRISNTEALASREPTLHFETIPDGLPPNESRAL

ADGPLYFSMREGTKPRFRQLIQSLNDGRWPITC

IITDIMLSSPIEVAEEFGIPVIAFCPCSARYLS

IHFFIPKLVEEGQIPYADDDPIGEIQGVPLFEG

LLRRNHLPGSWSDKSADISFSHGLINQTLAAGR

ASALILNIFDELEAPFLTHLSSIENKIYTIGPL

HALSKSRLGDSSSSASALSGFWKEDRACMSWLD

CQPPRSVVFVSFGSTMKMKADELREFWYGLVSS

GKPFLCVLRSDVVSGGEAAELIEQMAEEEGAGG

KLGMVVEWAAQEKVLSHPAVGGFLTHCGWNSTV

ESIAAGVPMMCWPILGDQPSNATWIDRVWKIGV

ERNNREWDRLIVEKMVRALMEGQKRVEIQRSME

KLSKLANEKVVRGINLHPTISLKKDTPTISEHP

RHEFENMRGMNYEMLVGNAIKSPILIKK
```

>SgUGT94-289-3
(Siraitia grosvenorii)
(SEQ ID NO: 19)
```
MTIFFSVEILVLGIAEFAAIAMDAAQQGDITTI

LMLPWLGYGHLSAFLELAKSLSRRNFHIYFCST

SVNLDAIKPKLPSSFSDSIQFVELHLPSSPEFP

PHLHTINGLPPILMPALHQAFSMAAQHFESILQ

TLAPHLLIYDSLQPWAPRVASSLKIPAINFNIT

GVFVISQGLHPIHYPHSKFPFSEFVLHNHWKAM

YSTADGASTERTRKRGEAFLYCLHASCSVILIN

SFRELEGKYMDYLSVLLNKKVVPVGPLVYEPNQ

DGEDEGYSSIKNWLDKKEPSSIVFVSFGSEYFP

SKEEMEEIAHGLEASEVNFIWVVRFPQGDNTSG

IEDALPKGFLERAGERGMVVKGWAPQAKILKHW

SIGGFVSHCGWNSVMESMMFGVPIIGVPMHVDQ

PFNAGLVEEAGVGVEAKRDPDGKIQRDEVAKLI

KEVVVEKTREDVRKKAREMSEILRSKGEEKEDE

MVAEISLLLKI
```

>SgUGT74-345-2
(Siraitia grosvenorii)
(SEQ ID NO: 20)
```
MDETTVNGGRRASDVVVFAFPRHGHMSPMLQFS

KRLVSKGLRVTFLITTSATESLRLNLPPSSSLD

LQVISDVPESNDIATLEGYLRSFKATVSKTLAD

FIDGIGNPPKFIVYDSVMPWVQEVARGRGLDAA

PFFTQSSAVNHILNHVYGGSLSIPAPENTAVSL

PSMPVLQAEDLPAFPDDPEVVMNFMTSQFSNFQ

DAKWIFFNIFDQLECKKQSQVVNWMADRWPIKT

VGPTIPSAYLDDGRLEDDRAFGLNLLKPEDGKN

TRQWQWLDSKDTASVLYISFGSLAILQEEQVKE

LAYFLKDINLSFLWVLRDSELQKLPHNFVQETS

HRGLVVNWCSQLQVLSHRAVSCFVTHCGWNSTL

EALSLGVPMVAIPQWVDQTTNAKFVADVWRGV

RVKKKDERIVIKEELEASIRQVVQGEGRNEFKH

NAIKWKKLAKEAVDEGGSSDKNIEEFVKTIA
```

>SgUGT75-281-2
(Siraitia grosvenorii)
(SEQ ID NO: 21)
```
MGDNGDGGEKKELKENVKKGKELGRQAIGEGYI

NPSLQLARRLISLGVNVTFATTVLAGRRMKNKT

HQTATTPGLSFATFSDGFDDETLKPNGDLTHYF

SELRRCGSESLTHLITSAANEGRPITFVIYSLL

LSWAADIASTYDIPSALFFAQPATVLALYFYYF

HGYGDTICSKLQDPSSYIELPGLPLLTSQDMPS

FFSPSGPHAFILPPMREQAEFLGRQSQPKVLVN

IFDALEADALRAIDKLKMLAIGPLIPSALLGGN

DSSDASFCGDLFQVSSEDYIEWLNSKPDSSVVY

ISVGSICVLSDEQEDELVHALLNSGHTFLWVKR

SKENNEGVKQETDEEKLKKLEEQGKMVSWCRQV

EVLKHPALGCFLTHCGWNSTIESLVSGLPVVAF

PQQIDQATNAKLIEDVWKIGVRVKANTEGIVER

EEIRRCLDLVMGSRDGQKEEIERNAKKWKELAR

QAIGEGGSSDSNLKTFLWEIDLEI
```

>SgUGT720-269-4
(Siraitia grosvenorii)
(SEQ ID NO: 22)
```
MAEQAHDLLHVLLFPFPAEGHIKPFLCLAELLC

NAGFHVTFLNIDYNHRRLHNLHLLAARFPSLHF

ESISDGLPPDQPRDILDPKFFISICQVIKPLFR

ELLLSYKRISSVQTGRPPITCVITDVIFRFPID

VAEELDIPVFSFCIFSARFMPLYFWIPKLIEDG

QLPYPNGNINQKLYGVAPEAEGLLRCKDLPGHW

AFADELKDDQLNFVDQTTASSRSSGLILNIFDD

LEAPFLGRLSTIFKKIYAVGPIHSLLNSHHCGL

WKEDHSCLAWLDSRAAKSVVFVSFGSLVKITSR

QLMEFWHGLLNSGKSFLFVLRSDVVEGDDEKQV

VKEIYETKAEGKWLVVGWAPQEKVLAHEAVGGF

LTHSGWNSILESIAAGVPMISCPKIGDQSSNCT

WISKVWKIGLEMEDRYDRVSVETMVRSIMEQEG

EKMQKTIAELAKQAKYKVSKDGISYQNLECLIQ

DIKKLNQIEGFINNPNFSDLLRV
```

-continued

>SgUGT94-289-2
(Siraitia grosvenorii)
(SEQ ID NO: 23)
MDAQQGHTITILMLPWVGYGHLLPFLELAKSLS

RRKLFHIYFCSTSVSLDAIKPKLPPSISSDDSI

QLVELRLPSSPELPPHLHTINGLPSHLMPALHQ

AFVMAAQHFQVILQTLAPHLLIYDILQPWAPQV

ASSLNIPAINFSTTGASMLSRILHPTHYPSSKF

PISEFVLHNHWRAMYTTADGALTEEGHKIEETL

ANCLHISCGVVLVNSFRELETKYIDYLSVLLNK

KVVPVGPLVYEPNQEGEDEGYSSIKNWLDKKEP

SSIVEVSEGTEYFPSKEEMEEIAYGLELSEVNF

IWVLRFPQGDSTSTIEDALPKGFLERAGERAMV

VKGWAPQAKILKHWSIGGLVSHCGWNSMMEGMM

FGVPIIAVPMHLDQPFNAGLVEEAGVGVEAKRD

SDGKIQREEVAKSIKEVVIEKTREDVRKKAREM

DTKHGPTYFSRSKVSSFGRLYKINRPTILTVGR

FWSKQIKMKRE

>SgUGT94-289-1
(Siraitia grosvenorii)
(SEQ ID NO: 24)
MDAQRGHTITILMFPWLGYGHLSAFLELAKSLS

RRNFHIYFCSTSVNLDAIKPKLPSSSSSDSIQL

VELCLPSSPDQLPPHLHTTNALPPHLMPTLHQA

FSMAAQHFAAILHTLAPHLLIYDSFQPWAPQLA

SSLNIPAINFNITGASVLIRMLHATHYPSSKFP

ISEFVLHDYWKAMYSAAGGAVIKKDHKIGETLA

NCLHASCSVILINSFRELEEKYMDYLSVLLNKK

VVPVGPLVYEPNQDGEDEGYSSIKNWLDKKEPS

STVFVSFGSEYFPSKEEMEEIAHGLEASEVHFI

WVVRFPQGDNISAIEDALPKGFLERVGERGMVV

KGWAPQAKILKHWSIGGFVSHCGWNSVMESMMF

GVPIIGVPMHLDQPFNAGLAEEAGVGVEAKRDP

DGKIQRDEVAKLIKEVVVEKTREDVRKKAREMS

EILRSKGEEKMDEMVAAISLFLKI

>XP_022151474.1 7-deoxyloganetic
acid glucosyltransferase-like
[Nbmordica charantia]
(SEQ ID NO: 25)
MAQPQTQARVLVFPYPTVGHIKPFLSLAELLAD

GGLDVVFLSTEYNHRRIPNLEALASRFPILHFD

TIPDGLPIDKPRVIIGGELYISMRDGVKQRLRQ

VLQSYNDGSSPITCVICDVMLSGPIEAAEELGI

PVVTFCPYSARYLCAHFVMPKLIEEGQIPFIDG

NLAGEIQGVPLFGGLLRRDHLPGFWFVKSLSDE

VWSHAFLNQTLAVGRISALIINTLDELEAPFLA

HLSSTFDKIYPIGPLDALSKSRLGDSSSSSTVL

TAFWKEDQACMSWLDSQPPKSVIFVSFGSTMRM

TADKLVEFWHGLVNSGTRFLCVLRSDIVEGGGA

ADLIKQVGEIGNGIVVEWAAQEKVLAHRAVGGF

LTHCGWNSTMESIAAGVPMMCWQIYGDQMINAT

WIGKVWKIGIERDDKWDRSTVEKMIKELMEGEK

GAEIQRSMEKFSKLANDKVVKGGISFENLELIV

EYLKKLKPSN

>XP_022151546.1 7-deoxyloganetic
acid glucosyltransferase-like
[Nbmordica charantia]
(SEQ ID NO: 26)
MAQPRVLLFPFPAMGHVKPFLSLAELLSDAGVE

VVFLSTEYNHRRIPDIGALAARFPILHFETIPD

GLPPDQPRVLADGHLYFSMLDGTKPRFRQLIQS

LNGNPRPITCIINDVMLSSPIEVAEEFGIPVIA

FCPCSARFLSVHFFMPNFIEEAQIPYTDENPMG

KIEEATVFEGLLRRKDLPGLWCAKSSNISFSHR

FINQTIAAGRASALILNIFDELESPFLNHLSSI

FPKIYCIGPLNALSRSRLGKSSSSSSALAGFWK

EDQAYMSWLESQPPRSVIFVSFGSTMKMEAWKL

AEFWYGLVNSGSPFLFVFRPDCVINSGDAAEVM

EGRGRGMVVEWASQEKVLAHPAVGGFLTHCGWN

STVESIVAGVPMMCCPIVADQLSNATWIHKVWK

IGIEGDEKWDRSTVEMMIKELMESQKGTEIRTS

IEMLSKLANEKVVKGGISLNNFELLVEDIKTLR

RPYT

>XP_022151514.1 7-deoxyloganetic
acid glucosyltransferase-like
[Nbmordica charantia]
(SEQ ID NO: 27)
MEQSDSNSDDHQHHVLLFPFPAKGHIKPFLCLA

QLLCGAGLQVTFLNIDHNHRRIDDRHRRLLATQ

FPMLHFKSISDGLPPDHPRDLLDGKLIASMRRV

IESLFRQLLLSYNGYGNGINNVSNSGRRPPISC

VITDVIFSFPVEVAEELGIFVFSFATFSARFLF

LYFWIPKLIQEGQLPFPDGKINQELYGVPGAEG

IIRCKDLPGSWSVEAVAKNDPMNFVKQTLASSR

SSGLILNIFEDLEAPFVTHLSNIFDKIYTIGPI

HSLLGTSHCGLWKEDYACLAWLDARPRKSVVFV

SFGSLVKITSRELMELWHGLVSSGKSFLLVLRS

DVVEGEDEEQVVKEILESNGEGKWLVVGWAPQE

EVLAHEAIGGFLTHSGWNSTMESIAAGVPMVCW

PKIGDQPSNCTWVSRVWKVGLEMEERYDRSTVA

RMARSMMEQEGKEMERRIAELAKRVKYRVGKDG

ESYRNLESLIRDIKITKSSN

>XP_004147933.2 PREDICTED:
7-deoxyloganetic acid
glucosyltransferase-like
[Cucumis sativus]
(SEQ ID NO: 28)
MGLSPIDHVLLFPFPAKGHIKPFFCLAHLLCNA

GLRVTFLSTEHHHQKLHNLTHLAAQIPSLHFQS

ISDGLSLDHPRNLLDGQLFKSMPQVIKPLFRQL

LLSYKDGISPITCVITDLILRFPMDVAQELDIP

VFCFSTFSARFLFLYFSIPKLLEDGQIPYPEGN

SNQVLHGIPGAEGLLRCKDLPGYWSVEAVANYN

PMNFVNQTIATSKSHGLILNIFDELEVPFITNL

SKIYKKVYTIGPIHSLLKKSVQTQYEFWKEDHS

CLAWLDSQPPRSVMFVSEGSIVKLKSSQLKEFW

NGLVDSGKAFLLVLRSDALVEETGEEDEKQKEL

VIKEIMETKEEGRWVIVNWAPQEKVLEHKAIGG

FLTHSGWNSTLESVAVGVPMVSWPQIGDQPSNA

TWLSKVWKIGVEMEDSYDRSTVESKVRSIMEHE

DKKMENAIVELAKRVDDRVSKEGTSYQNLQRLI

EDIEGFKLN

>XP_022978164.1 7-deoxyloganetic
acid glucosyltransferase-like
[Cucurbita maxima]
(SEQ ID NO: 29)
MELSHTHHVLLFPFPAKGHIKPFFSLAQLLCNA

GLRVTFLNIDHHHRRIHDLNRLAAQLPTLHFDS

VSDGLPPDEPRNVEDGKLYESIRQVISSLFREL

LVSYNNGTSSGRPPITCVITDVMFRFPIDIAEE

LGIFVFIFSTFSARFLFLIFWIPKLLEDGQLRY

PEQELHGVPGAEGLIRWKDLPGFWSVEDVADWD

PMNFVNQTLATSRSSGLILNIFDELEAPFLTSL

SKIYKKIYSLGPINSLLKNFQSQPQYNLWKEDH

SCMAWLDSQPRKSVVFVSFGSVVKLISRQLMEF

WNGLVNSGMPFLLVLRSDVIEAGEEVVREIMER

KAEGRWVIVSWAPQEEVLAHDAVGGFLTHSGWN

STLESLAAGVPMISWPQIGDQTSNSTWISKVWR

IGLQLEDGFDSSTIETMVRSIMDQTMEKTVAEL

AERAKNRASKNGTSYRNFQTLIQDITNIIETHI

>XP_022950128.1 7-deoxyloganetic
acid glucosyltransferase-like
[Cucurbita moschata]
(SEQ ID NO: 30)
MELSPTHHLLLFPFPAKGHIKPFFSLAQLLCNA

GARVTFLNIDHHHRRIHDLDRLAAQLPTLHFDS

VSDGLPPDESRNVEDGKLYESIRQVISSLFREL

LVSYNNGTSSGRPPITCVITDCMFRFPIDIAEE

LGIFVFIFSTFSARFLFLFFWIPKLLEDGQLRY

PEQELHGVPGAEGLIRCKDLPGFLSDEDVAHWK

PINFVNQILATSRSSGLILNIFDELEAPFLTSL

SKIYKKIYSLGPINSLLKNFQSQPQYNLWKEDH

SCMAWLDSQPPKSVVFVSFGSVVKLINRQLVEF

WNGLVNSGKPFLLVLRSDVIEAGEEVVRENMER

KAEGRWMIVSWAPQEEVLAHDAVGGFLTHSGWN

STLESLAAGVPMISWIQIGDQTSNSTWVSKVWR

IGLQLEDGFDSFTIETMVRSVMDQTMEKTVAEL

AERAKNRASKNGTSYRNFQTLIQDITNIIETHI

>XP_020422423.1 7-deoxyloganetic
acid glucosyltransferase
[Prunus persica]
(SEQ ID NO: 31)
MAMKQPHVIIFPFPLQGHMKPLLCLAELLCHAG

LHVTYVNTHHNHQRLANRQALSTHFPILHFESI

SDGLPEDDPRILNSQLLIALKTSIRPHFRELLK

TISLKAESNDTLVPPPSCIMIDGLVTFAFDVAE

ELGLPILSFNVPCPRYLWICLCLPKLIENGQLP

FQDDDMNVEITGVPGMEGLLHRDLPGFCRVKQ

ADHPSLQFAINETQTLKRASALILDTVYELDAP

CISHMALMFPKIYILGPLHALLNSQIGDMSRGL

ASHGSLWKSDLNCMTWLDSQPSKSIIYVSFGTL

VHLTRAQVIEFWYGLVNSGHPFLWVMRSDITSG

DHQIPAELENGTKERGCIVDWVSQEEVLAHKSV

GGFLTHSGWNSTLESIVAGLPMICWPKLGDHYI

ISSTVCRQWKIGLQLNENCDRSNIESMVQTLMG

SKREEIQSSMDAISKLSRDSVAEGGSSHNNLEQ

LIEYIRNLQHQN

>E0Y07351.1 UDP-glucosyl transferase
85A3, putative
[Theobroma cacao]
(SEQ ID NO: 32)
MRQPHVLVLPFPAQGHIKPMLCLAELLCQAGLR

VTFLNTHHSHRRLNNLQDLSTRFPILHFESVSD

GLPEDHPRNLVHFMHLVHSIKNVIKPLLRDLLT

SLSLKTDIPPVSCIIADGILSFAIDVAEELQIK

VIIFRTISSCCLWSYLCVPKLIQQGELQFSDSD

MGQKVSSVPEMKGSLRLHDRPYSFGLKQLEDPN

FQFFVSETQAMTRASAVIENTEDSLEAPVLSQM

IPLLPKVYTIGPLHALRKARLGDLSQHSSENGN

LREADHNCITWLDSQPLRSVVYVSFGSHVVLIS

-continued

EELLEFWHGLVNSGKRFLWVLRPDIIAGEKDHN

QIIAREPDLGTKEKGLLVDWAPQEEVLAHPSVG

GFLTHCGWNSTLESMVAGVPMLCWPKLPDQLVN

SSCVSEVWKIGLDLKDMCDRSTVEKMVRALMED

RREEVMRSVDGISKLARESVSHGGSSSSNLEML

IQELET

>XP_022155979.1 beta-D-glucosyl
crocetin beta-1,6-
glucosyltransferase-like
[Momordica charantia]
(SEQ ID NO: 33)
MDAHQQAEHTITILMLPWVGYGHLTAYLELAKA

LSRRNFHIYYCSTPVNIESIKPKLTIPCSSIQF

VELHLPSSDDLPPNLHTINGLPSHLMPTLHQAF

SAAAPLFEEILQTLCPHLLIYDSLQPWAPKIAS

SLKIPALNENTSGVSVIAQALHAIHHPDSKFPL

SDFILHNYWKSTYTTADGGASEKTRRAREAFLY

CLNSSGNAILINTFRELEGEYIDYLSLLLNKKV

IPIGPLVYEPNQDEDQDEEYRSIKNWLDKKEPC

STVEVSEGSEYFPSNEEMEEIAPGLEESGANFI

WVVREPKLENRNGIIEEGLLERAGERGMVIKEW

APQARILRHGSIGGFVSHCGWNSVMESIICGVP

VIGVPMRVDQPYNAGLVEEAGVGVEAKRDPDGK

IQRHEVSKLIKQVVVEKTRDDVRKKVAQMSEIL

RRKGDEKIDEMVALISLLPKG

>XP_022986080.1 beta-D-glucosyl
crocetin beta-1,6-
glucosyltransferase-like
[Cucurbita maxima]
(SEQ ID NO: 34)
MDAQKAVDTPPTIVLMLPWIGYGHLSAYLELAK

ALSRRNFHVYFCSTPVNLDSIKPNLIPPPPSSIQ

FVDLHLPSSPELPPHLHTINGLPSHLKPILHQA

FSAAAQHFEAILQILSPHLLIYDSLQPWAPRIA

SSLNIPAINFNITAVSIIAHALHSVHYPDSKFP

FSDEVLHDYWKAKYTTADGATSEKIRRGAEAFL

YCLNASCDVVLVNSFRELEGEYMDYLSVLLKKK

VVSVGPLVYEPSEGEEDEEYWRIKKWLDEKEAL

STVLVSEGSEYFPSKEEMEEIAHGLEESEANFI

WVVREPKGEESCRGIEEALPKGFVERAGERAMV

VKKWAPQGKILKHGSIGGFVSHCGWNSVLESIR

FGVPVIGVPMHLDQPYNAGLLEEAGIGVEAKRD

ADGKIQRDQVASLIKRVVVEKTREDIWKIVREM

REVLRRRDDDMIDEMVAEISVVLKI

>XP_022156002.1 beta-D-glucosyl
crocetin beta-1,6-
glucosyltransferase-like
[Momordica charantia]
(SEQ ID NO: 35)
MDARQQAEHTITILMLPWVGYGHLSAYLELAKA

LSRRNFHIYYCSTPVNIESIKPKLTIPCSSIQF

VELHLPFSDDLPPNLHTINGLPSHLMPALHQAF

SAAAPLFEAILQTLCPHLLIYDSLQPWAPQIAS

SLKIPALNENTIGVSVIARALHTIHHPDSKFPL

SEIVLHNYWKATHATADGANPEKFRRDLEALLC

CLHSSCNAILINTFRELEGEYIDYLSLLLNKKV

IPIGPLVYEPNQDEEQDEEYRSIKNWLDKKEPY

STIFVSEGSEYFPSNEEMEEIARGLEESGANFI

WVVREHKLENGNGITEEGLLERAGERGMVIQGW

APQARILRHGSIGGFVSHCGWNSVMESIICGVP

VIGVPMGLDQPYNAGLVEEAGVGVEAKRDPDGK

IQRHEVSKLIKQVVVEKTRDDVRKKVAQMSEIL

RRKGDEKIDEMVALISLLLKG

>XP_022943327.1 beta-D-glucosyl
crocetin beta-1,6-
glucosyltransferase-like
[Cucurbita moschata]
(SEQ ID NO: 36)
MDAQKAVDTPPTIVLMLPWIGYGHLSAYLELAK

ALSRRNFHVYFCSTPVNLDSIKPNLIPPPPSIQ

FVDLHLPSSPELPPHLHTINGLPSHLKPILHQA

FSAAAQHFEAILQILSPHLLIYDSLQPWAPRIA

SSLNIPAINFNITAVSIIAHALHSVHYPDSKFP

FSDEVLHDYWKAKYTTADGATSEKTRRGVEAFL

YCLNASCDVVLVNSFRELEGEYMDYLSVLLKKK

VVSVGPLVYEPSEGEEDEEYWRIKKWLDEKEAL

STVLVSFGSEYFPPKEEMEEIAHGLEESEANFI

WVVRFPKGEESSSRGIEEALPKGFVERAGERAM

VVKKWAPQGKILKHGSIGGFVSHCGWNSVLESI

RFGVPVIGAPMHLDQPYNAGLLEEAGIGVEAKR

DADGKIQRDQVASLIKQVVVEKTREDIWKKVRE

MREVLRRRDDDDMMIDEMVAVISVVLKI

>XP_022996307.1 beta-D-glucosyl
crocetin beta-1,6-
glucosyltransferase-like
[Cucurbita maxima]
(SEQ ID NO: 37)
MSSNLFLKISIPFGRLRDSALNCSVFHCKLHLA

IAIAMDAQQAANKSPTATTIFMLPWAGYGHLSA

YLELAKALSTRNFHIYFCSTPVSLASIKPRLIP

SCSSIQFVELHLPSSDEFPPHLHTINGLPSRLV

PTFHQAFSEAAQTFEAFLQTLRPHLLIYDSLQP

-continued
WAPRIASSLNIPAINFFTAGAFAVSHVLRAFHY

PDSQFPSSDFVLHSRWKIKNITAESPTQAKLPK

IGEAIGYCLNASRGVILINSFRELEGKYIDYLS

VILKKRVFPIGPLVYQPNQDEEDEDYSRIKNWL

DRKEASSTVLVSFGSEFFLSKEETEAIAHGLEQ

SEANFIWGIRFPKGAKKNAIEEALPEGFLERAG

GRAMVVEEMVPQGKILKHGSIGGFVSHCGWNSA

MESIVCGVPIIGIPMQVDQPFNAGILEEAGVGV

EAKRDSDGKIQRDEVAKLIKEVVVERTREDIRN

KLEKINEILRSRREEKLDELATEISLLSRN

>XP_022957664.1 beta-D-glucosyl
crocetin beta-1,6-
glucosyltransferase-like
[Cucurbita moschata]
(SEQ ID NO: 38)
MDAQQAANKSPTASTIFMLPWVGYGHLSAYEL

AKALSTRNFHVYFCSTPVSLASIKPRLIPSCSS

IQFVELHLPSSDEFPPHLHTINGLPAHLVPTIH

QAFAAAAQTFEAFLQTLRPHLLIYDSLQPWAPR

IASSLNIPAINFFTAGAFAVSHVLRAFHYPDSQ

FPSSDEVLHSRWKIKNITAESPIQVKIPKIGEA

IGYCLNASRGVILINSFRELEGKYIDYLSVILK

KRVLPIGPLVYQPNQDEEDEDYSRIKNWLDRKE

ASSTVLVSFGSEFFLSKEETEAIAHGLEQSEAN

FIWGIRFPKGAKKNAIEEALPEGFLERVGGRAM

VVEEWVPQGKILKHGNIGGFVSHCGWNSAMESI

MCGVPVIGIPMQVDQPFNAGILEEAGVGVEAKR

DSDGKIQRDEVAKLIKEVVVERTREDIRNKLEE

INEILRIRREEKLDELATEISLLCKN

>OM057892.1 UDP-glucuronosyl/UDP-
glucosyltransferase
[Corchorus capsularis]
(SEQ ID NO: 39)
MDSKQKKMSVLMFPWLAYGHISPFLELAKKLSK

RNFHTFFFSTPINLNSIKSKLSPKYAQSIQFVE

LHLPSLPDLPPHYHTINGLPPHLMNILKKAFDM

SSLQFSKILKILNPDLLVYDFIQPWAPLLALSN

KIPAVHFLCTSAAMSSFSVHAFKKPCEDFPFPN

IYVHGNFMNAKFNNMENCSSDDSISDQDRVLQC

FERSTKIILVKIFEELEGKFMDYLSVLLNKKIV

PIGPLIQDPNEDEGDDDERTKLLLEWLNKKSKS

STVFVSFGSEYFLSKEEREEIAYGLELSKVNFI

WVIRFPLGENKTNLEEALPQGFLQRVSERGLVV

ENWAPQAKILQHSIGGFVSHCGWSSVMESLKF

GVPIIAIPMHLDQPLNARLVVDVGVGLEVIRNH

GSLEREEIAKLIKEVVLGNGNDGEIVRRKAREM

SNHIKKKGEKDMDELVEELMLICKMKPNSCHLS

>XP_015886141.1 PREDICTED: beta-
D-glucosyl crocetin beta-1,6-
glucosyltransferase-like isoform X1
[Ziziphus jujuba]
(SEQ ID NO: 40)
MMERQRSIKVLMFPWLAHGHISPFLELAKRLTD

RNFQIYFCSTPVNLTSVKPKLSQKYSSSIKLVE

LHLPSLPDLPPHYHTINGLALNLIPTLKKAFDM

SSSSFSTILSTIKPDLLIYDFLQPWAPQLASCM

NIPAVNFLSAGASMVSFVLHSIKYNGDDHDDEF

LITELHLSDSMEAKFAEMTESSPDEHIDRAVIC

LERSNSLILIKSFRELEGKYLDYLSLSFAKKVV

PIGPLVAQDINPEDDSMDIINWLDKKEKSSIVF

VSFGSEYYLTNEEMEEIAYGLELSKVNFIWVVR

FPLGQKMAVEEALPKGFLERVGEKGMVVEDWAP

QMKILGHSSIGGFVSHCGWSSLMESLKLGVPII

AMPMQLDQPINAKLVERSGVGLEVKRDKNGRIE

REYLAKVIREIVVEKARQDIEKKAREMSNIITE

KGEEEIDNVVEELAKLCGM

>XP_002271587.3 PREDICTED:
beta-D-glucosyl crocetin beta-1,6-
glucosyltransferase-like
[Vitis vinifera]
(SEQ ID NO: 41)
MDARQSDGISVLMFPWLAHGHISPFLQLAKKLS

KRNFSIYFCSTPVNLDPIKGKLSESYSLSIQLV

KLHLPSLPELPPQYHTINGLPPHLMPTLKMAFD

MASPNFSNILKILHPDLLIYDFLQPWAPAAASS

LNIPAVQFLSTGATLQSFLAHRHRKPGIEFPFQ

EIHLPDYEIGRLNRFLEPSAGRISDRDRANQCL

ERSSRFSLIKTFREIEAKYLDYVSDLIKKKMVT

VGPLLQDPEDEDEATDIVEWLNKKCEASAVEVS

FGSEYFVSKEEMEEIAHGLELSNVDFIWVVRFP

MGEKIRLEDALPPGFLHRLGDRGMVVEGWAPQR

KILGHSSIGGFVSHCGWSSVMEGMKFGVPIIAM

PMHLDQPINAKLVEAVGVGREVKRDENRKLERE

EIAKVIKEVVGEKNGENVRRKARELSETLRKKG

DEEIDVVVEELKQLCSY

>XP_018840205.1 PREDICTED: beta-D-
glucosyl crocetin beta-1,6-
glucosyltransferase-like
[Juglans regia]
(SEQ ID NO: 42)
MDTARKRIRVVMLPWLAHGHISPFLELSKKLAK

RNFHIYFCSTPVNLSSIKPKLSGKYSRSIQLVE

LHLPSLPELPPQYHTTKGLPPHLNATLKRAFDM

-continued

AGPHFSNILKILSPDLLIYDFLQPWAPAIAASQ

NIPAINFLSTGAAMTSFVLHAMKKPGDEFPFPE

IHLDECMKTREVDLPEDHSPSDDHNHISDKDRA

LKCFERSSGFVMMKTFEELEGKYINFLSHLMQK

KIVPVGPLVQNPVRGDHEKAKTLEWLDKRKQSS

AVFVSFGTEYFLSKEEMEEIAYGLELSNVNFIW

VVRFPEGEKVKLEEALPEGFLQRVGEKGMVVEG

WAPQAKILMHPSIGGFVSHCGWSSVMESIDFGV

PIVAIPMQLDQPVNAKVVEQAGVGVEVKRDRDG

KLEREEVATVIREVVMGNIGESVRKKEREMRDN

IRKKGEEKMDGVAQELVQLYGNGIKNV

>XP_021652171.1 beta-D-glucosyl crocetin beta-1,6-glucosyltransferase-like [Hevea brasiliensis]
(SEQ ID NO: 43)
METLQRRKISVLMFPWLAHGHLSPFLELSKKLN

KRNFHVYFCSTPVNLDSIKPKLSAEYSFSIQLV

ELHLPSSPELPLHYHTINGLPPHLMKNLKNAFD

MASSSFFNILKILKPDLLIYDFIQPWAPALASS

LNIPAVNFLCTSMAMSCFGLHLNNQEAKFPFPG

IYPRDYMRMKVEGALESSSNDIKDGERAGRCMD

QSFHLILAKTFRELEGKYIDYLSVKLMKKIVPV

GPLVQDPIFEDDEKIMDHHQVIKWLEKKERLST

VFVSFGTEYFLSTEEMEEIAYGLELSKAHFIWV

VREPTGEKINLEESLPKRYLERVQERGKIVEGW

APQQKILRHSSIGGFVSHCGWSSIMESMKFGVP

IIAMPMNLDQPVNSRIVEDAGVGIEVRRNKSGE

LEREEIAKTIRKVVVEKDGKNVSRKAREMSDTI

RKKGEEEIDGVVDELLQLCDVKINYLQ

>XP_021619073.1 beta-D-glucosyl crocetin beta-1,6-glucosyltransferase-like [Manihot esculenta]
(SEQ ID NO: 44)
MATAQTRKISVLMFPWLAHGHLSPFLELSKKLA

NRNFHVYFCSTPVNLDSIKPKLSPEYHFSIQFV

ELHLPSSPELPSHYHTINGLPPHLMKTLKKAFD

MASSSFFNILKILNPDLLIYDFLQPWAPALASS

LNIPAVNFLCSSMAMSCFGLNLNKNKEIKFLEP

EIYPRDYMEMKLFRVFESSSNQIKDGERAGRCI

DQSFHVILAKTFRELEGKYIDYVSVKCNKKIVP

VGPLVEDTIHEDDEKTMDHHHHHHDEVIKWLEK

KERSTIVFVSFGSEYFLSKEEMEEIAHGLELSK

VNFIWVVRFPKGEKINLEESLPEGYLERIQERG

KIVEGWAPQRKILGHSSIGGFVSHCGWSSIMES

-continued

MKLGVPIIAMPMNLDQPINSRIVEAAGVGIEVS

RNQSGELEREEMAKTIRKVVVEREGVYVRRKAR

EMSDVLRKKGEEEIDGVVDELVQLCDMKTNYL

>GAV83746.1 UDPGT domain-containing protein [Cephalotus follicularis]
(SEQ ID NO: 45)
MDLKRRSIRVLMLPWLAHGHISPFLELAKKLIN

RNFLIYFCSTPINLNSIKPKLSSKYSFSIQLVE

LHLPSLPELPPHYHTINGLPLHLMNILKTAFDM

ASPSFLNILKILKPDLLICDHLQPWAPSLASSL

NIPAIIFPINSAIMMAFSLHHAKNPGEEFPFPS

ININDDMVKSINFLHSASNGLTDMDRVLQCLER

SSNTMLLKTFRQLEAKYVDYSSALLKKKIVLAG

PLVQVPDNEDEKIEIIKWLDSRGQSSIVFVSFG

SEYFLSKEEREDIAHGLELSKVNFIWVVRFPVG

EKVKLEEALPNGFAERIGERGLVVEGWAPQAMI

LSHSSIGGFVSHCGWSSMMESMKFGVPIIAMPM

HIDQPLNARLVEDVGVGLEIKRNKDGRFEREEL

ARVIKEVLVYKNGDAVRSKAREMSEHIKKNGDQ

EIDGVADALVKLCEMKINSLNQD

>Coffea Arabica UGT 1,6
(SEQ ID NO: 46)
MENHATFNVLMLPWLAHGHVSPYLELAKKLTAR

NFNVYLCSSPATLSSVRSKLTEKFSQSIHLVEL

HLPKLPELPAEYHTINGLPPHLMPTLKDAFDMA

KPNFCNVLKSLKPDLLIYDLLQPWAPEAASAFN

IPAVVFISSSATMTSFGLHFFKNPGIKYPYGNA

IFYRDYESVFVENLIRRDRDTYRVINCMERSSK

IILIKGFNEIEGKYFDYFSCLIGKKVVPVGPLV

QDPVLDDEDCRIMQWLNKKEKGSTVFVSFGSEY

FLSKKDMEEIAHGLEVSNVDFIWVVRFPKGENI

VIEETLPKGFFERVGERGLVVNGWAPQAKILTH

PNVGGFVSHCGWNSVMESMKFGLPIIAMPMHLD

QPINARLIEEVGAGVEVLRDSKGKLHRERMAET

INKVMKEASGESVRKKARELQEKLELKGDEEID

DVVKELVQLCATKNKRNGLHYY

>Circular permutant linker sequence
(SEQ ID NO: 47)
GSGGSG

>Circular permutant linker sequence
(SEQ ID NO: 48)
GSGGSGGSG

The invention claimed is:

1. A method for producing a glycosylated product from glycoside intermediates, comprising:
   providing a bacterial cell expressing one or more UDP-dependent glycosyl transferase enzymes (UGT enzymes) intracellularly wherein the UGT enzymes glycosylate steviol glycoside substrates, wherein the bacterial cell has an overexpression of phosphoglucomutase (pgm) and UTP-glucose-1-phosphate uridylyltransferase; and a deletion, inactivation, or reduced expression of one or more genes encoding enzymes that consume UDP-glucose selected from a UDP-sugar hydrolase, an enzyme responsible for UDP-galactose biosynthesis from UDP-glucose, a trehalose-6-phosphate synthase, and a UDP-glucose-6-dehydrogenase,
   incubating the bacterial strain with the glycoside intermediates, wherein the glycoside intermediates are steviol glycosides from *stevia* leaf extract, and
   recovering the glycosylated product.

2. The method of claim 1, wherein the glycosylated product comprises RebM.

3. The method of claim 1, wherein the glycosylated product comprises RebD and/or RebI.

4. The method of claim 1, wherein the bacterial cell has a deletion, inactivation, or reduced activity of ushA and/or one or more of galE, galT, galK, and galM.

5. The method of claim 4, wherein galETKM genes are inactivated, deleted, or reduced in expression.

6. The method of claim 1, wherein the bacterial cell has a deletion, inactivation, or reduced activity or expression of trehalose-6-phosphate synthase.

7. The method of claim 1, wherein the bacterial cell has a deletion, inactivation, or reduced activity or expression of UDP-glucose 6-dehydrogenase.

8. The method of claim 1, wherein the bacterial cell has a deletion, inactivation, or reduced activity or expression of glucose-6 phosphate isomerase.

9. The method of claim 1, wherein the method is performed by batch fermentation, continuous fermentation, or semi-continuous fermentation.

10. The method of claim 9, wherein the method is performed by fed batch fermentation.

11. The method of claim 10, wherein the glycoside intermediates are incubated with the cell for about 72 hours or less.

12. The method of claim 1, wherein the bacterial cell is selected from *Escherichia* spp., *Bacillus* spp., *Rhodobacter* spp., *Zymomonas* spp., or *Pseudomonas* spp.

13. The method of claim 12, wherein the bacterial cell is a species selected from *Escherichia coli, Bacillus subtilis, Rhodobacter capsulatus, Rhodobacter sphaeroides, Zymomonas mobilis,* or *Pseudomonas putida*.

14. The method of claim 13, wherein the bacterial cell is *Escherichia coli*.

15. The method of claim 1, wherein the bacterial cell expresses a 1-3' glycosylating UGT enzyme and a 1-2' glycosylating enzyme.

16. The method of claim 15, wherein the 1-3' glycosylating UGT enzyme comprises an amino acid sequence selected from SEQ ID NO: 3, SEQ ID NO: 10, SEQ ID NO: 15, SEQ ID NO: 16, and SEQ ID NO: 17, and derivatives thereof having at least 90% sequence identity thereto.

17. The method of claim 15, wherein the 1-2' glycosylating UGT enzyme comprises an amino acid sequence selected from SEQ ID NO: 4, SEQ ID NO: 5, SEQ ID NO: 6, SEQ ID NO: 7, SEQ ID NO: 9, and SEQ ID NO: 11, and derivatives thereof having at least 90% sequence identity thereto.

* * * * *